United States Patent [19]

Talley et al.

[11] Patent Number: 5,482,947
[45] Date of Patent: Jan. 9, 1996

[54] RETROVIRAL PROTEASE INHIBITORS

[76] Inventors: John J. Talley, 1510 Amisk Ct.; Daniel P. Getman, 66 Sunnyhill Ct., both of Chesterfield, Mo. 63017; Gary A. DeCrescenzo, 536 Schrader Farm Dr., St. Peters, Mo. 63376; Ko-Chung Lin, 12790 Polo Parc Dr., St. Louis, all of Mo. 63146; Michael L. Vazquez, 233 Saratoga Ct., Gurnee, Ill. 60031; Richard A. Mueller, 562 Stonegate Ter., Glencoe, Ill. 60022; Kathryn L. Reed, 7301-104 Brookmont Dr., Raleigh, N.C. 27613; Robert M. Heintz, 603 Nancy Pl., Ballwin, Mo. 63021; Michael Clare, 5154 W. Brown St., Skokie, Ill. 60077; John N. Freskos, 7572 York, Clayton, Mo. 63105; Eric T. Sun, 1647 Johnson Dr., Apartment 433, Buffalo Grove, Ill. 60089

[21] Appl. No.: 152,934

[22] Filed: Nov. 15, 1993

Related U.S. Application Data

[63] Continuation of Ser. No. 886,558, May 20, 1992, abandoned, which is a continuation-in-part of Ser. No. 789,646, Nov. 14, 1991, abandoned, which is a continuation-in-part of Ser. No. 615,210, Nov. 19, 1990, abandoned.

[51] Int. Cl.⁶ .......................... A61K 31/47; A61K 31/17; C07D 215/48
[52] U.S. Cl. .................. 514/311; 514/235.2; 514/314; 514/482; 514/588; 514/596; 544/128; 546/169; 560/27; 560/29; 560/125; 564/47; 564/56; 564/57; 564/59
[58] Field of Search .......................... 546/169; 544/128; 560/27, 29, 125; 564/47, 56, 57, 59

[56] References Cited

U.S. PATENT DOCUMENTS

| H725 | 1/1990 | Gordon | 548/533 |
|---|---|---|---|
| 4,450,164 | 5/1984 | Bristol et al. | 424/256 |
| 4,477,441 | 10/1984 | Boger et al. | 424/177 |
| 4,514,391 | 4/1985 | Gordon et al. | 514/2 |
| 4,548,926 | 10/1985 | Matsueda et al. | 514/19 |
| 4,599,198 | 7/1986 | Hoover | 260/998.2 |
| 4,616,088 | 10/1986 | Ryono et al. | 546/336 |
| 4,668,769 | 5/1987 | Hoover | 530/331 |
| 4,668,770 | 5/1987 | Boger et al. | 530/331 |
| 4,757,050 | 7/1988 | Natarajan et al. | 514/18 |
| 4,880,938 | 11/1989 | Freidinger | 548/492 |
| 4,963,530 | 10/1990 | Hemmi et al. | 514/19 |
| 4,977,277 | 12/1990 | Rosenberg et al. | 549/215 |
| 5,132,400 | 7/1992 | Gammill et al. | 530/317 |
| 5,151,438 | 9/1992 | Sham et al. | 546/300 |

FOREIGN PATENT DOCUMENTS

| 79823/87 | 4/1988 | Australia . |
|---|---|---|
| 114993 | 12/1982 | European Pat. Off. . |
| 104041 | 3/1984 | European Pat. Off. . |
| 172347 | 2/1986 | European Pat. Off. . |
| 223437 | 5/1987 | European Pat. Off. . |
| 0264795 | 4/1988 | European Pat. Off. . |
| 337414 | 10/1989 | European Pat. Off. . |
| 0342541 | 11/1989 | European Pat. Off. . |
| 0346847 | 12/1989 | European Pat. Off. . |
| 356223 | 2/1990 | European Pat. Off. . |
| 393445 | 10/1990 | European Pat. Off. . |
| 393457 | 10/1990 | European Pat. Off. . |
| 389898A2 | 10/1990 | European Pat. Off. . |
| 389898A3 | 10/1990 | European Pat. Off. . |
| 402646 | 12/1990 | European Pat. Off. . |
| 2184730 | 7/1987 | United Kingdom . |
| 2200115 | 7/1988 | United Kingdom . |
| 2209752 | 5/1989 | United Kingdom . |
| WO84/03044 | 8/1984 | WIPO . |

OTHER PUBLICATIONS

Plattner et al., J. Med. Chem., 31, 2277–2288 (1988).
Bolis et al., J. Med. Chem., 30, 1729–1737 (1987).
Haber et al., J. Cardiovascular Pharm. 554–558 (1987).
Burger, Medicinal Chemistry, pp. 565–571, 578–581, 600–601 (1960).
Denkelwalter et al., Progress in Drug Research pp. 510–512 (1966).
Rich et al, Peptide Inhibitors of Proteases, 511–520 (1990).
Rosenberg et al, *J. Med. Chem.*, 30, 1224–1228 (1987).
Roberts et al, "Rational Design of Peptide–based Proteinase Inhibitors," *Science*, 248, 358 (1990).
Erickson et al, "Design activity, and 2.8Å Crystal Structure of a $C_2$ Symmetric Inhibitor Complexed to HIV–1 Protease," Science, 249, 527 (1990).
Pearl et al, "Sequence specificity of retroviral proteases" *Nature*, 328, (1987).
Martin, *Drugs of the Future*, 16(3), 210–212 (1991).
Meek et al, *Letter To Nature*, 343, 90–92 (1990).
McQuade et al, *Science*, 247, 454–456 (1990).

*Primary Examiner*—Bernard Dentz
*Attorney, Agent, or Firm*—Frank S. Ungemach

[57] ABSTRACT

Urea-containing hydroxyethylamine compounds are effective as retroviral protease inhibitors, and in particular as inhibitors of HIV protease.

18 Claims, No Drawings

RETROVIRAL PROTEASE INHIBITORS

This application is a continuation, of application Ser. No. 07/886,558 filed May 20, 1992 now abandoned, which application is a continuation-in-part of patent application Ser. No. PCT/US91/8613, filed Nov. 18, 1991, which is a continuation-in-part of 07/789,646, filed Nov. 14, 1991, now abandoned which is a continuation-in-part of U.S. patent application Ser. No. 07/615,210, filed Nov. 19 1990, now abandoned.

BACKGROUND OF THE INVENTION

1. Field of the Invention

The present invention relates to retroviral protease inhibitors and, more particularly, relates to novel compounds and a composition and method for inhibiting retroviral proteases. This invention, in particular, relates to urea-containing hydroxyethylamine protease inhibitor compounds, a composition and method for inhibiting retroviral proteases such as human immunodeficiency virus (HIV) protease and for treatment or prophylaxis a retroviral infection, e.g., an HIV infection. The subject invention also relates to processes for making such compounds as well as to intermediates useful in such processes.

2. Related Art

During the replication cycle of retroviruses, gag and gag-pol gene products are translated as proteins. These proteins are subsequently processed by a virally encoded protease (or proteinase) to yield viral enzymes and structural proteins of the virus core. Most commonly, the gag precursor proteins are processed into the core proteins and the pol precursor proteins are processed into the viral enzymes, e.g., reverse transcriptase and retroviral protease. It has been shown that correct processing of the precursor proteins by the retroviral protease is necessary for assembly of infectious virons. For example, it has been shown that frameshift mutations in the protease region of the pol gene of HIV prevents processing of the gag precursor protein. It has also been shown through site-directed mutagenesis of an aspartic acid residue in the HIV protease that processing of the gag precursor protein is prevented. Thus, attempts have been made to inhibit viral replication by inhibiting the action of retroviral proteases.

Retroviral protease inhibition typically involves a transition-state mimetic whereby the retroviral protease is exposed to a mimetic compound which binds (typically in a reversible manner) to the enzyme in competition with the gag and gag-pol proteins to thereby inhibit replication of structural proteins and, more importantly, the retroviral protease itself. In this manner, retroviral replication proteases can be effectively inhibited.

Several classes of mimetic compounds have been proposed, particularly for inhibition of proteases, such as for inhibition of HIV protease. Such mimetics include hydroxyethylamine isosteres and reduced amide isosteres. See, for example, EP 0 346 847; EP 0 342,541; Roberts et al, "Rational Design of Peptide-Based Proteinase Inhibitors," *Science,* 248, 358 (1990); and Erickson et al, "Design Activity, and 2.8A Crystal Structure of a $C_2$ Symmetric Inhibitor Complexed to HIV-1 Protease," *Science,* 249, 527 (1990).

Several classes of mimetic compounds are known to be useful as inhibitors of the proteolytic enzyme renin. See, for example, U.S. Pat. No. 4,599,198; U.K. 2,184,730; G.B. 2,209,752; EP 0 264 795; G.B. 2,200,115 and U.S. SIR H725. Of these, G.B. 2,200,115, GB 2,209,752, EP 0 264, 795, U.S. SIR H725 and U.S. Pat. No. 4,599,198 disclose urea-containing hydroxyethylamine renin inhibitors. However, it is known that, although renin and HIV proteases are both classified as aspartyl proteases, compounds which are effective renin inhibitors generally cannot be predicted to be effective HIV protease inhibitors.

BRIEF DESCRIPTION OF INVENTION

The present invention is directed to virus inhibiting compounds and compositions. More particularly, the present invention is directed to retroviral protease inhibiting compounds and compositions, to a method of inhibiting retroviral proteases, to processes for preparing the compounds and to intermediates useful in such processes. The subject compounds are characterized as urea-containing hydroxyethylamine inhibitor compounds.

DETAILED DESCRIPTION OF THE INVENTION

In accordance with the present invention, there is provided a retroviral protease inhibiting compound of the formula:

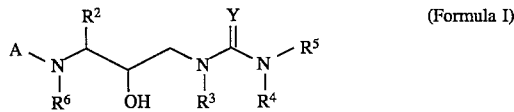

(Formula I)

or a pharmaceutically acceptable salt, prodrug or ester thereof wherein:

A represents radicals represented by the formulas:

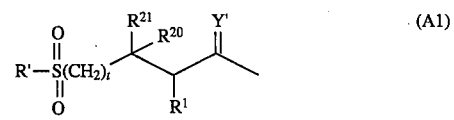

(A1)

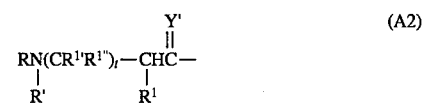

(A2)

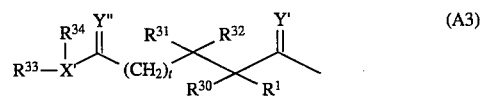

(A3)

wherein R represents hydrogen, alkoxycarbonyl, aralkoxycarbonyl, alkylcarbonyl, cycloalkylcarbonyl, cycloalkylalkoxycarbonyl, cycloalkylalkanoyl, alkanoyl, aralkanoyl, aroyl, aryloxycarbonyl, aryloxycarbonylalkyl, aryloxyalkanoyl, heterocyclylcarbonyl, heterocyclyloxycarbonyl, heterocyclylalkanoyl, heterocyclylalkoxycarbonyl, heteroaralkoxycarbonyl, heteroaryloxycarbonyl, heteroaroyl, heteroaralkanoyl, alkyl, aryl, aralkyl, aryloxyalkyl, heteroaryloxyalkyl, hydroxyalkyl, aminocarbonyl, aminoalkanoyl, and mono- and disubstituted aminocarbonyl and mono- and disubstituted aminoalkanoyl radicals wherein the substituents are selected from alkyl, aryl, aralkyl, cycloalkyl, cycloalkylalkyl, heteroaryl, heteroaralkyl, heterocycloalkyl, and heterocycloalkyalkyl radicals, or in the case of a disubstituted aminoalkanoyl radical, said substituents along with the nitrogen atom to which they are attached form a heterocyclyl or heteroaryl radical;

R' represents hydrogen and radicals as defined for $R^3$ or R and R' together with the nitrogen to which they are attached form a heterocycloalkyl or heteroaryl radical, or when A is Al, R' represents hydrogen, radicals as defined for $R^3$ and arakloxycarbonylalkyl and aminocarbonylalkyl and aminocarbonyl radicals wherein said amino group may be mono- of disubstituted with subsituents selected form alkyl, aryl, aralkyl, cycloalkyl, cycloalkylalkyl, heteroaryl, heteroaralkyl, heterocycloalkyl and heterocycloalkylalkyl radicals;

t represents either 0 or 1;

$R^1$ represents hydrogen, —$CH_2SO_2NH_2$, —$CO_2CH_3$, —$CONHCH_3$, —$CON(CH_3)_2$, —$CH_2C(O)NHCH_3$, —$CH_2C(O)N(CH_3)_2$, —$CONH_2$, —$C(CH_3)_2(SCH_3)$, —$C(CH_3)_2(S[O]CH_3)$, —$C(CH_3)_2(S[O]CH_3)$, alkyl, haloalkyl, alkenyl, alkynyl and cycloalkyl radicals and amino acid side chains selected from asparagine, S-methyl cysteine and the corresponding sulfoxide and sulfone derivatives thereof, glycine, leucine, isoleucine, allo-isoleucine, tert-leucine, phenylalanine, ornithine, alanine, histidine, norleucine, glutamine, valine, threonine, serine, aspartic acid, beta-cyano alanine, and allothreonine side chains;

$R^{1'}$ and $R^{1''}$ independently represent hydrogen and radicals as defined for $R^1$, or one of $R^{1'}$ and $R^{1''}$, together with $R^1$ and the carbon atoms to which $R^1$, $R^{1'}$ and $R^{1''}$ are attached, represent a cycloalkyl radical;

$R^2$ represents alkyl, aryl, cycloalkyl, cycloalkylalkyl and aralkyl radicals, which radicals are optionally substituted with a group selected from —$NO_2$, —$OR^9$, —$SR^9$, and halogen radicals, wherein $R^9$ represents hydrogen and alkyl radicals;

$R^3$ represents alkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical;

X' represents O, $C(R^{17})$ where $R^{17}$ represents hydrogen and alkyl radicals, and N;

Y, Y', and Y" independently represent O,S and $NR^{15}$ wherein $R^{15}$ represents hydrogen and radicals as defined for $R^3$;

$R^4$ and $R^5$ independently represent hydrogen and radicals as defined by $R^3$, or $R^4$ and $R^5$ together with the nitrogen atom to which they are bonded represent heterocycloalkyl and heteroaryl radicals;

$R^6$ represents hydrogen and alkyl radicals;

$R^{20}$, $R^{21}$, $R^{30}$, $R^{31}$ and $R^{32}$ represent radicals as defined for $R^1$, or one of $R^1$ and $R^{30}$ together with one of $R^{31}$ and $R^{32}$ and the carbon atoms to which are attached form a cycloalkyl radical; and $R^{33}$ and $R^{34}$ independently represent hydrogen and radicals as defined for $R^3$, or $R^{33}$ and $R^{34}$ together with X' represent cycloalkyl, aryl, heterocyclyl and heteroaryl radicals, provided that when X' is O, $R^{34}$ is absent.

A preferred class of retroviral inhibitor compounds of the present invention are those represented by the formula:

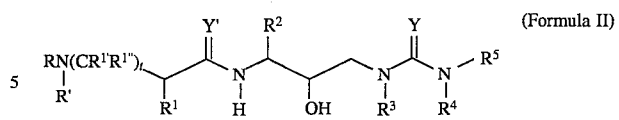

(Formula II)

or a pharmaceutically acceptable salt, prodrug or ester thereof, preferably wherein the stereochemistry about the hydroxy group is designated as (R);

R represents hydrogen, alkoxycarbonyl, aralkoxycarbonyl, alkylcarbonyl, cycloalkylcarbonyl, cycloalkylalkoxycarbonyl, cycloalkylalkanoyl, alkanoyl, aralkanoyl, aroyl, aryloxycarbonyl, aryloxycarbonylalkyl, aryloxyalkanoyl, heterocyclylcarbonyl, heterocyclyloxycarbonyl, heterocyclylalkanoyl, heterocyclylalkoxycarbonyl, heteroaralkanoyl, heteroaralkoxycarbonyl, heteroaryloxycarbonyl, heteroaroyl, alkyl, alkenyl, cycloalkyl, aryl, aralkyl, aryloxyalkyl, heteroaryloxyalkyl, hydroxyalkyl, aminocarbonyl, aminoalkanoyl, and mono- and disubstituted aminocarbonyl and mono- and disubstituted aminoalkanoyl radicals wherein the substituents are selected from alkyl, aryl, aralkyl, cycloalkyl, cycloalkylalkyl, heteroaryl, heteroaralkyl, heterocycloalkyl, heterocycloalkylalkyl radicals, or where said aminoalkanoyl radical is disubstituted, said substituents along with the nitrogen atom to which they are attached form a heterocycloalkyl or heteroaryl radical;

R' represents hydrogen and radicals as defined for $R^3$ or R and R' together with the nitrogen to which they are attached represent heterocycloalkyl and heteroaryl radical;

$R^1$ represents hydrogen, —$CH_2SO_2NH_2$, —$CH_2CO_2CH_3$, —$CO_2CH_3$, —$CONH_2$, —$CHC(O)NHCH_3$, —$C(CH_3)_2(SCH_3)$, —$C(CH_3)_2(S[O]CH_3)$, —$C(CH_3)_2(S[O]_2CH_3)$, alkyl, haloalkyl, alkenyl, alkynyl and cycloalkyl radicals, and amino acid side chains selected from asparagine, S-methyl cysteine and the sulfoxide (SO) and sulfone ($SO_2$) derivatives thereof, isoleucine, allo-isoleucine, alanine, leucine, tert-leucine, phenylalanine, ornithine, histidine, norleucine, glutamine, threonine, glycine, allo-threonine, serine, aspartic acid, beta-cyano alanine and valine side chains;

$R^{1'}$ and $R^{1''}$ independently represent hydrogen and radicals as defined for $R^1$, or one of $R^{1'}$ and $R^{1''}$, together with $R^1$ and the carbon atoms to which $R^1$, $R^{1'}$ and $R^{1''}$ are attached, represent a cycloalkyl radical;

$R^2$ represents alkyl, aryl, cycloalkyl, cycloalkylalkyl, and aralkyl radicals, which radicals are optionally substituted with a group selected from alkyl radicals, $NO_2$, $OR^9$ and $SR^9$ wherein $R^9$ represents hydrogen and alkyl radicals, and halogen radicals;

$R^3$ represents alkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical;

$R^4$ and $R^5$ independently represent hydrogen and radicals as defined by $R^3$, or together with a nitrogen atom to which they are bonded represent heterocycloalkyl and heteroaryl radicals;

t represents 0 or 1;

Y and Y' independently represent O, S, and $NR^{15}$ wherein $R^{15}$ represents hydrogen and radicals as defined for $R^3$. Preferably, Y and Y' represent O.

Preferably, $R^3$ represents radicals as defined above which contain no α-branching, e.g., as in an isopropyl radical or a t-butyl radical. The preferred radicals are those which contain a —$CH_2$— moiety between the nitrogen of the urea and the remaining portion of the radical. Such preferred groups include, but are not limited to, benzyl, isobutyl, n-butyl, isoamyl, cyclohexylmethyl and the like.

Another preferred class of compounds are those represented by the formula:

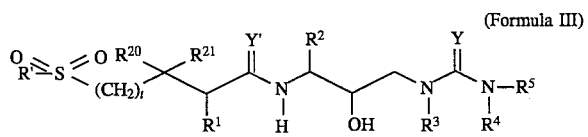

(Formula III)

or a pharmaceutically acceptable salt, prodrug or ester thereof wherein t, Y, Y', R', $R^1$, $R^2$, $R^3$, $R^4$, $R^5$, $R^{20}$ and $R^{21}$ are as defined above with respect to Formula I. Preferably, the stereochemistry about the hydroxyl group is designated as R.

Yet another preferred class of compounds are those represented by the formula:

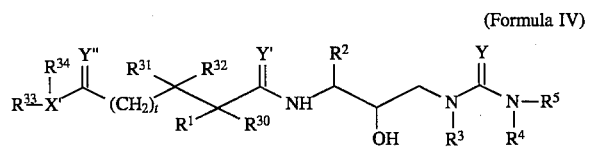

(Formula IV)

or a pharmaceutically acceptable salt, prodrug or ester thereof, preferably wherein the stereochemistry about the hydroxy group is designated as R, wherein t, X', Y, Y', Y", $R^1$, $R^2$, $R^3$, $R^4$, $R^5$, $R^{30}$, $R^{31}$, $R^{32}$, $R^{33}$ and $R^{34}$ are as defined above with respect to Formula I.

As utilized herein, the term "alkyl", alone or in combination, means a straight-chain or branched-chain alkyl radical containing from 1 to about 10, preferably from 1 to about 8, carbon atoms. Examples of such radicals include methyl, ethyl, n-propyl, isopropyl, n-butyl, isobutyl, sec-butyl, tert-butyl, pentyl, iso-amyl, hexyl, octyl and the like. The term "alkenyl", alone or in combination, means a straight-chain or branched-chain hydrocarbon radial having one or more double bonds and containing from 2 to about 18 carbon atoms preferably from 2 to about 8 carbon atoms. Examples of suitable alkenyl radicals include ethenyl, propenyl, alkyl, 1,4-butadienyl and the like. The term "alkynyl", alone or in combination, means a straight-chain hydrocarbon radical having one or more triple bonds and containing from 2 to about 10 carbon atoms. Examples of alkynyl radicals include ethynyl, propynyl, (propargyl), butynyl and the like. The term "alkoxy", alone or in combination, means an alkyl ether radical wherein the term alkyl is as defined above. Examples of suitable alkyl ether radicals include methoxy, ethoxy, n-propoxy, isopropoxy, n-butoxy, iso-butoxy, sec-butoxy, tert-butoxy and the like. The term "cycloalkyl", alone or in combination, means an alkyl radical which contains from about 3 to about 8 carbon atoms and is cyclic. The term "cycloalkylalkyl" means an alkyl radical as defined above which is substituted by a cycloalkyl radical containing from about 3 to about 8, preferably from about 3 to about 6, carbon atoms. Examples of such cycloalkyl radicals include cyclopropyl, cyclobutyl, cyclopentyl, cyclohexyl and the like. The term "aryl", alone or in combination, means a phenyl or naphthyl radical which optionally carries one or more substituents selected from alkyl, alkoxy, halogen, hydroxy, amino, nitro and the like, such as phenyl, p-tolyl, 4-methoxyphenyl, 4-(tertbutoxy)phenyl, 4-fluorophenyl, 4-chlorophenyl, 4-hydroxyphenyl, 1-naphthyl, 2-naphthyl, and the like. The term "aralkyl", alone or in combination, means an alkyl radical as defined above in which one hydrogen atom is replaced by an aryl radical as defined above, such as benzyl, 2-phenylethyl and the like. The term "aralkoxy carbonyl", alone or in combination, means a radical of the formula —C (O) -O-aralkyl in which the term "aralkyl" has the significance given above. An example of an aralkoxycarbonyl radical is benzyloxycarbonyl. The term "aryloxy" means a radical of the formula aryl-O- in which the term aryl has the significance given above. The term "alkanoyl", alone or in combination, means an acyl radical derived from an alkanecarboxylic acid, examples of which include acetyl, propionyl, butyryl, valeryl, 4-methylvaleryl, and the like. The term "cycloalkylcarbonyl" means an acyl group derived from a monocyclic or bridged cycloalkanecarboxylic acid such as cyclopropanecarbonyl, cyclohexanecarbonyl, adamantanecarbonyl, and the like, or from a benz-fused monocyclic cycloalkanecarboxylic acid which is optionally substituted by, for example, alkanoylamino, such as 1,2,3,4-tetrahydro- 2-naphthoyl, 2-acetamido-1,2,3,4-tetrahydro-2-naphthoyl. The term "aralkanoyl" means an acyl radical derived from an aryl-substituted alkanecarboxylic acid such as phenylacetyl, 3-phenylpropionyl (hydrocinnamoyl), 4-phenylbutyryl, (2-naphthyl) acetyl, 4-chlorohydrocinnamoyl, 4-aminohydrocinnamoyl,4-methoxyhydrocinnamoyl, and the like. The term "aroyl" means an acyl radical derived from an aromatic carboxylic acid. Examples of such radicals include aromatic carboxylic acids, an optionally substituted benzoic or naphthoic acid such as benzoyl, 4-chlorobenzoyl, 4-carboxybenzoyl, 4-(benzyloxycarbonyl)benzoyl, 1-naphthoyl, 2-naphthoyl, 6-carboxy-2-naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like. The heterocyclyl or heterocycloalkyl portion of a heterocyclylcarbonyl, heterocyclyloxycarbonyl, heterocyclylalkoxycarbonyl, or heterocyclyalkyl group or the like is a saturated or partially unsaturated monocyclic, bicyclic or tricyclic heterocycle which contains one or more hetero atoms selected from nitrogen, oxygen and sulphur, which is optionally substituted on one or more carbon atoms by halogen, alkyl, alkoxy, oxo, and the like, and/or on a secondary nitrogen atom (i. e., —NH—) by alkyl, aralkoxycarbonyl, alkanoyl, phenyl or phenylalkyl or on a tertiary nitrogen atom (i. e. =N—) by oxido and which is attached via a carbon atom. The heteroaryl portion of a heteroaroyl, heteroaryloxycarbonyl, or a heteroaralkoxy carbonyl group or the like is an aromatic monocyclic, bicyclic, or tricyclic heterocycle which contains the hetero atoms and is optionally substituted as defined above with respect to the definition of heterocyclyl. Examples of such heterocyclyl and heteroaryl groups are pyrrolidinyl, piperidinyl, piperazinyl, mortDholinyl, thiamorpholinyl, pyrrolyl, imidazolyl (e.g., imidazol 4-yl, 1-benzyloxycarbonylimidazol- 4-yl, etc.), pyrazotyl, pyridyl, pyrazinyl, pyrimidinyl, furyl, thienyl, triazolyl, oxazolyl, thiazolyl, indolyl (e.g., 2-indolyl, etc.), quinolinyl, (e.g., 2-quinolinyl, 3-quinolinyl, 1-oxido-2-quinolinyl, etc.), isoquinolinyl (e.g., 1-isoquinolinyl, 3-isoquinolinyl, etc.), tetrahydroquinolinyl (e.g., 1,2,3,4-tetrahydro- 2-quinolyl, etc.), 1,2,3,4-tetrahydroisoquinolinyl (e.g., 1,2,3,4-tetrahydro- 1-oxo-isoquinolinyl, etc.), quinoxalinyl, β-carbolinyl, 2-benzofurancarbonyl, 1-, 2-, 4- or 5-benzimidazolyl, and the like. The term "cycloalkylalkoxycarbonyl" means an acyl group derived from a cycloalkylalkoxycarboxylic acid of the formula cycloalkylalkyl-O-COOH wherein cycloalkylalkyl has the significance given above. The term "aryloxyalkanoyl" means an acyl radical of the formula aryl-O-alkanoyl wherein aryl and alkanoyl have the significance given above. The term "heterocyclyloxycarbonyl" means an acyl group derived from heterocyclyl-O-COOH wherein heterocyclyl is as defined above. The term "heterocyclylalkanoyl" is an acyl radical derived from a heterocyclyl-substituted alkane carboxylic acid wherein heterocyclyl has the significance given above. The term "heterocyclylalkoxycarbonyl" means an acyl radical derived from a heterocyclyl-substituted alkane-O-CCXDH wherein heterocyclyl has the significance given above. The term "heteroaryloxycarbonyl" means an acyl radical derived from a carboxylic acid represented by heteroaryl-O-COOH wherein heteroaryl has the significance given above. The term "aminocarbonyl" alone or in combination, means an amino-substituted carbonyl (carbamoyl) group derived from an amino-substituted carboxylic acid wherein the amino group can be a primary, secondary or tertiary amino group containing substituents selected from hydrogen, and alkyl, aryl, aralkyl, cycloalkyl, cycloalkylalkyl radicals and the like. The term "aminoalkanoyl" means an acyl group derived from an amino-substituted alkanecarboxylic acid wherein the amino group can be a primary, secondary or tertiary amino group containing substituents selected from hydrogen, and alkyl, aryl, aralkyl, cycloalkyl, cycloalkylalkyl radicals and the like. The term "halogen" means fluorine, chlorine, bromine or iodine. The term "haloalkyl" means an alkyl radical having the significance as defined above wherein one or more hydrogens are replaced with a halogen. Examples of such haloalkyl radicals include chloromethyl, 1-bromoethyl, fluoromethyl, difluoromethyl, trifluoromethyl, 1,1,1-trifluoroethyl and the like. The term "leaving group" generally refers to groups readily displaceable by a nucleophile, such as an amine, a thiol or an alcohol nucleophile. Such leaving groups are well known and include carboxylates, N-hydroxysuccinimide, N-hydroxybenzotriazole, halides, triflates, rosylares —OR and —SR and the like. Preferred leaving groups are indicated herein where appropriate.

Procedures for preparing the compounds of Formula I are set forth below. It should be noted that the general procedure is shown as it relates to preparation of compounds having the specified stereochemistry, for example, wherein the stereochemistry about the hydroxyl group is designated as (R). However, such procedures are generally applicable, as illustrated in Example 45, to those compounds of opposite configuration, e.g., where the stereochemistry about the hydroxyl group is (S).

Preparation of Compounds of Formula II

The compounds of the present invention represented by Formula II above can be prepared utilizing the following general procedure. An N-protected chloroketone derivative of an amino acid having the formula:

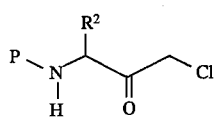

wherein P represents an amino protecting group, and $R^2$ is as defined above, is reduced to the corresponding alcohol utilizing an appropriate reducing agent. Suitable amino protecting groups are well known in the art and include carbobenzoxy, butyryl, t-butoxycarbonyl, acetyl, benzoyl and the like. A preferred amino protecting group is carbobenzoxy. A preferred N-protected chloroketone is N-benzyloxycarbonyl-L-phenylalanine chloromethyl ketone. A preferred reducing agent is sodium borohydride. The reduction reaction is conducted at a temperature of from −10° C. to about 25° C., preferably at about 0° C., in a suitable solvent system such as, for example, tetrahydrofuran, and the like. The N-protected chloroketones are commercially available from Bachem, Inc., Torrance, Calif. Alternatively, the chloroketones can be prepared by the procedure set forth in S. J. Fittkau, J. Prakt. Chem., 315, 1037 (1973), and subsequently N-protected utilizing procedures which are well known in the art.

The resulting alcohol is then reacted, preferably at room temperature, with a suitable base in a suitable solvent system to produce an N-protected amino epoxide of the formula:

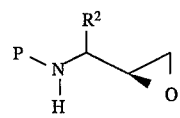

wherein P and $R^2$ are as defined above. Suitable solvent systems for preparing the amino epoxide include ethanol, methanol, isopropanol, tetrahydrofuran, dioxane, and the like including mixtures thereof. Suitable bases for producing the epoxide from the reduced chloroketone include potassium hydroxide, sodium hydroxide, potassium t-butoxide, DBU and the like. A preferred base is potassium hydroxide.

Alternatively, a protected amino epoxide can be prepared starting with an L-amino acid which is reacted with a suitable amino-protecting group in a suitable solvent to produce an amino-protected L-amino acid ester of the formula:

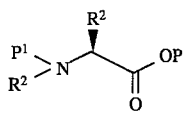

wherein P, $p^1$ and $p^2$ independently represent hydrogen and amino-protecting groups as defined above with respect to P, provided that $p^1$ and $p^2$ are not both hydrogen; and $R^2$ is as defined above.

The amino-protected L-amino acid ester is then reduced, to the corresponding alcohol. For example, the amino-protected L-amino acid ester can be reduced with diisobutylaluminumhydride at −78° C. in a suitable solvent such as toluene. The resulting alcohol is then converted, by way of a Swern Oxidation, to the corresponding aldehyde of the formula:

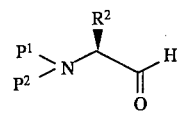

wherein $p^1$, $p^2$ and $R^2$ are as defined above. Thus, a dichloromethane solution of the alcohol is added to a cooled (−75° to −68° C.) solution of oxalyl chloride in dichloromethane and DMSO in dichloromethane and stirred for 35 minutes.

The aldehyde resulting from the Swern Oxidation is then reacted with a halomethyllithium reagent, which reagent is generated in situ by reacting an alkyllithium or aryllithium compound with a dihalomethane represented by the formula $X^1CH_2X^2$ wherein $X^1$ and $X^2$ independently represent I, Br or Cl. For example, a solution of the aldehyde and chloroiodomethane in THF is cooled to −78° C. and a solution of n-butyllithium in hexane is added. The resulting product is a mixture of diastereomers of the corresponding amino-protected epoxides of the formulas:

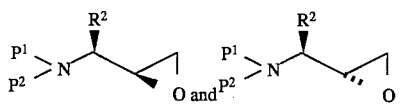

The diastereomers can be separated by chromatography or, alternatively, once reacted in subsequent steps the diastereomeric products can be separated.

The amino epoxide is then reacted, in a suitable solvent system, with an equal amount, or preferably an excess of, a desired amine of the formula:

$R^3NH_2$ wherein $R^3$ is hydrogen or is as defined above. The reaction can be conducted over a wide range of temperatures, e.g., from about 10° C. to about 100° C., but is preferably, but not necessarily, conducted at a temperature at which the solvent begins to reflux. Suitable solvent systems include those wherein the solvent is an alcohol, such as methanol, ethanol, isopropanol, and the like, ethers such as tetrahydrofuran, dioxane and the like, and toluene, N,N-dimethylformamide, dimethyl sulfoxide, and mixtures thereof. A preferred solvent is isopropanol. Exemplary amines corresponding to the formula $R^3NH_2$ include benzyl amine, isobutylamine, n-butyl amine, isopentyl amine, isoamylamine, cyclohexanemethyl amine, naphthylene methyl amine and the like. The resulting product is a 3-(N-protected amino)-3-($R^2$)-1-($NHR^3$)-propan-2-ol derivative (hereinafter referred to as an amino alcohol) can be represented by the formula:

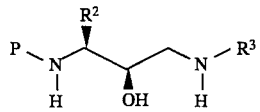

wherein P, $R^2$ and $R^3$ are as described above.

For producing compounds of Formula II wherein $R^5$ is hydrogen, the resulting amino alcohol described above is then reacted, in a suitable solvent system, with an isocyanate of the formula $R^4NCO$ wherein $R^4$ is as defined above. Where Y in Formula I above is sulfur, the resulting amino alcohol is reacted with an isothiocyanate of the formula $R^4NCS$ under similar conditions. Suitable solvent systems include tetrahydrofuran, methylene chloride, and the like and mixtures thereof. The resulting product is a urea derivative of the amino alcohol or the corresponding sulfur analog thereof and can be represented by the formula:

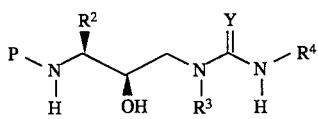

wherein P, Y, $R^2$, $R^3$ and $R^4$ are as defined above. The isocyanates of the formula $R^4NCO$ can be prepared by the reaction of an amine ($R^3NH_2$) with phosgene, triphosgene, carbodiimidazole, or carbonate ($(RO)_2CO$) under conditions well-known in the art. The isothiocyanates of the formula $R^4NCS$ can be prepared by similar procedures, e.g., reaction of the amine with thiophosgene, which are also well known in the art. In addition, the isocyanates and isothiocyanates are commercially available from Aldrich Chemical Company.

For preparing compounds of Formula II wherein $R^5$ is other than hydrogen, the resulting amino alcohol described above is then reacted, in a suitable solvent system, with a compound represented by the formula:

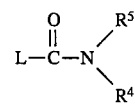

wherein $R^4$ and $R^5$ are as described above and L represents a leaving group such as a halide, e.g., chloride, imidazole radical, the radical $P-NO_2-(C_6H_4)-O-$, and the like. A preferred compound represented by this formula is a carbamoyl chloride. The corresponding sulfur analogs can be utilized where Y of Formula II is S.

The urea derivative of the amino alcohol and the corresponding sulfur analog can be represented by the formula:

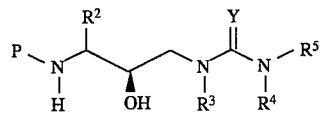

Following preparation of the urea derivative, or corresponding analogs wherein Y is S, the amino protecting group P is removed under conditions which will not affect the remaining portion of the molecule. These methods are well known in the art and include acid hydrolysis, hydrogenolysis and the like. A preferred method involves removal of the protecting group, e.g., removal of a carbobenzoxy group, by hydrogenolysis utilizing palladium on carbon in a suitable solvent system such as an alcohol, acetic acid, and the like or mixtures thereof. Where the protecting group is a t-butoxycarbonyl group, it can be removed utilizing an inorganic or organic acid, e.g., HCl or trifluoroacetic acid, in a suitable solvent system, e.g., dioxane or methylene chloride. The resulting product is the amine salt derivative. Following neutralization of the salt, the amine is then reacted with an amino acid or corresponding derivative thereof represented by the formula $(PN[CR^{1'} R^{1''}]_t\ CH(R^1)COOH)$ wherein t, $R^1$, $R^{1'}$ and $R^{1''}$ are as defined above, to produce the antiviral compounds of the present invention having the formula:

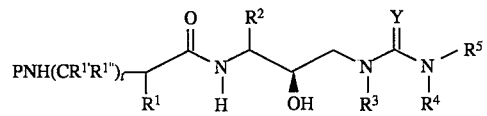

wherein t, P, $R^1$, $R^{1'}$, $R^{1''}$, $R^2$, $R^3$, $R^4$, $R^5$ and Y are as defined above. Preferred protecting groups in this instance are a benzyloxycarbonyl group or a t-butoxycarbonyl group. Where the amine is reacted with a derivative of an amino acid, e.g., when t=1 and $R^{1'}$ and $R^{1''}$ are both H, so that the amino acid is a β-amino acid, such β-amino acids can be prepared according to the procedure set forth in a copending application, U.S. Ser. No. 07/345,808. Where t is 1, one of R¹' and R¹" is H and R¹ is hydrogen so that the amino acid is a homo-β-amino acid, such homo-β-amino acids can be prepared by the procedure set forth in a copending application, U.S. Ser. No. 07/853,561. Where t is O and R¹ is alkyl, cycloalkyl, —CH₂SO₂NH₂ or an amino acid side chain, such materials are well known and many are commercially available from Sigma-Aldrich.

The N-protecting group can be subsequently removed, if desired, utilizing the procedures described above, and then reacted with a carboxylate represented by the formula:

wherein R is as defined above and L is an appropriate leaving group such as a halide. Preferably, where R¹ is a side chain of a naturally occurring α-amino acid, R is a 2-quinoline carbonyl group derived from N-hydroxysuccinimide-2-quinoline carboxylate, i.e., L is hydroxy succinimide. A solution of the free amine (or amine acetate salt) and about 1.0 equivalent of the carboxylate are mixed in an appropriate solvent system and optionally treated with up to five equivalents of a base such as, for example, N-methylmorpholine, at about room temperature. Appropriate solvent systems include tetrahydrofuran, methylene chloride or N,N-dimethylformamide, and the like, including mixtures thereof.

Preparation of Compounds of Formula III

A mercaptan of the formula RSH is reacted with a substituted methacrylate of the formula:

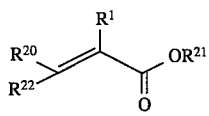

by way of a Michael Addition. The Michael Addition is conducted in a suitable solvent and in the presence of a suitable base, to produce the corresponding thiol derivative represented by the formula:

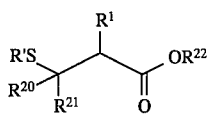

wherein R' and R¹ represent radicals defined above; R²⁰ and R²¹ represent hydrogen and radicals as defined for R¹; and R²² represents radicals as defined by R³. Suitable solvents in which the Michael Addition can be conducted include alcohols such as, for example, methanol, ethanol, butanol and the like, as well as ethers, e.g., THF, and acetonitrile, DMF, DMSO, and the like, including mixtures thereof. Suitable bases include Group I metal alkoxides such as, for example sodium methoxide, sodium ethoxide, sodium butoxide and the like as well as Group I metal hydrides, such as sodium hydride, including mixtures thereof.

The thiol derivative is converted into the corresponding sulfone of the formula:

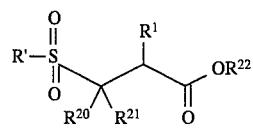

by oxidizing the thiol derivative with a suitable oxidation agent in a suitable solvent. Suitable oxidation agents include, for example, hydrogen peroxide, sodium metaperborate, oxone (potassium peromy monosulfate), meta-chloroperoxybenzoic acid, and the like, including mixtures thereof. Suitable solvents include acetic acid (for sodium meta-perborate) and, for other peracids, ethers such as THF and dioxane, and acetonitrile, DMF and the like, including mixtures thereof.

The sulfone is then converted to the corresponding free acid of the formula:

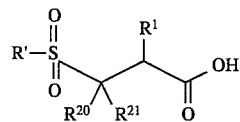

utilizing a suitable base, e.g., lithium hydroxide, sodium hydroxide, and the like, including mixtures thereof, in a suitable solvent, such as, for example, THF, acetonitrile, DMF, DMSO, methylene chloride and the like, including mixtures thereof.

The free acid is then coupled, utilizing, as described above, procedures well known in the art, to the urea derivative, or analog thereof, of an amino alcohol which is described above for the preparation of compounds of Formula II. The resulting product is a compound represented by Formula III.

Alternatively, one can couple the urea isostere to the commercially available acid,

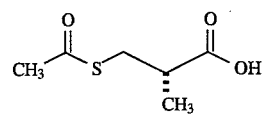

remove the thioacetyl group with a suitable base, such as hydroxide, or an amine, such as ammonia, and then react the resulting thiol with an alkylating agent, such as an alkyl halide, tosylate or mesylate to afford compounds at the following structure:

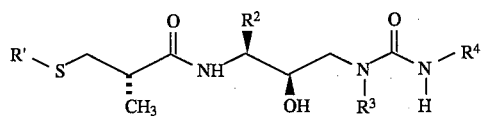

The sulfur can then be oxidized to the corresponding sulfone using suitable oxidizing agents, as described above, to afford the desired compounds of the following structure:

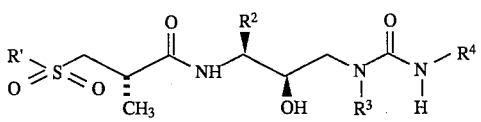

Alternatively, to prepare compounds of Fomula III, a substituted methacrylate of the formula:

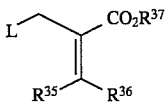

wherein L represents a leaving group as previously defined, $R^{35}$ and $R^{36}$ represent hydrogen and radicals as defined for $R^1$; and $R^{37}$ represents alkyl, aralkyl, cycloalkyl and cycloalkylalkyl radicals, is reacted with a suitable sulfonating agent, such as, for example, a sulfinic acid represented by the formula $RSO_2M$, wherein R represents radicals as defined above and M represents a metal adapted to form a salt of the acid, e.g., sodium, to produce the corresponding sulfone represented by the formula:

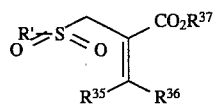

wherein R', $R^{35}$, $R^{36}$ and $R^{37}$ are as defined above. The sulfone is then hydrolyzed in the presence of a suitable base, such as lithium hydroxide, sodium hydroxide and the like, to the compound represented by the formula:

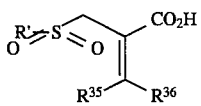

wherein R', $R^{35}$ and $R^{36}$ represent radicals as defined above. The resulting compound is then asymmetrically hydrogenated utilizing an asymmetric hydrogenation catalyst such as, for example, a ruthenium-BINAP complex, to produce the reduced product, substantially enriched in the more active isomer, represented by the formula:

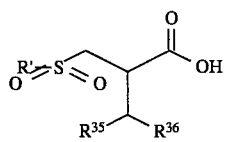

wherein R', $R^{35}$ and $R^{36}$ represent radicals as defined above. Where the more active isomer has the R-stereochemistry, a Ru(R-BINAP) asymmetric hydrogenation catalyst can be utilized. Conversely, where the more active isomer has the S-sterochemistry, a Ru(S-BINAP) catalyst can be utilized. Where both isomers are active, or where it is desired to have a mixture of the two diastereomers, a hydrogenation catalyst such as platinum, or palladium, on carbon can be utilized to reduce the above compound. The reduced compound is then coupled to the urea isostere, as described above, to produce compounds of Formula III.

Preparation of Compounds of Formula IV

To produce compounds of Formula IV, starting with a lactate of the formula:

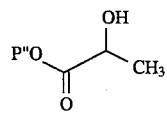

wherein P" represents alkyl radicals, such as, for example, ethyl, methyl, benzyl and the like. The hydroxyl group of the lactate is protected as its ketal by reaction in a suitable solvent system with methyl isopropenyl ether (1,2-methoxypropene) in the presence of a suitable acid. Suitable solvent systems include methylene chloride, tetrahydrofuran and the like as well as mixtures thereof. Suitable acids include $POCl_3$ and the like. It should be noted that well-known groups other than methyl isopropenyl ether can be utilized to form the ketal. The ketal is then reduced with diisobutylaluminumhydride (DIBAL) at −78° C. to produce the corresponding aldehyde which is then treated with ethylidene triphenylphosphorane (Wittig reaction) to produce a compound represented by the formula:

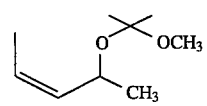

The ketal protecting group is then removed utilizing procedures well-known in the art such as by mild acid hydrolysis. The resulting compound is then esterified with isobutyryl chloride to produce a compound of the formula:

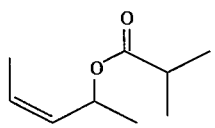

This compound is then treated with lithium diisopropyl amide at −78° C. followed by warming of the reaction mixture to room temperature to effect a Claisen rearrangement ([3,3] sigmatropic rearrangement) to produce the corresponding acid represented by the formula:

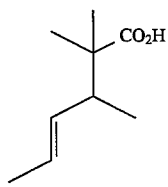

Treatment of the acid with benzyl bromide in the presence of a tertiary amine base, e.g., DBU, produces the corresponding ester which is then cleaved oxidatively to give a trisubstituted succinic acid:

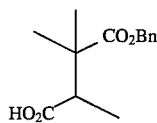

The trisubstituted succinic acid is then coupled to the urea isostere as described above. To produce the free acid, the benzyl ester is removed by hydrogenolysis to produce the corresponding acid. The acid can then be converted to the primary amide by methods well-known in the art.

An alternative method for preparing trisubstituted succinic acids involves reacting an ester of acetoacetic acid represented by the formula:

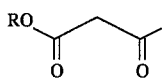

where R is a suitable protecting group, such as methyl, ethyl, benzyl or t-butyl with sodium hydride and a hydrocarbyl halide ($R^{31}X$ or $R^{32}X$) in a suitable solvent, e.g., THF, to produce the corresponding disubstituted derivative represented by the formula:

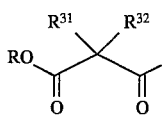

This disubstituted acetoacetic acid derivative is then treated with lithium diisopropyl amide at about −10° C. and in the presence of $PhN(triflate)_2$ to produce a vinyl triflate of the formula:

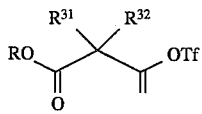

The vinyl triflate is then carbonylated utilizing a palladium catalyst, e.g., $Pd_2(OAc)_2(Ph_3)P$, in the presence of an alcohol (R"OH) or water (R'=H) and a base, e.g., triethylamine, in a suitable solvent such as DMF, to produce the olefinic ester or acid of the formula:

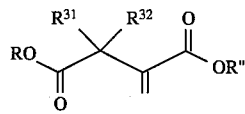

The olefin can then be subsequently asymmetrically hydrogenated, as described above, to produce a trisubstituted succinic acid derivative of the formula:

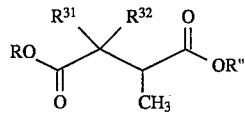

If R" is not H, R" can be removed by either hydrolysis, acidolysis, or hydrogenolysis, to afford the corresponding acid, which is then coupled to the urea isostere as described above and then, optionally, the R group removed to produce the corresponding acid, and optionally, converted to the amide.

Alternatively, one can react the urea isostere with either a suitably monoprotected succinic acid or glutaric acid of the following structure;

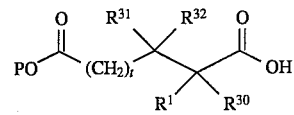

followed by removal of the protecting group and conversion of the resulting acid to an amide. One can also react an anhydride of the following structure;

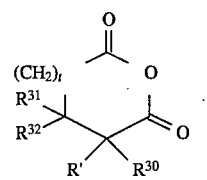

with the urea isostere and then separate any isomers or convert the resulting acid to an amide and then separate any isomers.

It is contemplated that for preparing compounds of the Formulas having $R^6$, the compounds can be prepared following the procedure set forth above and, prior to coupling the urea derivative or analog thereof, e.g. coupling to the amino acid $PNH(CH_2)_iCH(R^1)COOH$, carried through a procedure referred to in the art as reductive amination. Thus, a sodium cyanoborohydride and an appropriate aldehyde $R^6C(O)H$ or ketone $R^6C(O)R^6$ can be reacted with the urea derivative compound or appropriate analog at room temperature in order to reductively aminate any of the compounds of Formulas I–IV. It is also contemplated that where $R^3$ of the amino alcohol intermediate is hydrogen, the inhibitor compounds of the present invention wherein $R^3$ is alkyl, or other substituent wherein the α-C contains at least one hydrogen, can be prepared through reductive amination of the final product of the reaction between the amino alcohol and the amine or at any other stage of the synthesis for preparing the inhibitor compounds.

Contemplated equivalents of the general formulas set forth above for the antiviral compounds and derivatives as well as the intermediates are compounds otherwise corresponding thereto and having the same general properties such as tautomers thereof and compounds wherein one or more of the various R groups are simple variations of the substituents as defined therein, e.g., wherein R is a higher alkyl group than that indicated. In addition, where a substituent is designated as, or can be, a hydrogen, the exact chemical nature of a substituent which is other than hydrogen at that position, e.g., a hydrocarbyl radical or a halogen, hydroxy, amino and the like functional group, is not critical so long as it does not adversely affect the overall activity and/or synthesis procedure.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by

17 those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

All reagents were used as received without purification. All proton and carbon NMR spectra were obtained on either a Varian VXR-300 or VXR-400 nuclear magnetic resonance spectrometer.

EXAMPLE 1

Preparation of [1S-[1R*(R*), 2S*]]- $N^1$[3-[[[(1,1-dimethylethyl)amino]carbonyl](2-methylpropyl)amino]-2-hydroxy-1-(phenylmethyl)propyl]-2-[(2-quinolinylcarbonyl)amino]-butanediamide

Part A:

To a solution of 75.0 g (0.226 mol) of N-benzyloxycarbonyl-L-phenylalanine chloromethyl ketone in a mixture of 807 mL of methanol and 807 mL of tetrahydrofuran at −2° C., was added 13.17 g (0.348 mol, 1.54 equiv.) of solid sodium borohydride over one hundred minutes. The solvents were removed under reduced pressure at 40° C. and the residue dissolved in ethyl acetate (approx. 1L). The solution was washed sequentially with 1M potassium hydrogen sulfate, saturated sodium bicarbonate and then saturated sodium chloride solutions. After drying over anhydrous magnesium sulfate and filtering, the solution was removed under reduced pressure. To the resulting oil was added hexane (approx. 1L) and the mixture warmed to 60° C. with swirling. After cooling to room temperature, the solids were collected and washed with 2L of hexane. The resulting solid was recrystallized from hot ethyl acetate and hexane to afford 32.3 g (43% yield) of N-benzyloxycarbonyl-3(S)-amino- 1-chloro-4-phenyl-2 (S) -butanol, mp 150°–151° C. and M+Li$^+$=340.

Part B

To a solution of 6.52 g (0.116 mol, 1.2 equiv.) of potassium hydroxide in 968 mL of absolute ethanol at room temperature, was added 32.3 g (0.097 mol) of N-CBZ-3(S)-amino- 1-chloro-4-phenyl-2(S)-butanol. After stirring for fifteen minutes, the solvent was removed under reduced pressure and the solids dissolved in methylene chloride. After washing with water, drying over magnesium sulfate, filtering and stripping, one obtains 27.9 g of a white solid. Recrystallization from hot ethyl acetate and hexane afforded 22.3 g (77% yield) of N-benzyloxycarbonyl-3(S)-amino-1,2(S)-epoxy- 4-phenylbutane, mp 102°–103° C. and MH$^+$ 298.

18

Part C

A solution of N-benzyloxycarbonyl 3(S)-amino-1,2-(S)-epoxy- 4-phenylbutane (1.00 g, 3.36 mmol) and isobutylamine (4.90 g, 67.2 mmol, 20 equiv.) in 10 mL of isopropyl alcohol was heated to reflux for 1.5 hours. The solution was cooled to room temperature, concentrated in vacuo and then poured into 100 mL of stirring hexane whereupon the product crystallized from solution. The product was isolated by filtration and air dried to give 1.18 g, 95% of N=[[3 (S)-phenylmethylcarbamoyl)amino-2(R)-hydroxy- 4-phenylbutyl]N-[(2-methylpropyl)]amine mp 108.0°– 109.5° C., MH$^+$m/z=371.

Part D

A solution of [2(R), 3(S)]-N-[[3-(phenylmethylcarbamoyl)amino]- 2-hydroxy-4-phenylbutyl]N-[(2-methylpropyl)] amine in 10 ml of tetrahydrofuran was treated with tert-butylisocyanate (267 mg, 2.70 mmol) at room temperature for 5 minutes. The solvent was removed in vacuo and replaced with ethyl acetate. The ethyl acetate solution was washed with 5% citric acid, water, and brine, dried over anhydrous MgSO$_4$, filtered and concentrated in vacuo to give 1.19 g, 97% of [2(R), 3(S)]-N-[[3-(phenylmethylcarbamoyl)amino]- 2-hydroxy-4-phenyl]-1-[(2-methylpropyl)] amino-2-(1,1-dimethyl)amino] carbonyl]butane, MH$^+$ m/z–470.

Part E

A solution of (1.00 g, 2.21 mmol) [2(R), 3(S)]-N[[ 3-(phenylmethylcarbamoyl)amino]-2-hydroxy-4-phenyl]-1-[(2-methylpropyl)]amino- 1-(1,1-dimethylethyl)amino]carbonyl]butane in 20 mL of methanol was hydrogenated over 10% palladium-on-carbon for 4 hours to give [2(R), 3(S)]-N-[[3-amino]-2-hydroxy-4-phenyl]-1-[(2-methylpropyl)amino- 1-(1,1dimethylethyl)amino]carbonyl]butane 720 mg, 97%.

Part F

A solution of N-Cbz-L-asparagine (602 mg, 2.26 mmol) and N-hydroxybenzotriazole (493 mg, 3.22 mmol) in 2 mL of dimethylformamide was cooled to 0° C. and treated with EDC (473 mg, 2.47 mmol). The solution was allowed to stir at 0° C. for 20 minutes and then treated with [2(R), 3(S)]-N[ [3-amino]-2-hydroxy-4-phenyl]-1-[(2-methylpropyl)] amino-1-( 1,1-dimethylethyl)amino]carbonyl]butane (720 mg, 2.15 mmol) in 1 mL of dimethylformamide. The solution was allowed to warm to room temperature and held at this temperature for 7 hours. The reaction mixture was then poured into 100 mL of 60% saturated aqueous sodium bicarbonate whereupon a white precipitate formed that was isolated by filtration. The filter cake was washed with water, 5% aqueous citric acid, water and then dried in vacuo to give 1.04 g, 83% of [1S-[1R*(R*), 2S*]]-N$^1$[3-[ [[(1,1-dimethylethyl)amino]-carbonyl](2-methylpropyl)amino]- 2 -hydroxy-1 -(phenylmethyl) propyl]-2-[ (phenylmethylcarbamoyl)amino]-butanediamide, top. 164.0°– 166.5° C., MH$^+$m/z=584.

Part G

A solution of [1S-[1R*(R*), 2S*]]-N$^1$[3-[[[(1,1-dimethylethyl) amino]carbonyl](2-methylpropyl)amino]-2-hydroxy- 1-(phenylmethyl) propyl]-2-[(phenylmethylcarbamoyl)amino]-butanediamide (1.00 g, 1.72 mmol) in 10 mL of methanol was hydrogenated over 10% palladium-on-carbon for 4 hours to give [1S-[1R*(R*), 2S*]]-N$^1$[3-[[[(1,1-dimethylethyl)amino]carbonyl]( 2-methylpropyl)amino]-2-hydroxy-1-(phenylmethyl)propyl]- 2-amino]-butanediamide, 784 mg, 99%.

Part H

A mixture of [1S-[1R*(R*), 2S*]]-N$^1$[3-[[[(1,1-dimethylethyl)amino] carbonyl](2-methylpropyl)amino]-2-hydroxy- 1-(phenylmethyl)propyl]-2-amino]-butanediamide, (784 mg, 1.70 mmol), 2-quinoline carboxylic acid N-hydroxysuccinimide ester (459 mg, 1.70 mmol), N-methylmorpholine (343 mg, 3.40 mmol) in 5 mL of dichloromethane was stirred at room temperature for 15 minutes. The solvent was removed in vacuo and replaced with ethyl acetate and the solution washed with 5% aqueous citric acid, saturated aqueous sodium bicarbonate, brine, dried over anhydrous MgSO4, filtered and concentrated in vacuo. The crude product was recrystallized from acetone/hexane to give 790 mg, 77% of [1S-[1R*(R*), 2S*]]-N$^1$[3-[[[(1,1-dimethylethyl)amino] carbonyl](2 -methylpropyl)amino]-2-hydroxy- 1-(phenylmethyl)propyl]-2-[(2-quinolinylcarbonyl) amino]-butanediamide, mp 107.0°–109.8° C., MH$^+$= 605.

EXAMPLE 2

The procedure described in Example 1, part C-H, was used to prepare [1S-[1R* (R*), 2S*] ]-N$^1$[3-[[[(1,1-dimethylethyl)amino] carbonyl](3-methylbutyl)amino]-2-hydroxy-1-(phenylmethyl) propyl]-2-[(2-quinolinylcarbonyl)amino]-butanediamide.

a) From the reaction of 1.06 g (3.56 mmol) of N-benzyloxycarbonyl 3(S)-amino-1,2-(S)-epoxy-4-phenylbutane and 6.25 g (71.7 mmol) of isoamylamine, one obtains 1.27 g (92%) of [2 (R), 3(S)]-N-[[3-(phenylmethylcarbamoyl)amino]-2-hydroxy- 4-phenylbutyl]N-[(3-methylbutyl)] amine, mp 130°–132° C. and MH* 385. This amine (400 mg, 1.04 mmol) was then reacted with tert-butylisocyanate (110 mg, 1.11 mmol) to afford 500 mg (100%) of [2(R), 3(S)]-N-[[3-(phenylmethylcarbamoyl)amino]- 2-hydroxy-4-phenyl]-1-[(3-methylbutyl)]amino-1-(1,1-dimethylethy)amino] carbonyl]butane; as an oil, MH$^+$484.

b) The CBZ protected compound (530 mg, 1.10 mmol) was then deprotected by hydrogenation over 10% palladium-on-carbon and the resulting free amine coupled with N-CBZ-L-asparagine (377 mg, 1.42 mmol) in the presence of N-hydroxybenzotriazole (290 mg, 2.15 mmol) and EDC (300 mg, 1.56 mmol) to yield 430 mg (53%) of [1S-[1R*(R*), 2S*]]-N$^1$[3 [[[(1,1-dimethylethyl)amino]carbonyl](3-methylbutyl)amino]- 2 -hydroxy-1-(phenylmethyl)propyl]-2[ (phenylmethylcarbamoyl)amino]- butanediamide, mp 148°–151° C. (dec) and MH$^+$598. This compound (370 mg, 0.619 mmol) was then deprotected by hydrogenation over 10% palladium-on-carbon and the resulting free amine coupled with 2-quinolinecarboxylic acid N-hydroxy-succinimide ester (193 mg, 0.714 mmol), in the presence of N-methylmorpholine, to afford 310 mg (70%) of pure [1S-[1R*(R*), 2S*]]-N$^1$[3-[[[(1,1-dimethylethyl)amino] carbonyl](3-methylbutyl)amino]-2-hydroxy-1-(phenylmethyl) propyl]-2-[(2-quinolinylcarbonyl) amino]-butanediamide; mp 93.5°–95.5° C. and MH$^+$619.

EXAMPLE 3

The procedure described in Example 1, part C-H, was used to prepare [1S-[1R*(R*), 2S*]]-N$^1$[3-[ [[(1,1-dimethylethyl)amino]carbonyl]- 2-napthylmethyl)amino]-2-hydroxy- 1-(phenylmethyl)propyl]-2-[(2-quinolinylcarbony-l)amino]-butanediamide.

a) From the reaction of 1.80 g (6.05 mmol) of N-benzyloxycarbonyl 3(S)-amino-1,2-(S)-epoxy-4-phenylbutane and 1.15 g (7.31 mmol) of 2-(aminomethyl) naphthalene, one obtains 2.11 g (77%) of [2(R), 3(S)]-N-[[3-(phenylmethylcarbamoyl) amino]-2-hydroxy-4-phenylbutyl]N-[(2-napthylmethyl)]amine, MH$^+$455. This amine (366.8 mg, 0.807 mmol) was then reacted with tert-butylisocyanate (66.4 mg, 0.67 mmol) to afford 350.0 mg (94%) of [2(R), 3(S)]-N-[ [3-(phenylmethylcarbamoyl)amino]-2-hydroxy-4-phenyl]-1-[ (2-napthylmethyl)]amino-1-(1,1-dimethylethyl) amino]carbonyl]butane; as an oil, MH+554.

b) The CBZ protected compound (330 mg, 0.596 mmol) was then deprotected by hydrogenation over 10% palladium-on-carbon and the resulting free amine coupled with N-CBZ-L-asparagine (165.1 mg, 0.62 mmol) in the presence of N-hydroxybenzotriazole (142.3 mg, 0.93 mmol) and EDC (130.7 mg, 0.68 mmol) to yield 161.7 mg (41%) of [1S-[1R*(R*), 2S*]]N $^1$[3-[[[(1,1-dimethylethyl)amino]carbonyl](2-napthylmethyl)amino]- 2-hydroxy-1-(phenylmethyl)propyl]-2[(phenylmethylcarbamoyl)amino]-butanediamide; mp 151°–152° C. (dec) and MH$^+$668. This compound (91.0 mg, 0.136 mmol) was then deprotected by hydrogenation over 10% palladium-on-carbon and the resulting free amine coupled with 2-quinolinecarboxylic acid N-hydroxysuccinimide ester (36.8 mg, 0.136 mmol), in the presence of N-methylmorpholine, to afford 65.8 mg (70%) of pure [1S-[1R*(R*), 2S*]]-N$^1$[3-[[[(1,1-dimethylethyl)amino]carbonyl] (2-napthylmethyl)amino]-2-hydroxy- 1-(phenylmethyl)propyl]-2-[(2-quinolinylcarbonyl) amino]-butanediamide; mp 119°–120° C. and MH$^+$689.

EXAMPLE 4

The procedure described in Example 1, part C-H, was used to prepare [1S-[1R*(R*), 2S*]]-N$^1$[3-[[[(1,1-dimethylethyl) amino]carbonyl](2-phenylethyl)amino]-2-hydroxy-1-(phenylmethyl) propyl]-2-[(2-quinolinylcarbonyl)amino]-butanediamide.

a) From the reaction of 1.00 g (3.36 mmol) of N-benzyloxycarbonyl 3(S)-amino-1,2-(S)-epoxy-4-phenylbutane and 8.19 g (67.0 mmol) of 2-phenethyl amine, one obtains 1.10 g (79%) of [2 (R), 3 (S) ]-N-[[3-(phenylmethylcarbamoyl)amino]-2-hydroxy- 4-phenylbutyl]N-[(2-phenylethyl)] amine, mp 137°–138° C. and MH$^+$419. This amine (750 mg, 1.79 mmol) was then reacted with tert-butylisocyanate (178 mg, 1.79 mmol) to afford 897 mg •(97%) of [2(R), 3(S)]-N-[[3-(phenylmethylcarbamoyl)amino]- 2-hydroxy-4-phenyl]-1-[(2-phenylethyl)]amino-1-(1,1-dimethylethyl)amino] carbonyl]butane; as an oil, MH$^+$518.

b) The CBZ protected compound (897 mg, 1.73 mmol) was then deprotected by hydrogenation over 10% palladium-on-carbon and the resulting free amine coupled with N-CBZ-L-asparagine (620.7 mg, 2.33 mmol) in the presence of N-hydroxybenzotriazole (509.5 mg, 3.33 mmol) and EDC (488.0 mg, 2.55 mmol) to yield 1.00 g (92%) of [1S-[1R*(R*), 2S*]]-N $^1$[3[[[(1,1-dimethylethyl)amino]carbonyl](2-phenylethyl) amino]-2-hydroxy-1-(phenylmethyl) propyl]-2-[ (phenylmethylcarbamoyl)amino]-butanediamide; mp 145° C. (dec) and MH$^+$632. This compound (860 mg, 1.36 mmol) was then deprotected by hydrogenation over 10% palladium-on-carbon and the resulting free amine coupled with 2-quinolinecarboxylic acid N-hydroxysuccinimide ester (338 mg, 1.25 mmol), in the presence of N-methylmorpholine, to afford 450.4 mg (55%)of pure [1S-[1R*(R*), 2S*]]-N$^1$[3[[[(1,1-dimethylethyl)amino]

carbonyl]( 2-phenylethyl)amino]-2-hydroxy-1-(phenylmethyl)propyl]-2-[(2-quinolinylcarbonyl)amino]-butanediamide; mp 139°–140° C. and MH⁺653.

EXAMPLE 5

The procedure described in Example 1, part C-H, was used to prepare [1S-[1R*(R*), 2S*]]-N¹[3-[[[(1,1-dimethylethyl)amino] carbonyl](2,2 -dimethylpropyl)amino]-2-hydroxy- 1-(phenylmethyl) propyl]-2 -[(2-quinolinylcarbonyl)amino]-butanediamide.

a) From the reaction of 1.00 g (3.36 mmol) of N-benzyloxycarbonyl 3(S)-amino-1,2-(S)-epoxy-4-phenylbutane and 7.9 mL (approx. 67 mmol) of neopentyl amine, one obtains 0.69 g (49%) of [2(R), 3(S)]-N-[[ 3-(phenylmethylcarbamoyl)amino]-2-hydroxy- 4-phenylbutyl]N[(2,2-dimethylpropyl)]amine, MH⁺385. This amine (686 mg, 1.78 mmol) was then reacted with tert-butylisocyanate (180 mg, 1.78 mmol) to afford 860 mg (100%) of [2(R), 3(S)]-N-[[3-(phenylmethylcarbamoyl)amino]- 2-hydroxy-4-phenyl]-1-[(2,2-dimethylpropyl)] amino-1-(1,1-dimethylethyl) amino] carbonyl]butane; MH⁺484.

b) The CBZ protected compound (860 mg, 1.78 mmol) was then deprotected by hydrogenation over 10% palladium-on-carbon and the resulting free amine coupled with N-CBZ-L-asparagine (471 mg, 1.77 mmol) in the presence of N-hydroxybenzotriazole (406 mg, 2.66 mmol) and EDC (374 mg, 1.95 mmol) to yield 326 mg (34%) of [1S-[R*(R*), 2S*]]-N¹[3-[ [[(1,1-dimethylethyl)amino]carbonyl](2,2-dimethylpropyl)amino]- 2-hydroxy-1-(phenylmethyl)propyl]-2-[ (phenylmethylcarbamoyl)amino]-butanediamide; mp 177°–178° C. and MH⁺598. This compound (245 mg, 0.41 mmol) was then deprotected by hydrogenation over 10% palladium-on-carbon and the resulting free amine coupled with 2-quinolinecarboxylic acid N-hydroxy- succinimide ester (111 mg, 0.41 mmol), in the presence of N-methylmorpholine, to afford 150 mg (59%) of pure [1S-[R*(R*), 2S*]]-N¹[3-[[[(1,1-dimethylethyl)amino] carbonyl](2,2-dimethylpropyl)amino]-2-hydroxy- 1-(phenylmethyl) propyl]-2-[(2-quinolinylcarbonyl)amino]-butanediamide; mp 115°–117° C. and MH⁺619.

EXAMPLE 6

The procedure described in Example 1, part C-H, was used to prepare [1S-[R*(R*), 2S*]]-N¹[3-[[[(1,1-dimethylethyl)amino]carbonyl]( 4-methoxyphenylmethyl)amino]-2-hydroxy-1-(phenylmethyl)propyl]-2-[(2-quinolinylcarbonyl)amino]-butanediamide;

a) From the reaction of 1.00 g (3.36 mmol) of N-benzyloxycarbonyl 3(S) -amino-1,2-(S)-epoxy-4-phenylbutane and 9.2 g (67 mmol) of 4-methoxybenzyl amine, one obtains 1.12 g (76%) of [2 (R), 3(S)]-N-[[3-(phenylmethylcarbamoyl)amino]- 2-hydroxy-4-phenylbutyl]N-[(4-methoxyphenylmethyl)] amine, MH⁺435. This amine (1.12 g, 2.58 mmol) was then reacted with tert-butylisocyanate (260 mg, 2.58 mmol) to afford 1.35 g (98%) of [2(R), 3(S)]-N-[[3-(phenylmethylcarbamoyl)amino]- 2-hydroxy-4-phenyl]-1-[(4-methoxyphenylmethyl)]amino- 1-(1,1-dimethylethyl)amino]carbonyl]butane; MH⁺534.

b) The CBZ protected compound (1.35 g, 2.53 mmol) was then deprotected by hydrogenation over 10% palladium-on-carbon and the resulting free amine coupled with N-CBZ-L-asparagine (684 mg, 2.57 mmol) in the presence of N-hydroxybenzotriazole (590 mg, 3.85 mmol) and EDC (543 mg, 2.83 mmol) to yield 442 mg (29%) of [1S-[1R*(R*), 2S*]]N ¹[3-[[[(1,1-dimethylethyl)amino]carbonyl](4-methoxyphenylmethyl)amino]- 2-hydroxy-1-(phenylmethyl)propyl]- 2-[phenylmethylcarbamoyl)amino] butanediamide; mp 175° C. (dec) and MH⁺648. This compound (345 mg, 0.53 mmol) was then deprotected by hydrogenation over 10% palladium-on-carbon and the resulting free amine coupled with 2-quinolinecarboxylic acid N-hydroxy-succinimide ester (118 mg, 0.44 mmol), in the presence of N-methylmorpholine, to afford 108 mg (31%) of pure [1S-[1R* (R*), 2S*]]-N¹[3-[ [[(1,1-dimethylethyl)amino]carbonyl](4-methoxyphenylmethyl)amino]- 2-hydroxy-1-(phenylmethyl)propyl]- 2-[(2-quinolinylcarbonyl)amino]-butanediamide; mp 220° C. (dec) and MLi⁺675.

EXAMPLE 7

The procedure described in Example 1, part C-H, was used to prepare [1S-[1R* (R*), 2S*]-N¹[3-[[[(1,1-dimethylethyl)amino] carbonyl](n-butyl)amino]-2-hydroxy-1-(phenylmethyl)propyl]- 2-[(2-quinolinylcarbonyl)amino] butanediamide.

a) From the reaction of 1.48 g (5.0 mmol) of N-benzyloxycarbonyl 3(S)-amino-1,2-(S)-epoxy-4-phenylbutane and 7.314 g (100.0 mmol) of n-butyl amine, one obtains 1.50 g (80%) of [2(R), 3(S)]-N-[[3-(phenylmethylcarbamoyl)amino]-2-hydroxy- 4-phenylbutyl]N-[(n-butyl)]amine. This amine (1.48 g, 4.0 mmol) was then reacted with tert-butylisocyanate (396 mg, 4.0mol) to afford 1.87 g (100%) of [2(R), 3(S)]-N-[[3-(phenylmethylcarbamoyl)amino]- 2-hydroxy-4-phenyl]-1-[(n-butyl)]amino- 1-(1,1-dimethylethyl)amino]carbonyl]butane as an oil.

b) The CBZ protected compound (1.87 g, 4.0 mmol) was then deprotected by hydrogenation over 10% palladium-on-carbon and the resulting free amine coupled with N-CBZ-L-asparagine (1.05 g, 3.96 mmol) in the presence of N-hydroxybenzotriazole (535 mg, 7.9 mmol) and EDC (759 mg, 3.96 mmol) to yield 1.75 g (76%) of [1S-[1R*(R*), 2S*]]-N¹[3-[ [[(1,1-dimethylethyl)amino]carbonyl](n-butyl)amino]-2-hydroxy- 1-(phenylmethyl)propyl]-2-[ (phenylmethylcarbamoyl)amino]-butanediamide; mp 166°–167° C. and MH⁺584.

EXAMPLE 8

The procedure described in Example 1, part C-H, was used to prepare [1S-[1R*(R*), 2S*]]-N¹[3-[[[(1,1-dimethylethyl)amino] carbonyl](phenylmethyl)amino]-2-hydroxy-1-(phenylmethyl) propyl]-2-[(2-quinolinylcarbonyl)amino] butanediamide.

a) From the reaction of 1.48 g (5.0 mmol) of N-benzyloxycarbonyl 3(S)-amino-1,2-(S)-epoxy-4-phenylbutane and 10.68 g (100.0 mmol) of benzyl amine, one obtains 1.88 g (95%) of [2 (R), 3 (S)]-N-[[3-(phenylmethylcarbamoyl)amino]-2-hydroxy- 4-phenylbutyl]N-[(phenylmethyl)] amine. This amine (1.88 g, 4.65 mol) was then reacted with tert-butylisocyanate (460.0 mg, 4.6 mmol) to afford 2.24 g (96%) of [2(R), 3(S)]-N[ [3-(phenylmethylcarbamoyl)amino]-2-hydroxy-4-phenyl]-1-[ (phenylmethyl)]amino-1-(1,1-dimethylethyl)amino]carbonyl]butane.

b) The CBZ protected compound (2.22 g, 4.4 mmol) was then deprotected by hydrogenation over 10% palladium-on-carbon and the resulting free amine coupled with N-CBZ-L-asparagine (1.17 g, 4.4 mmol) in the presence of N-hydroxybenzotriazole (1.19 g, 8.8mol) and EDC (843 mg, 4.4 mmol) to yield 2.11 g (78%) of [1S-[1R*(R*), 2S*]]-N¹[3[ [[(1,1-dimethylethyl)amino]carbonyl](phenylmethyl)amino]-2-hydroxy- 1-(phenylmethyl)propyl]-2-[ (phenylmethylcarbamoyl)amino]-butanediamide; mp 156°–158° C.

and MH+618. This compound (1.0 g, 1.62 mol) was then deprotected by hydrogenation over 10% palladium-on-carbon and the resulting free amine coupled with 2-quinolinecarboxylic acid N-hydroxysuccinimide ester (437 mg, 1.62 mmol), in the presence of N-methylmorpholine, to afford 640 mg (62%) of pure [1S-[1R*(R*), 2S*]]-N¹[3-[[[(1,1-dimethylethyl)amino] carbonyl](phenylmethyl)amino]-2-hydroxy- 1-(phenylmethyl) propyl]-2 -[(2 -quinolinylcarbonyl)amino]butanediamide; mp 110.5°–112.5° C. and MH+639.

EXAMPLE 9

Additional exemplary compounds of the present invention are listed in Table 1. These compounds were prepared according to the following general procedures.

General Procedure for the Synthesis of 1,3-Diamino 4-phenyl Butan-2-ol Derivatives A mixture of the amine $R^3NH_2$ (20 equiv.) in dry isopropyl alcohol (20 mL/mmol of epoxide to be converted) was heated to reflux and then treated with an N-Cbz amino epoxide of the formula:

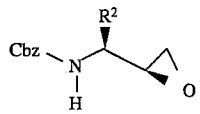

from a solids addition funnel over a 10–15 minute period. After the addition is complete the solution was maintained at reflux for an additional 15 minutes and the progress of the reaction monitored by TLC. The reaction mixture was then concentrated in vacuo to give an oil that was treated with n-hexane with rapid stirring whereupon the ring opened material precipitated from solution. Precipitation was generally complete within 1 hr and the product was then isolated by filtration on a Büchner funnel and then air dried. The product was further dried in vacuo. This method affords amino alcohols of sufficient purity for most purposes.

General Procedure for the Synthesis of Amino Epoxides

The amino epoxides can be prepared as shown in the previous example. Preferably, such amino epoxides are prepared utilizing the following procedure.

Step A

A solution of L-phenylalanine (50.0 g, 0.302 mol), sodium hydroxide (24.2 g, 0.605 mol) and potassium carbonate (83.6 g, 0.605 mol) in water (500 ml) is heated to 97° C. Benzyl bromide (108.5 ml, 0.912 mol) is then slowly added (addition time ~25 min). The mixture is then stirred at 97° C. for 30 minutes. The solution is cooled to room temperature and extracted with toluene (2×250 ml). The combined organic layers are then washed with water, brine, dried over magnesium sulfate, filtered and concentrated to give an oil product. The crude product is then used in the next step without purification.

Step B

The crude benzylated product of the above step is dissolved in toluene (750 ml) and cooled to –55° C. A 1.5 M solution of DIBAL-H in toluene (443.9 ml, 0.666 mol) is then added at a rate to maintain the temperature between –55° to –50° C. (addition time ~1 hour). The mixture is stirred for 20 minutes at –55° C. The reaction is quenched at –55° C. by the slow addition of methanol (37 ml). The cold solution is then poured into cold (5° C.) 1.5 N HCl solution (1.8 L). The precipitated solid (approx. 138 g) is filtered off and washed with toluene. The solid material is suspended in a mixture of toluene (400 ml) and water (100 ml). The mixture is cooled to 5° C., treated with 2.5 N NaOH (186 ml) and then stirred at room temperature until the solid is dissolved. The toluene layer is separated from the aqueous phase and washed with watr and brine, dried over magnesium sulfate, filtered and concentrated to a volume of 75 ml (89 g). Ethyl acetate (25 ml) and hexane (25 ml) are then added to the residue upon which the alcohol product begins to crystallize. AFter 30 min., an additional 50 ml hexane is added to promote further crystallization. The solid is filtered off and washed with 50 ml hexane to give approximately 35 g of material. A second crop of matrial can be isolated by refiltering the mother liquor. The solids are combined and recrystallized from ethyl acetate (20 ml) and hexane (30 ml) to give, in 2 crops, approximately 40 g (40% from L-phenylalanine) of analytically pure alcohol product. The mother liquors are combined and concentrated (34 g). The residue is treated with ethyl acetate and hexane which profides an additional 7 g (~7% yield) of slightly impure solid product. Further optimization in the recovery from the mother liquor is probable.

Step C

A solution of oxalyl chloride (8.4 ml, 0.096 mol) in dichloromethane (240 ml) is cooled to –74° C. A solution of DMSO (12.0 ml, 0.155 mol) in dichloromethane (50 ml) is then slowly added at a rate to maintain the temperature at –74° C. (addition time ~1.25 hr). The mixture is stirred for 5 min. followed by addition of a solution of the alcohol (0.074 mol) in 100 ml of dichloromethane (addition time ~20 min., temp. –75° C. to –68° C.). The solution is stirred at –78° C. for 35 minutes. Triethylamine (41.2 ml, 0.295 mol) is then added over 10 min. (temp. –78° to –68° C.) upon which the ammonium salt procipitated. The cold mixture is stirred for 30 min. and then water (225 ml) is added. The dichloromethane layer is separated from the aqueous phase and washed with water, brine, dried over magnesium sulfate, filtered and concentrated. The residue is diluted with ethyl acetate and hexane and then filtered to further remove the ammonium salt. The filtrate is concentrated to give the desired aldehyde product. The aldehyde was carried on to the next step without purification.

Temperatures higher than –70° C. has been reported in the literature for the Swern oxidation. Other Swern modifications and alternatives to the Swern oxidations are also possible.

A solution of the crude aldehyde 0.074 mol and chloroiodomethane (7.0 ml, 0.096 mol) in tetrahydrofuran (285 ml) is cooled to –78° C. A 1.6 M solution of n-butyllithium in hexane (25 ml, 0.040 mol) is then added at a rate to maintain the temperature at –75° C. (addition time ~15 min.). After the first addition, additional chloroiodomethane (1.6 ml, 0.022 mol) is added again, followed by n-butyllithium (23 ml, 0.037 mol), keeping the temperature at –75° C. The mixture is stirred for 15 min. Each of the reagents, chloroiodomethane (0.70 ml, 0.010 mol) and n-butyllithium (5 ml, 0.008 mol) are added 4 more times over 45 min. at –75° C. The cooling bath is then removed and the solution warmed to 22° C. over 1.5 hr. The mixture is poured into 300 ml of saturated aq. ammonium chloride solution. The tetrahydrofuran layer is separated. The aqueous phase is extracted with ethyl acetate (1×300 ml). The combined organic layers are washed with brine, dried over magnesium sulfate, filtered and concentrated to give a brown oil (27.4 g). The product could be used in the next step without purification. The desired diastereomer can be purified by recrystallization at a subsequent step.

Alternately, the product could be purified by chromatography.

General procedure for the Reaction of Amino Alcohols with Isocyanates: Preparation of Ureas A solution from the amino alcohol in tetrahydrofuran (THF) was treated at room temperature with the appropriate isocyanate of formula $R^4NCO$ via syringe under nitrogen. After the reaction has stirred for ~5 m the progress of the reaction was monitored by TLC. The solvent was removed in vacuo and the product obtained was of sufficient purity for most purposes. The product may be further purified by dissolution in ethyl acetate and washing with 5% aqueous citric acid, water, and brine. The solvent is dried over anhydrous magnesium sulfate, filtered and concentrated in vacuo to give the pure urea.

General Procedure for the Removal of the Protecting Grooms by Hydrogenolysis with Palladium on Carbon A. Alcohol Solvent The Cbz-protected peptide derivative was dissolved in methanol (ca.20 mL/mmol) and 10% palladium on carbon catalyst is added under a nitrogen atmosphere. The reaction vessel is sealed and flushed 5 times with nitrogen and then 5 times with hydrogen. The pressure is maintained at 50 psig for 1–16 hours and then the hydrogen replaced with nitrogen and the solution filtered through a pad of celite to remove the catalyst. The solvent is removed in vacuo to give the free amino derivative of suitable purity to be taken directly on to the next step.

B. Acetic Acid Solvent

The Cbz-protected peptide derivative was dissolved in glacial acetic acid (20 mL/mmol) and 10% palladium on carbon catalyst is added under a nitrogen atmosphere. The reaction vessel is flushed 5 times with nitrogen and 5 times with hydrogen and then maintained at 40 psig for about 2 h. The hydrogen was then replaced with nitrogen and the reaction mixture filtered through a pad of celite to remove the catalyst. The filtrate was concentrated and the resulting product taken up in anhydrous ether and evaporated to dryness 3 times. The final product, the acetate salt, was dried in vacuo and is of suitable purity for subsequent conversion.

General Procedure for Removal of Boc-protecting Group with 4N Hydrochloric Acid in Dioxane The Boc-protected amino acid or peptide is treated with a solution of 4N HCl in dioxane with stirring at room temperature. Generally the deprotection reaction is complete within 15 minutes, the progress of the reaction is monitored by thin layer chromatography (TLC). Upon completion, the excess dioxane and HCl are removed by evaporation in vacuo. The last traces of dioxane and HCl are best removed by evaporation again from anhydrous ether or acetone. The hydrochloride salt thus obtained is thoroughly dried in vacuo and is suitable for further reaction.

EDC/HOBt Coupling of Cbz-Asparagine (General Procedure)

N-CBZ-(L-asparagine (1.10eq) and N-hydroxybenzotriazole (HOBt) (1.5eq) are dissolved in dry dimethylformamide (DMF) (2–5 mL/mmol) and cooled in an ice bath. 1-(3-dimethylaminopropyl)-3-ethylcarbodiimide hydrochloride (EDC) (1.10eq) is added to the stirring solution and maintained at 0° C. for 10 minutes. A solution of the amino component (free amine), 1.0 eq in DMF (1–2 mL/mmol), is added. [In the case of the amine hydrochloride or acetate salt, an equivalent of N-methylmorpholine is also added.] The reaction mixture is stirred at 0° C. for 1 hour and then at room temperature for ~5–6 hours. The reaction mixture is then poured into a rapidly stirring solution of 60% saturated aqueous sodium bicarbonate (ca-50 mL/mmol). An immediate white precipitate forms which is collected on a Büchner funnel and the solid washed thoroughly with saturated aqueous sodium bicarbonate, water, 5% aqueous citric acid solution and water. The product is thoroughly dried in vacuo and redissolved in DMF, filtered and reprecipitated by the addition to water. The precipitated product is isolated by filtration, washed again with water and dried in vacuo.

General Procedure for Acylation with 2-Quinoline Carboxylic Acid N-Hydroxysuccinimide Ester A solution of the free amine (or amine acetate salt) and 1.0 equivalent of N-hydroxysuccinimide 2-quinoline carboxylate in anhydrous dichloromethane was treated with 1.5 equivalents of N-methylmorpholine (NMM) at room temperature. The progress of the reaction was monitored by TLC and when the reaction was complete the reaction mixture was diluted with additional dichloromethane and the solution washed with saturated aqueous sodium bicarbonate, 5% aqueous citric acid, water and brine. The solution was dried over anhydrous magnesium sulfate, filtered and concentrated in vacuo. The product thus obtained was recrystallized from a mixture of acetone and hexane.

TABLE 1

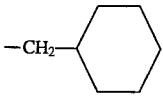

| Entry No. | R | R³ | R⁴ |
|---|---|---|---|
| 1 | Cbz[a] | CH₃ | n-Butyl |
| 2 | Cbz | i-Butyl | CH₃ |
| 3 | Cbz | i-Butyl | n-Butyl |
| 4 | Q[b] | i-Butyl | n-Butyl |
| 5 | Cbz | i-Propyl | n-Butyl |
| 6 | Q | i-Propyl | n-Butyl |
| 7 | Cbz | C₆H₅ | n-Butyl |
| 8 | Cbz | —CH₂-cyclohexyl | n-Butyl |
| 9 | Cbz | —CH₂-phenyl | n-Butyl |
| 10 | Q | —CH₂-phenyl | n-Butyl |
| 11 | Cbz | cyclohexyl | n-Butyl |
| 12 | Cbz | i-Butyl | n-Propyl |
| 13 | Cbz | i-Butyl | —CH₂CH(CH₃)₂ |
| 14 | Cbz | (R)—CH(CH₃)-phenyl | n-Butyl |
| 15 | Cbz | —CH₂-cyclohexyl | i-Propyl |
| 16 | Cbz | —CH₂-cyclohexyl | —CH₂CH₂CH(CH₃)₂ |
| 17 | Cbz | i-Butyl | —CH₂CH₃ |
| 18 | Cbz | i-Butyl | —CH(CH₃)₂ |
| 19 | Cbz | i-Butyl | —CH₂-cyclohexyl |
| 20 | Q | i-Butyl | —CH₂-cyclohexyl |
| 21 | Cbz | —CH₂-cyclohexyl | —(CH₂)₂CH(CH₃)₂ |

TABLE 1-continued

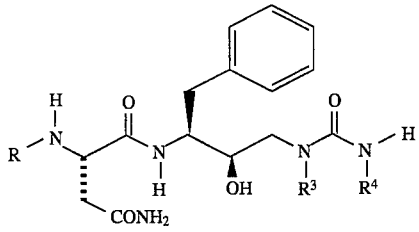

| Entry No. | R | R³ | R⁴ |
|---|---|---|---|
| 22 | Cbz | (CH₂)₂CH(CH₃)₂ | —CH(CH₃)₂ |
| 23 | Q | i-Butyl | —CH(CH₃)₂ |
| 24 | Cbz | i-Butyl | —C(CH₃)₃ |
| 25 | Q | i-Butyl | —C(CH₃)₃ |
| 26 | Cbz | —CH₂-(2-naphthyl) | —C(CH₃)₃ |
| 27 | Q | —CH₂-(2-naphthyl) | —C(CH₃)₃ |
| 28 | Cbz | —(CH₂)₂CH(CH₃)₂ | —C(CH₃)₃ |
| 29 | Q | —(CH₂)₂CH(CH₃)₂ | —C(CH₃)₃ |
| 30 | Cbz | —CH₂C₆H₅ | —C(CH₃)₃ |
| 31 | Q | —CH₂C₆H₅ | —C(CH₃)₃ |
| 32 | Cbz | —(CH₂)₂C₆H₅ | —C(CH₃)₃ |
| 33 | Cbz | —(CH₂)₂C₆H₅ | —C(CH₃)₃ |
| 34 | Cbz | n-Butyl | —C(CH₃)₃ |
| 35 | Cbz | n-Pentyl | —C(CH₃)₃ |
| 36 | Cbz | n-Hexyl | —C(CH₃)₃ |
| 37 | Cbz | —CH₂-C₆H₅ | —C(CH₃)₃ |
| 38 | Cbz | —CH₂C(CH₃)₃ | —C(CH₃)₃ |
| 39 | Q | —CH₂C(CH₃)₃ | —C(CH₃)₃ |
| 40 | Cbz | —CH₂CH₂—N(morpholino) | —C(CH₃)₃ |
| 41 | Cbz | —CH₂C₆H₅OCH₃ (para) | —C(CH₃)₃ |
| 42 | Cbz | —CH₂-(3-pyridyl) | —C(CH₃)₃ |
| 43 | Cbz | —CH₂-(4-pyridyl) | —C(CH₃)₃ |
| 44 | Cbz | —(CH₂)₂C(CH₃)₃ | —C(CH₃)₃ |
| 45 | Q | —(CH₂)₂C(CH₃)₃ | —C(CH₃)₃ |
| 46 | Cbz | —(CH₂)₄OH | —C(CH₃)₃ |
| 47 | Q | —(CH₂)₄OH | —C(CH₃)₃ |
| 48 | Q | —CH₂-C₆H₄-F | —C(CH₃)₃ |

TABLE 1-continued
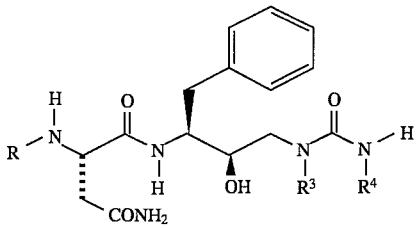
| Entry No. | R | R³ | R⁴ |
|---|---|---|---|
| 49 | Q | 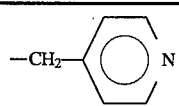 —CH₂— | —C(CH₃)₃ |
| 50 |  | —CH₂CH(CH₃)₂ | —C(CH₃)₃ |
| 51 | 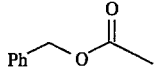 | —CH₂CH(CH₃)₂ | —C(CH₃)₃ |
| 52 | 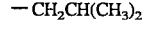 | —CH₂CH(CH₃)₂ | —C(CH₃)₃ |
| 53 |  | —CH₂CH(CH₃)₂ | —C(CH₃)₃ |
| 54 | 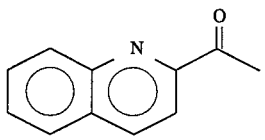 | —CH₂CH(CH₃)₂ | —C(CH₃)₃ |
| 55 | 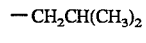 | —CH₂CH(CH₃)₂ | —C(CH₃)₃ |
| 56 |  | —CH₂CH(CH₃)₂ | —C(CH₃)₃ |
| 57 |  | —CH₂CH(CH₃)₂ | —C(CH₃)₃ |
| 58 | 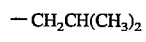 | —CH₂CH(CH₃)₂ | —C(CH₃)₃ |

TABLE 1-continued
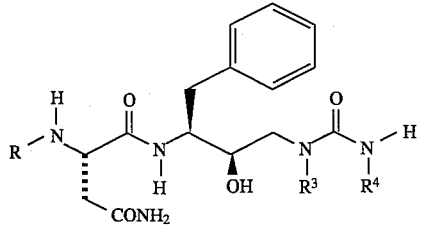
| Entry No. | R | R³ | R⁴ |
|---|---|---|---|
| 59 | 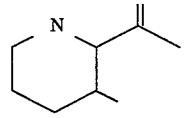 | —CH₂CH(CH₃)₂ | —C(CH₃)₃ |
| 60 | 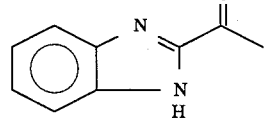 | —CH₂CH(CH₃)₂ | —C(CH₃)₃ |
| 61 | 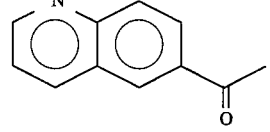 | —CH₂CH(CH₃)₂ | —C(CH₃)₃ |
| 62 | 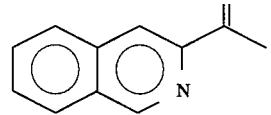 | —CH₂CH(CH₃)₂ | —C(CH₃)₃ |
| 63 | 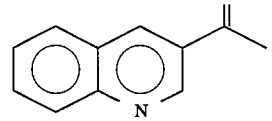 | —CH₂CH(CH₃)₂ | —C(CH₃)₃ |
| 64 | 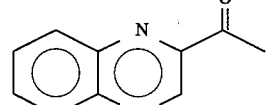 | —CH₂CH(CH₃)₂ | —C(CH₃)₃ |
| 65 | 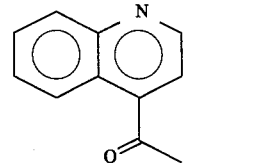 | —CH₂CH(CH₃)₂ | —C(CH₃)₃ |
| 66 | 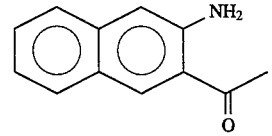 | —CH₂CH(CH₃)₂ | —C(CH₃)₃ |

TABLE 1-continued

[Structure: R-NH-CH(CH2CONH2)-C(O)-NH-CH(CH2Ph)-CH(OH)-CH2-N(R3)-C(O)-NH-R4]

| Entry No. | R | R³ | R⁴ |
|---|---|---|---|
| 67 | 1-acyl-isoquinoline (attached via carbonyl) | —CH₂CH(CH₃)₂ | —C(CH₃)₃ |
| 68 | 2-aminophenyl ketone (o-NH₂-C₆H₄-C(O)—) | —CH₂CH(CH₃)₂ | —C(CH₃)₃ |
| 69 | 1-hydroxy-2-naphthoyl (1-OH-naphthyl-2-C(O)—) | —CH₂CH(CH₃)₂ | —C(CH₃)₃ |

ᵃbenzyloxycarbonyl
ᵇ2-quinolinylcarbonyl

EXAMPLE 10

Following the generalized procedures set forth in Example 9, the compounds set forth in Table 2 were prepared.

TABLE 2

[Structure: A-NH-CH(CH2Ph)-CH(OH)-CH2-N(R3)-C(O)-NH-R4]

| Entry | A | R³ | R⁴ |
|---|---|---|---|
| 1 | Cbz—Val | i-amyl | tBu |
| 2 | Cbz—Leu | i-amyl | t-Bu |
| 3 | Cbz—Ile | i-amyl | t-Bu |
| 4 | Ac-D-homo-Phe | i-Bu | n-Bu |
| 5 | Qui-Orn (γ-Cbz) | —CH₂—C₆H₅ | t-Bu |
| 6 | Cbz—Asn | —CH₂CH=CH₂ | t-Bu |
| 7 | Acetyl-t-BuGly | i-amyl | t-Bu |
| 8 | Acetyl-Phe | i-amyl | t-Bu |
| 9 | Acetyl-Ile | i-amyl | t-Bu |
| 10 | Acetyl-Leu | i-amyl | t-Bu |
| 11 | Acetyl-His | i-amyl | t-Bu |
| 12 | Acetyl-Thr | i-amyl | t-Bu |
| 13 | Acetyl-NHCH(C(CH₃)₂(SCH₃))C(O)— | i-amyl | t-Bu |

TABLE 2-continued

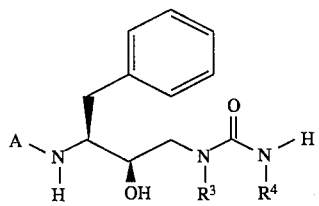

| Entry | A | R³ | R⁴ |
|---|---|---|---|
| 14 | Cbz—Asn | i-amyl | t-Bu |
| 15 | Cbz—Ala | i-amyl | t-Bu |
| 16 | Cbz—Ala | i-amyl | t-Bu |
| 17 | Cbz-beta-cyanoAla | i-amyl | t-Bu |
| 18 | Cbz-t-BuGly | i-amyl | t-Bu |
| 19 | Q-t-BuGly | i-amyl | t-Bu |
| 20 | Q—SCH₃Cys | i-amyl | t-Bu |
| 21 | Cbz—SCH₃Cys | i-amyl | t-Bu |
| 22 | Q—Asp | i-amyl | t-Bu |
| 23 | Cbz—(NHCH(C(CH₃)₂(SCH₃))C(O) | i-amyl | t-Bu |
| 24 | Cbz—EtGly | i-amyl | t-Bu |
| 25 | Cbz—PrGly | i-amyl | t-Bu |
| 26 | Cbz—Thr | i-amyl | t-Bu |
| 27 | Q—Phe | i-amyl | t-Bu |
| 28 | Cbz—Phe | i-amyl | t-Bu |
| 29 | Cbz[NHCH(CH₂C(O)NHCH₃)C(O) | i-amyl | t-Bu |
| 30 | Q[NHCH(CH₂C(O)NHCH₃)C(O) | i-amyl | t-Bu |

EXAMPLE 11

Following the generalized procedure of Example 9, the compounds listed in Table 3 were prepared.

TABLE 3

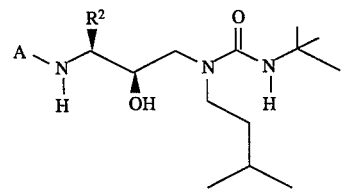

| Entry | R¹ |
|---|---|
| 1 | —CH₂SO₂CH₃ |
| 2 | (R)—CH(OH)CH₃ |
| 3 | —CH(CH₃)₂ |
| 4 | —(R,S)CH₂SOCH₃ |
| 5 | —CH₂SO₂NH₂ |
| 6 | —CH₂SCH₃ |
| 7 | —CH₂CH(CH₃)₂ |
| 8 | —CH₂CH₂C(O)NH₂ |
| 9 | (—S)—CH(OH)CH₃ |
| 10 | —CH₂C≡CH |
| 11 | —CF₃ |
| 12 | —CH(CF₃)₂ |
| 13 | —C(CH₃)₂(SCH₃) |

EXAMPLE 12

Following the generalized procedures of Example 9, the compounds set forth in Table 4 were prepared.

TABLE 4

| Entry | R² | A |
|---|---|---|
| 1 | n-Bu | Cbz—Asn |
| 2 | cyclohexylmethyl | Cbz—Asn |
| 3 | n-Bu | Boc |
| 4 | n-Bu | Cbz |
| 5 | C₆H₅CH₂ | Boc |
| 6 | C₆H₅CH₂ | Cbz |
| 7 | C₆H₅CH₂ | benzoyl |
| 8 | cyclohexylmethyl | Cbz |
| 9 | n-Bu | Q—Asn |
| 10 | cyclohexylmethyl | Q—Asn |
| 11 | C₆H₅CH₂ | Cbz—Ile |
| 12 | C₆H₅CH₂ | Q—Ile |
| 13 | C₆H₅CH₂ | Cbz—t-BuGly |
| 14 | C₆H₅CH₂ | Q—t-BuGly |
| 15 | C₆H₅CH₂ | Cbz—Val |
| 16 | C₆H₅CH₂ | Q—Val |
| 17 | 2-naphthylmethyl | Cbz—Asn |
| 18 | 2-naphthylmethyl | Q—Asn |
| 19 | 2-naphthylmethyl | Cbz |
| 20 | n-Bu | Cbz—Val |
| 21 | n-Bu | Q—Val |
| 22 | n-Bu | Q—Ile |
| 23 | n-Bu | Cbz—t-BuGly |
| 24 | n-Bu | Q—t-BuGly |
| 25 | p-F(C₆H₄)CH₂ | Q—Asn |
| 26 | p-F(C₆H₄)CH₂ | Cbz |
| 27 | p-F(C₆H₄)CH₂ | Cbz—Asn |
| 28 | C₆H₅CH₂ | Cbz-propargylglycine |
| 29 | C₆H₅CH₂ | Q-propargylglycine |
| 30 | C₆H₅CH₂ | acetyl-propargylglycine |
| 31 | i-Bu | Cbz—Asn |

EXAMPLE 13

The compounds listed in Table 5 were prepared according to the generalized procedures of Example 9.

TABLE 5

| Entry | X(H)R[4] | A |
|---|---|---|
| 1 | —NH$^t$Bu | Cbz—Asn |
| 2 | —NEt$_2$ | Cbz |
| 3 | —NHC(CH$_3$)$_2$CH$_2$CH$_3$ | Cbz |

EXAMPLE 14

The compounds of Table 6 were prepared according to the generalized procedures set forth in Example 9 except that instead of an isocyanate, an isothiocyanate equivalent was utilized.

TABLE 6

| Entry | XHR[4] |
|---|---|
| 1 | NHEt |
| 2 | NH$^t$Bu |

The Cbz group of the compounds shown in Examples 13 and 14 can be removed as described in Example 9 and the resulting compound can be coupled to a desired α- or β-amino acid or the like to produce compounds of the present invention.

EXAMPLE 15

The compounds shown in Table 7 were prepared according to the following general procedure. This general procedure represents a Curtius Rearrangement and reaction with the amino alcohol derivative as prepared following the general procedure in Example 9.

To a solution of 1 mmol of carboxylic acid in 12 mL of toluene and 3 mmol of triethylamine at 90° C. under a nitrogen atmosphere, was added 1 mmol of diphenylphosphoryl azide. After 1 hour, a solution of 1 mmol of amino alcohol derivative in 3.5 mL of either N,N-dimethylformamide or toluene was added. After 1 hour, the solvent was removed under reduced pressure, ethyl acetate and water added and the layers separated. The organic layer was washed with 5% citric acid, sodium bicarbonate, brine, dried, filtered and concentrated to afford the crude product. This was then recrystallized or chromatographed on silica gel to afford the purified final compound.

TABLE 7

| R[3] | R[4] |
|---|---|
| —CH$_2$CH(CH$_3$)$_2$ | —C(CH$_3$)$_2$ |
| —CH$_2$CH$_2$CH(CH$_3$)$_2$ | ◁ |
| —CH$_2$CH$_2$CH(CH$_3$)$_2$ | ◇ |
| —CH$_2$CH$_2$CH(CH$_3$)$_2$ | ⬠ |
| —CH$_2$CH$_2$CH(CH$_3$)$_2$ | ⬡ |

EXAMPLE 16

A. Preparation of 4(4-methoxybenzyl)itaconate

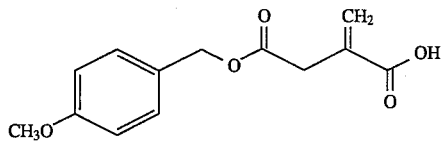

A 5 L three-necked round bottomed flask equipped with constant pressure addition funnel, reflux condenser, nitrogen inlet, and mechanical stirrer was charged with itaconic anhydride (660.8 g, 5.88 mol) and toluene (2300 mL). The solution was warmed to reflux and treated with 4-methoxybenzyl alcohol (812.4 g, 5.88 mol) dropwise over a 2.6h period. The solution was maintained at reflux for an additional 1.5 h and then the contents were poured into three 2 L erlenmeyer flasks to crystallize. The solution was allowed to cool to room temperature whereupon the desired monoester crystallized. The product was isolated by filtration on a Buchner funnel and air dried to give 850.2 g, 58% of material with mp 83°–85° C., a second crop, 17% was isolated after cooling of the filtrate in an ice bath. $^1$H NMR (CDCl$_3$) 300 MHz 7.32(d, J=8.7 Hz, 2H), 6.91(d, J=8.7 Hz, 2H), 6.49(s, 1H), 5.85(s, 1H), 5.12(s, 2H), 3.83(s, 3H), 3.40 (s, 2H).

B. Preparation of Methyl 4(4-methoxybenzyl)itaconate

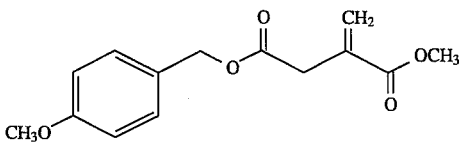

A 5 L three-necked round bottomed flask equipped with reflux condenser, nitrogen inlet, constant pressure addition funnel and mechanical stirrer was charged with 4(4-methoxybenzyl) itaconate (453.4 g, 1.81 mol) and treated with 1,5-diazabicyclo[4.3.0]non-5-ene (275.6 g, 1.81 mol), (DBN), dropwise so that the temperature did not rise above 15° C. To this stirring mixture was added a solution of methyl iodide (256.9 g, 1.81 mol) in 250 mL of toluene from the dropping funnel over a 45 m period. The solution was allowed to warm to room temperature and stirred for an additional 3.25 h.

The precipitated DBN hydroiodide was removed by filtration, washed with toluene and the filtrate poured into a separatory funnel. The solution was washed with sat. aq. NaHCO$_3$ (2×500 mL), 0.2N HCl (1×500 mL), and brine (2× 500 mL), dried over anhyd. MgSO$_4$, filtered, and the solvent removed in vacuo. This gave a clear colorless oil, 450.2 g, 94% whose NMR was consistent with the assigned structure. $^1$H NMR (CDCl$_3$) 300 MHz 7.30 (d, J=8.7 Hz, 2H), 6.90 (d, J=8.7 Hz, 2H), 6.34(s, 1H), 5.71(s, 1H), 5.09(s, 2H), 3.82(s, 3H), 3.73(s, 3H), 3.38(s, 2H). $^{13}$C NMR (CDCl$_3$) 170.46, 166.47, 159.51, 133.55, 129.97, 128.45, 127.72, 113.77, 66.36, 55.12, 51.94, 37.64.

C. Preparation of Methyl 4(4-methoxybenzyl) 2(R)-methylsuccinate

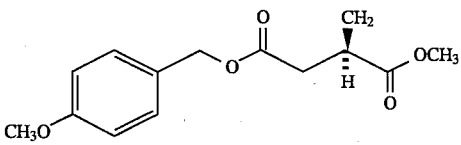

A 500 mL Fisher-Porter bottle was charged with methyl 4(4-methoxybenzyl) itaconate (71.1 g, 0.269 mol), rhodium (R, R) DiPAMP catalyst (204 mg, 0.269 mmol, 0.1 mol %) and degassed methanol (215 mL). The bottle was flushed 5 times with nitrogen and 5 times with hydrogen to a final pressure of 40 psig. The hydrogenation commenced immediately and after ca. 1 h the uptake began to taper off, after 3 h the hydrogen uptake ceased and the bottle was flushed with nitrogen, opened and the contents concentrated on a rotary evaporator to give a brown oil that was taken up in boiling/so-octane (ca. 200 mL, this was repeated twice), filtered through a pad of celite and the filtrate concentrated in vacuo to give 66.6 g, 93% of a clear colorless oil, $^1$H NMR (CDCl$_3$ 300 MHz 7.30(d, J=8.7 Hz, 2H), 6.91(d, J=8.7 Hz, 2H), 5.08(s, 2H), 3.82(s, 3H), 3.67(s, 3H), 2.95 (ddq, J=5.7, 7.5, 8.7 Hz, 1H), 2.79 (dd, J=8.1, 16.5 Hz, 1H), 2.45(dd, J=5.7, 16.5 Hz, 1H), 1.23(d, J=7.5 Hz, 3H).

D. Preparation Of Methyl 2 (R)-methylsuccinate

A 3 L three-necked round-bottomed flask equipped with a nitrogen inlet, mechanical stirrer, reflux condenser and constant pressure addition funnel was charged with methyl 4(4-methoxybenzyl) 2(R)-methylsuccinate (432.6 g, 1.65 mol) and toluene (1200 mL). The stirrer was started and the solution treated with trifluoroacetic acid (600 mL) from the dropping funnel over 0.25 h. The solution turned a deep purple color and the internal temperature rose to 45° C. After stirring for 2.25 h the temperature was 27° C. and the solution had acquired a pink color. The solution was concentrated on a rotary evaporator. The residue was diluted with water (2200 mL) and sat. aq. NaHCO$_3$ (1000 mL). Additional NaHCO$_3$ was added until the acid had been neutralized. The aqueous phase was extracted with ethyl acetate (2×1000 mL) to remove the by-products and the aqueous layer was acidified to pH=1.8 with conc. HCl. This solution was extracted with ethyl acetate (4×1000 mL), washed with brine, dried over anhyd. MgSO$_4$, filtered and concentrated on a rotary evaporator to give a colorless liquid 251 g, >100% that was vacuum distilled through a short path apparatus cut 1: bath temperature 120° C. @>1 mm, bp 25°–29° C.; cut 2: bath temperature 140° C. @0.5mm, bp 95°–108° C., 151 g, []$_D$@25° C.=+1.38° C. (c=15. 475, MeOH), [ α]$_D$=+8.48° C. (neat); cut 3: bath temperature 140° C., bp 108° C., 36 g, [α]$_D$ @ 25° C.=+1.49° C.(c= 15.00, MeOH), [α]$_D$=+8.98° C. (neat). Cuts 2 and 3 were combined to give 189 g, 78% of product, 1H NMR (CDCl$_3$) 300 MHz 11.6(brs, 1H), 3.72(s, 3H), 2.92(ddq, J=5.7, 6.9, 8.0 Hz, 1H), 2.81(dd, J=8.0, 16.8 Hz, 1H), 2.47(dd, J=5.7, 16.8 Hz, 1H), 1.26(d, J=6.9 Hz, 3H).

E. Preparation of Methyl Itaconate

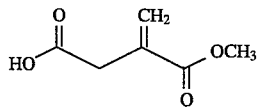

A 50 mL round bottomed flask equipped with reflux condenser, nitrogen inlet and magnetic stir bar was charged with methyl 4(4-methoxybenzyl) itaconate (4.00 g, 16 mmol). The solution was kept at room temperature for 18 hours and then the volatiles were removed in vacuo. The residue was taken up in ethyl acetate and extracted three times with saturated aqueous sodium bicarbonate solution. The combined aqueous extract was acidified to pH=1 with aqueous potassium bisulfate and then extracted three times with ethyl acetate. The combined ethyl acetate solution was washed with saturated aqueous sodium chloride, dried over anhydrous magnesium sulfate, filtered, and concentrated in vacuo. The residue was then vacuum distilled to give 1.23 g, 75% of pure product, bp 85–87 @0.1 mm. $^1$H NMR (CDCl$_3$) 300 MHz 6.34(s, 1H), 5.73(s, 2H), 3.76(s, 3H), 3.38(s, 2H). $^{13}$C NMR (CDCl$_3$) 77.03, 166.65, 129.220, 132.99, 52.27, 37.46.

F. Curtius Rearrangement of Methyl 2(R)-methylsuccinate:

Preparation Of Methyl N-MOz-α-methyl β-alanine.

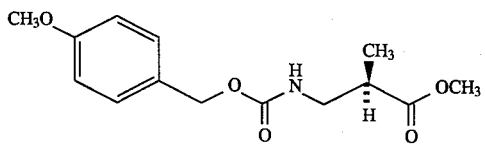

A 5L four necked round bottomed flask equipped with a nitrogen inlet, reflux condenser, mechanical stirrer, constant pressure addition funnel, and thermometer adapter was charged with methyl 2(R)-methylsuccinate (184.1 g, 1.26 mol), triethylamine (165.6 g, 218 mL, 1.64 mol, 1.3 equivalents), and toluene (1063 mL). The solution was warmed to 85° C. and then treated dropwise with a solution of diphenylphosphoryl azide (346.8 g, 1.26 mol) over a period of 1.2h. The solution was maintained at that temperature for an additional 1.0 h and then the mixture was treated with 4-methoxybenzyl alcohol (174.1 g, 1.26 mol) over a 0.33 h period from the dropping funnel. The solution was stirred at 88° C. for an additional 2.25 h and then cooled to room temperature. The contents of the flask were poured into a separatory funnel and washed with sat. aq. $NaHCO_3$ (2×500 mL), 0.2N HCl (2×500 mL), brine (1×500 mL), dried over anhyd. $MgSO_4$, filtered, and concentrated in vacuo to give 302.3 g, 85% of the desired product as a slightly brown oil. $^1H$ NMR ($CDCl_3$) 300 MHz 7.32 (d, J=8.4 Hz, 2H), 6.91 (d, J=8.4 Hz, 2H), 5.2(brm, 1H), 5.05(s, 2H), 3.83(s, 3H), 3.70(s, H), 3.35(m, 2H), 2.70(m, 2H), 1.20(d, J=7.2 Hz, 3H).

G. Hydrolysis of Methyl N-Moz-α-methyl β-alanine: Preparation of α-methyl β-alanine Hydrochloride

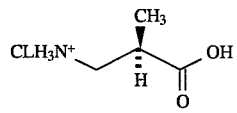

A 5 L three-necked round bottomed flask equipped with a reflux condenser, nitrogen inlet and mechanical stirrer was charged with methyl N-Moz-α-methyl β-alanine (218.6 g, 0.78 mol), glacial acetic acid (975 mL) and 12N hydrochloric acid (1960 mL). The solution was then heated to reflux for 3 h. After the solution had cooled to room temperature (ca. 1 h) the aqueous phase was decanted from organic residue (polymer) and the aqueous phase concentrated on a rotary evaporator. Upon addition of acetone to the concentrated residue a slightly yellow solid formed that was slurried with acetone and the white solid was isolated by filtration on a Buchner funnel. The last traces of acetone were removed by evacuation to give 97.7 g, 90% of pure product, mp 128.5°–130.5° C. $[\alpha]_D$@25° C.=9.0° C. (c=2.535, Methanol). $^1H$ NMR ($D_2O$) 300 MHz 3.29(dd, J=8.6, 13.0 Hz, 1H), 3.16(dd, J=5.0, 13.0 m Hz, 1H), 2.94(ddq, J=7.2, 5.0, 8.6 Hz, 1H), 1.30(d,J=7.2 Hz, 3H); $^{13}C$ NMR ($D_2O$) 180.84, 44.56, 40.27, 17.49.

H. Preparation of N-Boc α-Methyl β-Alanine

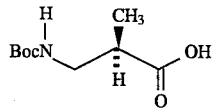

A solution of α-methyl β-alanine hydrochloride (97.7 g, 0.70 mol) in water (1050 mL) and dioxane (1050 mL) the pH was adjusted to 8.9 with 2.9N NaOH solution. This stirring solution was then treated with di-tert- butyl pyrocarbonate (183.3 g, 0.84 mol, 1.2 equivalents) all at once. The pH of the solution was maintained between 8.7 and 9.0 by the periodic addition of 2.5N NaOH solution. After 2.5 h the pH had stabilized and the reaction was judged to be complete. The solution was concentrated on a rotary evaporator (the temperature was maintained at <40° C.). The excess di-tert -butyl pyrocarbonate was removed by extraction with dichloromethane and then the aqueous solution was acidified with cold 1N HCl and immediately extracted with ethyl acetate (4×1000 mL). The combined ethyl acetate extract was washed with brine, dried over anhyd. $MgSO_4$, filtered and concentrated on a rotary evaporator to give a thick oil 127.3 g, 90% crude yield that was stirred with n-hexane whereupon crystals of pure product formed, 95.65 g, 67%, mp 76°–78° C., $[\alpha]_D$@25° C.=–11.8° C. (c=2.4, EtOH). A second crop was obtained by concentration of the filtrate and dilution with hexane, 15.4 g, for a combined yield of 111.05 g, 78%. $^1H$ MMR (acetone $D_6$) 300 MHz 11.7 (brs, 1H), 6.05 (brs 1H), 3.35 (m, 1H), 3.22 (m, 1H), 2.50 (m, 1H), 1.45(s, 9H), 1.19 (d, J=7.3 Hz, 3H); $^{13}C$ NMR (acetone $D_6$) 177.01, 79.28, 44.44, 40.92, 29.08, 15.50. Elemental analysis calc'd. for $C_9H_{17}NO_4$: C, 53.19, H, 8.42; N, 6.89. Found: C, 53.36; H, 8.46; N, 6.99.

I. Preparation of N-4-Methoxybenzyloxycarbonyl α-Methyl β-Alanine

A solution of N-4-methoxybenzyloxycarbonyl α-methyl β-alanine methyl ester (2.81 g, 10.0 mmol) in 30 mL of 25% aqueous methanol was treated with lithium hydroxide (1.3 equivalents) at room temperature for a period of 2 h. The solution was concentrated in vacuo and the residue taken up in a mixture of water and ether and the phases separated and the organic phase discarded. The aqueous phase was acidified with aqueous potassium hydrogen sulfate to pH=1.5 and then extracted three times with ether. The combined ethereal phase was washed with saturated aqueous sodium chloride solution, dried over anhydrous magnesium sulfate, filtered and concentrated in vacuo to give 2.60 g, 97% of N-4-Methoxybenzyloxycarbonyl α-methyl β-alanine (N-Moz-AMBA) which was purified by recrystallization from a mixture of ethyl acetate and hexane to give 2.44 g, 91% of pure product, mp 96°–97° C., MH+=268. $^1H$ NMR ($D_6$-acetone/300 MHz) 1.16 (3H, d, J=7.2Hz), 2.70 (1H, m), 3.31 (2H, m), 3.31 (3H, s), 4.99 (2H, s), 6.92 (2H, 4, J=8.7 Hz), 7.13 (2H, d, J=8.7 Hz).

J. Preparation of Propanamide, 3-(4-methoxybenzyloxycarbonyl)-N-[ 3-[[[(1,1-dimethylethyl)amine]carbonyl](3-methylbutyl)amino]- 2-hydroxy-1-(phenylmethyl) propyl]-2-methyl-[-IS-[ IR* (S*), 2S* ]]-

N-Moz-AMBA (468 mg, 1.75mmol) was dissolved in 5 mL of DMF, HOBT (355 mg, 2.6 mmol) was added and the solution was cooled to 0° C. The solution was treated with (336 mg, 1.75 mmol) EDC for 15 minutes. To this was added (612 mg, 1.75 mmol) of [2R, 3S 3-amino-1-isoamyl-1-(t-butylcarbonyl)amino 4-phenyl-2-butanol in 10 mL of DMF and the reaction stirred for 16 hours at room temperature. The DMF was concentrated to 5 mL and the product was precipitated by addition to 60% saturated aqueous $NaHCO_3$. The solid was taken up in ethyl acetate and washed with $KHSO_4$, $NaHCO_3$, NaCl(saturated), dried over $MgSO_4$ and concentrated to yield 680 mg of crude product which was crystallized from $CH_2Cl_2$, $Et_2O$, hexane, to yield 300 mg of pure product.

EXAMPLE 17

The compounds of Table 8 were prepared according to the procedure listed below and that utilized in Example 16.

Propaneamide,
3-[(1,1-dimethylethyl)butoxycarbonyl]amino-N-[
3-[[[(1,1--dimethylethyl)amino]carbonyl](3-
methylbutyl)amino]-
2-hydroxy-1-(phenylmethyl)propyl]-2-methyl-,[-
1S-[1R*(S*), 2S*]-(Table 8, Entry 11)

Part A

A solution of N-t-butyloxycarbonyl-2-(R)-methyl-3-aminopropionic acid (372 mg, 1.83 mmol) and N-hydroxybenzotriazole (371 mg, 2.75 mmol) in 5 mL of dimethylformamide was cooled to 0° C. To this was added EDC (351 mg, 1.83 mmol) and the solution was stirred for 15 minutes. To this chilled solution was added a solution of 3-[[[(1,1-dimethylethyl)amino]carbonyl](3-methylbutyl)amino]-2(R)-hydroxy-1(S) (phenylmethyl) propylamine in 5 mL of dimethylformamide and stirred for 15 hours. The dimethylformamide was removed and replaced with 50 mL of ethyl acetate, and the organic phase was extracted with 5% potassium hydrogen sulfate, saturated sodium bicarbonate and brine. The ethyl acetate layer was dried over magnesium sulfate, filtered and concentrated to yield 613 mg of product after recrystallization from ethyl acetate, hexanes. (63 % yield) . M+Li 541

Part B

Preparation of Propaneamide, 3-amino-N-[3-[[[(1,1-dimethylethyl) amino]carbonyl]-(3 -methylbutyl)amino]-2-hydroxy- 1-(phenylmethyl)propyl]-2-methyl-, [1S-[1R*(S*), 2S *]-hydrochloride The product from part A. (577 mg, 1.08 mmol) was dissolved in 40 mL of 4N HCl in dioxane and the solution stirred for 2 hours, and concentrated to yield the hydrochloride salt in quantitative yield.

Part C

Preparation of Propaneamide, 3-(2 -methylpropanoylamino)-N-[ 3-[[[(1,1-dimethylethyl)amino]carbonyl] (3-methylbutyl)amino]-2-hydroxy-1-(phenylmethyl)propyl]- 2-methyl-, [1S-[1R*(S*), 2S*]-

The product from part B. (236 mg, 0.5 mmol) was dissolved in anhydrous tetrahydrofuran and to this was added N-methylmorpholine (160 mg, 1.5 mmol) upon which time a precipitate formed. To this suspension was added isobutyryl chloride (53.5 mg, 0.5 mmol) and the suspension stirred for 15 hours. The suspension was diluted with ethyl acetate and washed with 5% potassium hydrogen sulfate, saturated sodium bicarbonate and brine. the organic layer was dried over magnesium sulfate, filtered and concentrated to yield 195 mg of crude product which was chromatographed on silica gel with 5% methanol methylene chloride to yield 121.5 mg (50% yield) of pure product. M+Li 511

TABLE 8

| Entry | R | $R_1$ |
|---|---|---|
| 1 | 4-CH₃O-C₆H₄-CH₂-O-C(O)- | —CH₃ |
| 2 | CH₃-C(O)- | —CH₃ |
| 3 | 4-CH₃O-C₆H₄-CH₂-O-C(O)- | —CH(CH₃)₂ |
| 4 | CH₃-C(O)- | —CH(CH₃)₂ |
| 5 | C₆H₅-CH₂-O-C(O)- | —C(CH₃)₃ |
| 6 | 2-naphthyl-OCH₂-C(O)- | —CH₃ |
| 7 | C₆H₅-O-CH₂-C(O)- | —CH₃ |
| 8 | HO₂CCH₂CH₂-C(O)- | —CH₃ |
| 9 | C₆H₅-C(O)H- | —CH₃ |
| 10 | CH₃NH-C(O)- | —CH₃ |
| 11 | (CH₃)₂CH-C(O)- | —CH₃ |
| 12 | CH₃OCH₂-C(O)- | —CH₃ |
| 13 | (CH₃)₂NCH₂-C(O)- | —CH₃ |

TABLE 8-continued

| Entry | R | R₁ |
|---|---|---|
| 14 | CH₃CH(OH)—C(O)— | —CH₃ |
| 15 | CH₃O—C₆H₄—CH₂O—C(O)NH— (on cyclohexyl) | |
| 16 | C₆H₅—CH₂—OC(O)NH— (on cyclobutyl) | |

EXAMPLE 18

Following generally the procedure set forth in Example 16, the compounds shown in Table 9 were prepared.

TABLE 9

| R¹ | R¹' | R¹" | R |
|---|---|---|---|
| H | H | H | C₆H₅—CH₂O—C(O)— |
| H | H | H | CH₃C(O)— |
| H | CH₃ | H | CH₃O—C₆H₄—CH₂OC(O)— |
| H | CH₃ | CH₃ | C₆H₅—CH₂O—C(O)— |
| H | H | CO₂CH₃ | C₆H₅—CH₂O—C(O)— |

TABLE 9-continued

| R¹ | R¹' | R¹" | R |
|---|---|---|---|
| H | H | H | CH₃O—C₆H₄—CH₂O—C(O)— |
| H | H | H | H₂N—C(O)— |
| H | H | CONH₂ | Cbz |
| H | H | CONH₂ | 2-quinolinylcarbonyl |
| H | H | CONH₂ | 2-benzofurancarbonyl |

EXAMPLE 19

The procedure set forth below in Example 23 was generally utilized to prepare the compounds shown in Table 10.

TABLE 10

| R | R' | X |
|---|---|---|
| R=H | R'=H | X=H |
| R=Me | R'=Me | X=H |
| R=H | R'=Me | X=H |
| R=Me | R'=Me | X=F |
| R=H | R'=Me | X=F |
| R=Cbz | R'=Me | X=H |
| R=H | R'=Bz | X=H |
| R + R" = pyrrole* | | X=H |

*Ile in place of t-butylglycine

EXAMPLE 20

This example illustrates preparation of compounds wherein $R^4$ and $R^5$ together with N, forms a heterocycloalkyl radical.

a) Pyrrolidine carbamoyl chloride

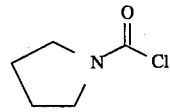

A stirring solution of triphosgene (27.78 g, 0.103 mol) in 40 mL toluene was cooled to −20 °C. in an ice/salt bath under a blanket of nitrogen and treated with a solution of N-methylmorpholine (27.3 g, 0.27 mol) in 20 mL of toluene dropwise over 1 h. This solution was then treated with a solution of pyrrolidine (19.8 g, 0.27 mol) in 30 mL of toluene over a period of 30 m. The solution was allowed to warm to room temperature, filtered and the filtrate concentrated in vacuo to give an oil that was purified by vacuum distillation through a 12" Vigeraux column to give 20.7 g, 56%, bp 58° C. @0.6 mm, of pure product.

b) Butanediamide, $N^1$[3-[[(4-fluorophenyl)methyl)](1-pyrrolidinylcarbonyl)amino]-2-hydroxy-1-(phenylmethyl)propyl]-2-[(2-quinolinylcarbonyl)amino]-[-1S[1R*(R*),2S*]]-

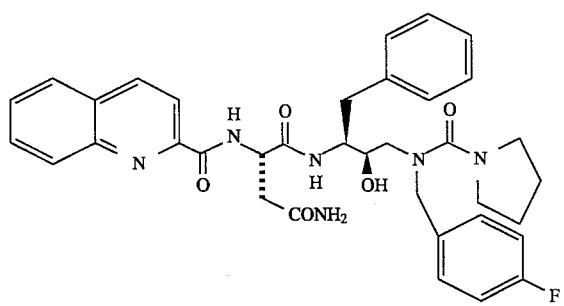

A stirring solution of [IS-[1R* (R*), 2S*]]-N1-[3-[ [(4-fluorophenyl)methyl]amino]-2-hydroxy-1-(phenylmethyl)propyl]- 2-[(2-quinolinylcarbonyl)aminobutanediamide (1.08 g, 1.91 mmol) (prepared as in Example 31) in 7 mL of anhydrous DMF was treated with pyrrolidine carbamoyl chloride (260 mg, 1.95 mmol), 4-dimethylaminopyridine (15 mg), and N-methylmorpholine (380 mg, 3.76 mmol). The solution was stirred at room temperature for 3 h and then concentrated in vacuo to give a semi-solid that was dissolved in methanol/water ca. 2:1. A solid formed from this solid that was isolated by filtration on a Büchner funnel and washed with water, 5% aq. citric acid and water and air dried to give 130 mg of pure product, TLC on SiO₂ eluting with 7% methanol in ethyl acetate showed one spot with $R_f$=0.64, 11%.

c) Butanediamide, $N^1$[3-[[(4-fluorophenyl)methyl)](4-morpholinylcarbonyl)amino]-2-hydroxy-1-(phenylmethyl)propyl]-2-[(2quinolinylcarbonyl)amino]-[-1S[1R*(R*),2S*]]-

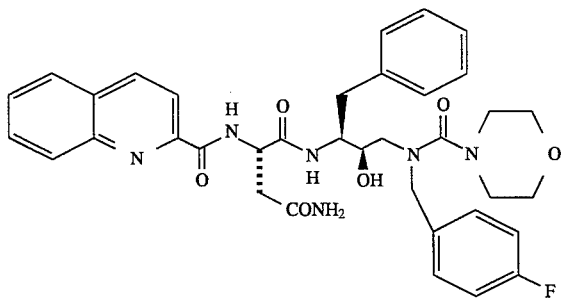

To a stirring solution of [1S-[1R*(R*),2S*]]-$N^1$-[ 3-[[(4-fluorophenyl)methyl]amino]-2-hydroxy-1-(phenylmethyl)propyl]- 2-[(2-quinolinylcarbonyl)aminobutanediamide (520 mg, 0.922 mmol), triethylamine (172 mg, 1.70 mmol), 4-dimethylaminopyridine (50 mg), and morpholino carbamoyl chloride (157.3 mg, 1.05 mmol) in 5 mL of chloroform. The initially heterogeneous mixture was heated to reflux for 6 h. The solution was then diluted with additional chloroform, poured into a separatory funnel and washed with 1N KHSO₄, sat. aq. NaHCl₃, dried over anhyd. MgSO₄, filtered, and concentrated in vacuo to give a white solid that was purified by column chromatography on SiO₂ eluting with ethanol/ethyl acetate to give 380 mg, 61%, of pure product.

EXAMPLE 21

This example illustrates preparation of compounds wherein $R^4$ and $R^5$ are both other than H.

Butanediamide, $N^1$[3-[[(diethylamino)carbonyl](3-methylbutyl)amino]-2-hydroxy-1-(phenylmethyl)propyl]-2-[(2-(quinolinylcarbonyl)amino]-[1S[1R*(R*),2S*]]-

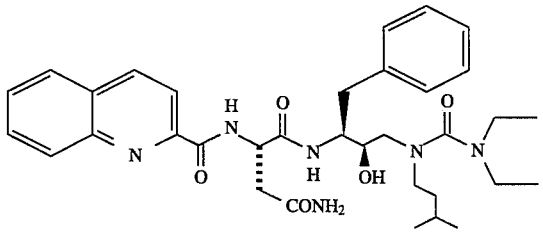

To a stirring solution of [1S-[1R*(R*),2S*]]-N¹-[ 3-(methylbutyl)amino]-2-hydroxy-1-(phenylmethyl)propyl]-2-( 2-quinolinylcarbonyl)amino-butane diamide](119 mg, 0.21 mmol) triethylamine (59 mg, 0.58 mmol), 4-dimethylaminopyridine (9 mg), and diethyl carbamoyl chloride (157.3 mg, 1.05 mmol) in 4 mL of chloroform. The mixture was kept at room temperature for 26 h. The solution was then diluted with additional chloroform, poured into a separatory funnel and washed with 1N KHSO₄, sat. aq. NaHCO₃, dried over anhyd. MgSO₄, filtered, and concentrated in vacuo to give a white solid that was purified by column chromatography on SiO₂ eluting with methanol/CH₂Cl₂ to give 20 mg, 15%, of pure product.

EXAMPLE 22

Following the procedures set forth in Examples and 21, the compounds listed in Table 11 were prepared.

TABLE 11

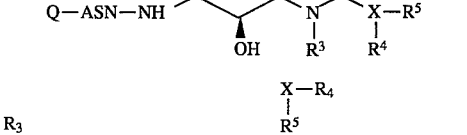

| R₃ | X—R₄<br>R⁵ |
|---|---|
| —CH₂CH(CH₃)₂ | —N(CH₃)₂ |
| —CH₂CH(CH₃)₂ | —N(CH₂CH₃)₂ |
| —CH₂CH(CH₃)₂ | —N(CH(CH₃)₂)₂ |
| —CH₂CH₂CH(CH₃)₂ | —N(CH₃)₂ |
| —CH₂CH₂CH(CH₃)₂ | —N(CH₂CH₃)₂ |
| —CH₂CH₂CH(CH₃)₂ | 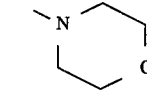 |
| 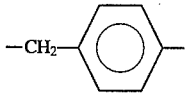 | —N(CH₃)₂ |
| 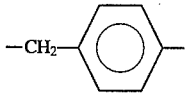 | —N(CH₂CH₃)₂ |
| 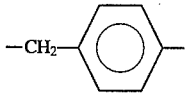 | 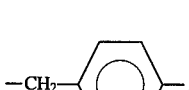 |
| 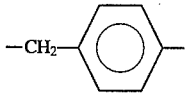 | 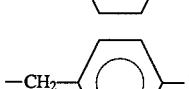 |
| 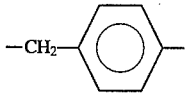 | N(CH₃) (t-Bu) |
| 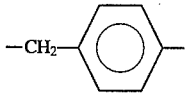 | 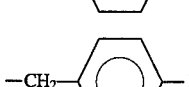 |

TABLE 11-continued

| R₃ | X—R₄<br>R⁵ |
|---|---|
| —CH₂-⟨⟩-F | N-CO₂CH₃ (pyrrolidine) |
| —CH₂-⟨⟩-F | piperidine-CH₃ |
| —CH₂-⟨⟩-F | piperazine-N-CH₃ |
| —CH₂-⟨⟩-F | azocane |
| —CH₂-⟨⟩-F | azocane |
| —CH₂-⟨⟩-F | bicyclic amine |
| —CH₂-⟨⟩-F | bicyclic amine |

EXAMPLE 23A

This example illustrates preparation of compounds of Formula II wherein R¹ is an alkyl group other than an alkyl group of a naturally occurring amino acid side chain. In particular R¹ is a t-butyl group.

Part A

3-[[(1,1-dimethylethyl)amino]carbonyl](3-methylbutyl)amino- 2(R)-hydroxy-1(S)-[N-(benzyloxycarbonyl) (phenylmethyl()propyl amine](4.7 gm, 9.7 mmol) was combined with 10% Pd on carbon (200 mg) and conc. HCl (3 mL) in ethanol (35 mL) and hydrogenated at 50 psi of hydrogen for 2.5 h. The reaction mixture was filtered through diatomaceous earth and concentrated on a rotary evaporator to a yellow hygroscopic solid; 3.7 gm, 100%.

Part B

Butaneamide,
2-[(phenylmethyloxycarbonyl)amino]-N-[3-[
[[(1,1-dimethylethyl)amino]carbonyl](3-
methylbutyl)amino]
2-hydroxy-1-(phenylmethyl)propyl-3,3-dimethyl-[1S-[
1R* (R*), 2S*]]

N-Cbz-L-tert-leucine (172 mg, 0.65 mol) and N-hydroxybenzotriazole (100 mg, 0.65 mmol) in DMF (3 mL) was cooled to 0° C. and EDC (115 mg, 0.60 mmol) added. After 45 min the amine from Part A (193 mg, 0.50 mmol) and N-methylmorpholine (60 uL, 0.55 mmol) were added. The reaction was stirred at ambient temperature for 18 h and poured into a solution of 50% saturated $NaHCO_3$ (25 mL). The solid was collected by suction filtration, washed with water and dried in-vacuo. The solid was chromatographed on $SiO_2$ using 2% MeOH in $CH_2Cl_2$. The appropriate fractions were pooled and concentrated to afford a white solid; 220 mg, $MH^+$597, TLC ($SiO_2$ 2%MeOH/$CH_2Cl_2$) $R_f$=0.2 . CHN requires: C, 68.42, H, 8.78, N, 9.39; found: C, 68.03, H, 8.83, N, 9.33.

Part C

Butaneamide,
2-amino-N-[3-[[[(1,1-dimethylethyl)amino]
carbonyl](3-methylbutyl)amino]-2-hydroxy-
1-(phenylmethyl)propyl]-3,3-dimethyl-,
[1S-[1R*(R*), 2S*]-

The product from Part B (570 mg, 0.95 mmol) and 4% Pd on carbon (150 mg) in ethanol (30 mL) was hydrogenated at 5 psi for 2.75 h. The reaction mixture was filtered through diatomaceous earth and concentrated on a rotary evaporator to an oil; 438 mg, 100%.

Part D

Butaneamide,
2-(acetylamino)-N-[3-[[[(1,1-dimethylethyl)
amino]carbonyl]( 3-methylbutyl)amino]-2-hydroxy-
1-(phenylmethyl)propyl]-3,3-dimethyl-,
[1S-[1R*(R*), 2S*]-

The product from Part C (206 mg, 0.41 mmol) and N-methylmorpholine (45 uL, 0.41 mmol) were dissolved in $CH_2Cl_2$ (2.5 mL) and cooled to 0 C. Acetic anhydride (39 uL, 0.41 mmol) was then added and the reaction stirred 30 min at 0 C, then allowed to warm to ambient temperature and stir for 30 min. The solvent was removed on a rotary evaporator and the residue dissolved in ethanol (2 mL). The ethanolic solution was slowly poured into 50 % saturated $NaHCO_3$ (20 mL) and stirred vigorously. The solid was collected by suction filtration and washed with water, 5% citric acid, and again with water; 157 mg, 75%. CHN/1.5 $H_2O$ requires: C 63.24, H, 9.67, N, 10.54; found: C, 63.40, H, 9.41, N, 10.39.

Part D2:

Butaneamide,
2-[(2,2-dimethylaminoacetyl)amino]-N-[3-[
[[(1,1-dimethylethyl)amino]carbonyl](3-
methylbutyl)amino]-
2-hydroxy-1-(phenylmethyl)propyl]-3,3-dimethyl-,
[1S-[1R*-(R*), 2 S*-]]

To a solution of N,N-dimethylaminoacetic acid (62 mg, 0.6 mmol) and N-hydroxybensotriazole (87 mg, 0.57 mmol) in 2 mL of DMF at 0° C. was added EDC (109 mg, 0.57 mmol). The reaction mixture was stirred for 1 hour and then (2R, 3S)- 3(L-tert-butylglycinyl) amino-1-isoamyl 1(tert-butylcarboamoyl) amino-4-phenyl-2-butanol (231 mg, 0.5 mmol) was added. The reaction was stirred at room temperature for 16 hours and then concentrated in vacuo. The residue was chromatographed on silica (50 gm) using 5% ethanol in dichloromethane. The butaneamide, 2-[(2,2-dimethylaminoacetyl)amino]-N-[ 3-[[[(1,1-dimethylethyl)amino]carbonyl]( 3-methylbutyl)amino]-2-hydroxy-1-(phenylmethyl) propyl]-3,3-dimethyl-, [1S[ 1R*(R*)), 2S*]]- was obtained as a white solid Anal. Calc'd for $C_{30}H_{53}N_5O_4$.0.3 $H_2O$:C,65.13;H, 9.77; N, 12.66. Found: C, 65.10; H, 9.79; N, 12.52.

EXAMPLE 23B

The compound of Example 23A, Part D2, was prepared by an alternate method as described below. To a solution of butaneamide, 2-amino-N-[3-[[[(1,1-dimethylethyl)amino]-carbonyl]( 3-methylbutyl)amino]-2-hydroxy- 1-(phenylmethyl) propyl]-3,3-dimethyl-, [1S-[1R*(R*), 2S*]-(694 mg, 1.5 mmol) and N-methylmorpholine (175 uL, 1.6 mmol) in 5 mL of dichloromethane was added bromoacetyl chloride (132 uL, 1.6 mmol). After 20 minutes at room temperature the solvent was removed on a rotary evaporator and the residue chromatographed on silica (50 gm) using 2% methanol in dichloromethane. The product was obtained as a white solid Anal. Calc'd for $C_{28}H_{47}N_4O_4Br$. $H_2O$: C, 55.90; H, 8.21; N, 9.31. Found: C, 55.67; H, 7.90; N, 9.08.

To a solution of butaneamide, 2-[(2-bromoacetyl)amino] -N-[3-[ [[(1,1-dimethylethyl)amino]carbonyl](3-methylbutyl)amino]- 2-hydroxy-1-(phenylmethyl)propyl]-3,3-dimethyl-,[1S-[1R*(R*), 2S*]]-(582 mg, 1.0 mmol) and N,N-diisopropylethylamine (260 $mL^2$, 1.5 mmol) in 10 mL of dichloromethane was added N,N-dimethylamine hydrochloride (122 mg 1.5 mmol). The reaction was stirred at room temperature for 16 hours, then concentrated on a rotary evaporator. The residue was chromatographed on silica (50 gm) using 2.5% methanol in dichloromethane. The butaneamide, 2-[(2,2-dimethylaminoacetyl)amino]-N-[ 3-[[[(1,1-dimethylethyl) amino]-carbonyl](3-methylbutyl)amino]-2-hydroxy- 1-(phenylmethyl)propyl]-3,3-dimethyl-, [1S-[1R*(R*), 2S*]]- was obtained as a white solid Anal Calc'd for $C_{30}H_{53}N_5O_4$0.22 $CH_2Cl_2$: C, 64.00; H, 9.50; N, 12.35. Found: C, 63.97; H, 9.51; N, 12.24.

Butaneamide, 2-amino-N-[3-[[[(1,1-dimethylethyl)amino]carbonyl]( 3-methylbutyl)amino]-2-hydroxy-1-(phenylmethyl)propyl]- 3,3-dimethyl-, [1S-[1R*(R*), 2S*]- was also capped, generally utilizing the procedures shown in Examples 23A and 23B, with the acyl groups shown in Table 12.

TABLE 12

| Acyl Group (R) |
| --- |
| benzyloxycarbonyl |
| tert-butoxycarbonyl |
| acetyl |
| 2-quinoylcarbonyl |
| phenoxyacetyl |
| benzoyl |
| methyloxaloyl |
| pivaloyl |
| trifluoracetyl |
| bromoacetyl |
| hydroxyacetyl |
| morpholinylacetyl |
| N-benzylaminoacetyl |

TABLE 12-continued

Acyl Group (R)

N-phenylaminoacetyl
N-benzyl-N-methylaminoacetyl
N-methyl-N-(2-hydroxyethyl)aminoacetyl
N-methylcarbamoyl
3-methylbutyryl
N-isobutylcarbamoyl
succinoyl (3-carboxypropionyl)
carbamoyl
N-isobutylamino acetyl
N,N-diethylamino acetyl
N-(2-methoxyethyl)aminoacetyl
N-(S-α-methylbenzyl)aminoacetyl
N-(R-α-methylbenzyl)amino acetyl
N-(S-2-tetralin)amino acetyl
N-(R-2-teralin)amino acetyl
N-pyrrolidinylacetyl
N-methyl-N-(2-pyridylethyl)amino acetyl
N-tetrahydroisoquinolylaminoacetyl
N-p-methoxybenzylamino acetyl

EXAMPLE 24A

The procedure described below illustrates preparation of compounds of Formula III. Propanamide, N-[3-[[[(1,1-dimethylethyl)amino]carbonyl](3-methylbutyl)amino]- 2-hydroxy-1-(phenylmethyl)propyl]-2-methyl- 3-(2-phenylethylsulfonyl)-, [1S-[1R*(R*),2S*]] and its diastereomer.

Part A

A solution of methyl methacrylate (7.25 g, 72.5 mmol) and phenethyl mercaptan (10.0 g, 72.5 mmol) in 100 mL of methanol was cooled in an ice bath and treated with sodium methoxide (100 mg, 1.85 mmol). The solution was stirred under nitrogen for 3 h and then concentrated in vacuo to give an oil that was taken up in ether and washed with 1 N aqueous potassium hydrogen sulfate, saturated aqueous sodium chloride, dried over anhydrous magnesium sulfate, filtered and concentrated to give 16.83 g, 97.5% of methyl 2-(R, S)-methyl-4-thia-6-phenyl hexanoate as an oil. TLC on $SiO_2$ eluting with 20:1 hexane: ethyl acetate (v:v) $R_f$=0.41.

Part B

A solution of methyl 2-(R,S)-methyl-4-thia-6-phenyl hexanoate (4.00 g, 16.8 mmol) in 100 mL of dichloromethane was stirred at room temperature and treated portion wise with meta-chloroperoxybenzoic acid (7.38 g, 39.2 mmol) over approximately 40 m. The solution was stirred at room temperature for 16 h and then filtered and the filterate washed with saturated aqueous sodium bicarbonate, 1N sodium hydroxide, saturated aqueous sodium chloride, dried over anhydrous magnesium sulfate, filtered, and concentrated to give 4.50 g, 99% of desired sulfone. The unpurified sulfone was dissolved in 100 mL of tetrahydrofuran and treated with a solution of lithium hydroxide (1.04 g, 24.5 mmol) in 40 mL of water. The solution was stirred at room temperature for 2 m and then concentrated in vacuo. The residue was then acidified with 1N aqueous potassium hydrogen sulfate to pH=1 and then extracted three times with ethyl acetate. The combined ethyl acetate solution was washed with saturated aqueous sodium chloride, dried over anhydrous magnesium sulfate, filtered and concentrated to give a white solid. The solid was taken up in boiling ethyl acetate/hexane and allowed to stand undisturbed whereupon white needles formed that were isolated by filtration and air dried to give 3.38 g, 79% of 2-(R, S)-methyl-3 (β-phenethylsulfonyl)-propionic acid, mp 91°–93° C.

Part C

A solution of 2-(R,S)-methyl-3(β-phenethylsulfonyl)-propionic acid (166.1 mg, 0.65 mmol), N-hydroxybenzotriazole (HOBT) (146.9 mg, 0.97 mmol), and 1-( 3-dimethylaminopropyl)-3-ethylcarbodiimide hydrochloride (EDC) (145.8 mg, 0.75 mmol) in 4 mL of anhydrous dimethylformamide (DMF) cooled to 0° C. and stirred under nitrogen for 0.5 h. This solution was then treated with 3-[ [(dimethylethyl)amino]carbonyl](3-methylbutyl)amino-2 (R)-hydroxy-1(S)-(phenylmethyl)propyl amine (201.9 mg, 0.59 mmol) and stirred at room temperature for 16 h. The solution was poured into 30 mL of 60% saturated aqueous sodium bicarbonate solution. The aqueous solution was then decanted from the organic residue. The organic residue was taken up in dichloromethane and washed with 10% aqueous citric acid, brine, dried over anhydrous magnesium sulfate, filtered and concentrated to give 110.0 mg, 32% of (2R,3S)- 3-[N-2-(R)-methyl-3-(β-phenethylsulfonyl)propionyl]amido-1-isoamyl- 1-(tert-butylcarbamoyl)amino-4-phenyl -2-butanol and (2R,3S)-3-[N-2-(S)-methyl-β-phenethylsulfonyl)propionyl] amido-1-isoamyl-1-(tert-butylcarbamoyl)amino-4-phenyl-2-butanol, FAB mass spectrum (MH+)=588. Flash chromatography of the mixture on silica gel eluting with 1:1 hexane:ethyl acetate afforded the separated diastereomers.

EXAMPLE 24B

Propanamide, N-[3-[[[(1, 1-dimethylethyl)amino]carbonyl](3-methylbutyl)amino]- 2-hydroxy-1-(phenylmethyl)propyl]-2-methyl- 3-(methylsulfonyl)-[1S-[1R*(R*), 2S*]], and its diastereomer.

Part A

A solution of methyl 2-(bromomethyl)-acrylate (26.4 g, 0,148 mol) in 100 mL of methanol was treated with sodium methanesulfinate (15.1 g, 0. 148 mol) portion wise over 10 m at room temperature. The solution was then stirred at room temperature for a period of 1.25 h and the solution concentrated in vacuo. The residue was then taken up in water and extracted four times with ethyl acetate. The combined ethyl acetate solution was washed with saturated sodium chloride, dried over anhydrous magnesium sulfate, filtered and concentrated to give a white solid, 20.7 g which was taken up in boiling acetone/methyl tert-butyl ether and allowed to stand whereupon crystals of pure methyl 2-(methylsulfonylmethyl) acrylate 18.0 g, 68% formed, mp 65°–68 0° C.

Part B

A solution of methyl 2-(methylsulfonylmethyl) acrylate (970 mg, 5.44 mmol) in 15 mL of tetrahydrofuran was treated with a solution of lithium hydroxide (270 mg, 6.4 mmol) in 7 mL of water. The solution was stirred at room temperature for 5 m and then acidified to pH=1 with 1 N aqueous potassium hydrogen sulfate and the solution extracted three times with ethyl acetate. The combined ethyl acetate solution was dried over anhydrous magnesium sulfate, filtered, and concentrated to give 793 mg, 89% of 2-(methylsulfonylmethyl) acrylic acid, mp 147°–149 0° C.

Part C

A solution of 2-(methylsulfonylmethyl) acrylic acid (700 mg, 4.26 mmol) in 20 mL of methanol was charged into a Fisher-Porter bottle along with 10% palladium on carbon catalyst under a nitrogen atmosphere. The reaction vessel was sealed and flushed five times with nitrogen and then five times with hydrogen. The pressure was maintained at 50 psig for 16 h and then the hydrogen was replaced with nitrogen and the solution filtered through a pad of celite to remove the catalyst and the filterate concentrated in vacuo to give 682 mg 96% of 2-(R,S)-methyl-3-methylsulfonyl propionic acid.

Part D

A solution of 2-(R,S)-methyl-3-(methylsulfonyl) propionic acid (263.5 mg, 1.585 mmol), N-hydroxybenzotriazole (HOBT) (322.2 mg, 2.13 mmol), and 1-( 3-dimethylaminopropyl)-3-ethylcarbodiimide hydrochloride (EDC) (339.1 mg, 1.74 mmol) in 4 mL of anhydrous dimethylformamide (DMF) cooled to 0° C. and stirred under nitrogen for 0.5 h. This solution was then treated with 3-[ [(1,1-dimethylethyl)aminocarbonyl](3-methylbutyl)amino- 2(R)-hydroxy-1(S)-(phenylmethyl)propyl amine (543.5 mg, 1.58 mmol) and stirred at room temperature for 16 h. The solution was poured into 60 mL of 60% saturated aqueous sodium bicarbonate solution. The aqueous solution was then decanted from the organic residue. The organic residue was taken up in dichloromethane and washed with 10% aqueous citric acid, brine, dried over anhydrous magnesium sulfate, filtered and concentrated to give 471.8 mg, 60% of Propanamide, N-[3-[[[(1,1-dimethylethyl)amino]carbonyl](3-methylbutyl)amino]- 2-hydroxy-1-(phenylmethyl)propyl]-2-methyl-3-(methylsulfonyl)-, [1S-[1R*(R*), 2S*]]- and its diastereomer.

EXAMPLE 25

Preparation of Sulfone Inhibitors From L-(+)-S-acetyl-β-mercaptoisobutyric Acid

Part A

Propanamide, N-[3-[[[(1,1-dimethylethyl)amino] carbonyl](3-methylbutyl)amino]-2-hydroxy- 1-(phenylmethyl)propyl]-2-methyl-3-S-acetyl)-[1S-[ 1R*), 2S*]]-.

A round-bottomed flask was charged with (2R,3R)-3-amino-1-isoamyl-1-(tert-butylcarbamoyl)amino-4-phenyl -2-butanol (901.5 mg, 2. 575 mmol), L-(+)-S-acetyl-b-mercaptoisobutyric acid (164.5 mg, 2.575 mmol), 1-(3-dimethylaminopropyl)- 3-ethylcarbodiimide hydrochloride (EDC) (339.1 mg, 1.74 mmol), and 10 mL of CH$_2$Cl$_2$ and allowed to stir at room temperature for 16 h. The solution was concentrated in vacuo and the residue taken up in ethyl acetate, washed with 1N KHSO$_4$ sat. aq. NaHCO$_3$, brine, dried over anhydrous MgSO$_4$, filtered and concentrated to give an oil that was purified by radial chromatography on SiO$_2$ eluting with ethyl acetate to give the pure product, 800 mg, 63%.

Part B

Propanamide, N-[3-[[[1,1-dimethylethyl)amino]carbonyl]( 3-methylbutyl)amino]-2-hydroxy-1-(phenylmethyl)propyl]- 2-methyl-3-mercapto)-, [1S-[1R*(R*),2S*]]-.

A solution of [1S-[1R*(R*), 2S*]]- N-[3-[[[(1,1-dimethylethyl)amino] carbonyl](3-methylbutyl)amino]-2-hydroxy-1-(phenylmethyl)propyl]-2-methyl-3-S-acetyl)propanamide (420 mg, 0.85 mmol) in 10 mL of methanol was treated with anhydrous ammonia for ca. 1 m at 0° C. The solution was stirred at that temperature for 16 h and then concentrated in vacuo to give 380 mg, 99%, of the desired product that was used directly in the next step without further purification.

Part C

Propanamide, N-[3-[[[(1,1-dimethylethyl)amino]carbonyl]-( 3-methylbutyl)amino]-2-hydroxy-1- (phenylmethyl)propyl]- 2-methyl-3-S-methyl-, [1S-[1R*(R*),2S*]]-.

A solution of [1S-[1R*(R*),2S*]]- N-[3-[[[(1,1-dimethylethyl)amino] carbonyl](3-methylbutyl)amino]-2-hydroxy-1-(phenylmethyl)propyl]-2-methyl-3-mercapto)propanamide (380 mg, 0.841 mmol) in 10 mL of dry toluene under nitrogen was treated in rapid succession with 1,8-diazabicyclo[ 5.4.0]undec-7-ene, (DBU), (128.1 mg. 0.841 mmol) and iodomethane (119.0 mg, 0. 841 mmol). After 0.5 h at room temperature the reaction was found to be complete and the solution was diluted with ethyl acetate washed with 1N KHSO$_4$, sat. aq. NaHCO$_3$, brine. After the solution was dried over anhydrous MgSO$_4$, filtered and concentrated in vacuo the desired product was obtained as white foam was obtained, 370 mg, 94.5%, that was used directed in the next step.

Part D

Propanamide, N-[3-[[[(1,1-dimethylethyl)amino]carbonyl]( 3-methylbutyl)amino]-2-hydroxy-1-(phenylmethyl)propyl]- 2-methyl-3-(methylsulfonyl)-, [1S-[1R*(R*),2S*] ]-.

A solution of [1S-[1R*(R*),2S*]]-N-[3-[[[(1,1-dimethylethyl)amino] carbonyl](3-methylbutyl)amino]-2-hydroxy-1-(phenylmethyl)propyl]-2-methyl -3-S-methyl)propanamide (340 mg, 0.73 mmol) and sodium perborate (500 mg, 3.25 mmol) in 30 mL of glacial acetic acid was warmed to 55° C. for 16 h. The solution was conentrated in vacuo and then the residue taken up in ethyl acetate, washed with water, sat. aq. NaHCO$_3$, brine, dried over anhydrous MgSO$_4$, filtered and concentrated to give the desired product as a white solid, 350 mg, 96%.

EXAMPLE 26

The compounds shown in Tables 13A and 13B were prepared generally according to the procedure set forth in Examples 24 and 25.

TABLE 13A

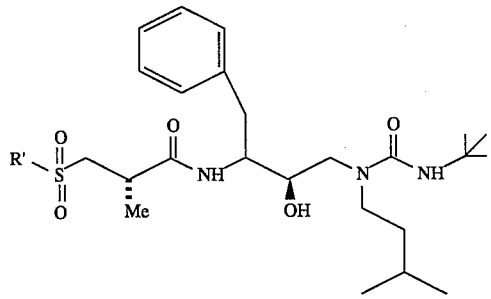

| R' |
|---|
| CH₃— |
| CH₃CH₂— |
| CH₃CH₂CH₂— |
| PhCH₂CH₂— |
| PhCH₂— |
| Ph— |
| (CH₃)₂CH— |
| HOCH₂CH₂— |
| C₆H₅CH₂O—C(O)CH₂ |
| H₂NC(O)CH₂— |
| 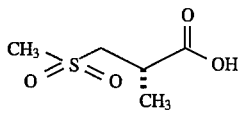 |
| CH₂=CH—CH₂— |

TABLE 13B

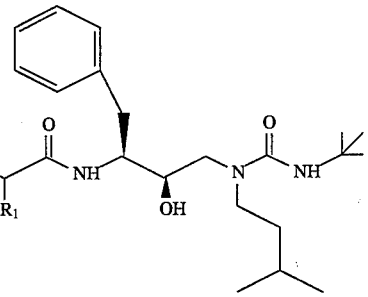

| R' | R₁ |
|---|---|
| CH₃ | —CH(CH₃)₂ |
| CH₃ | —CH(CH₃)₃ |

Preparation of 2(S)-methyl-3-(methylsulfonyl)propionic Acid

To a solution of 10 g of D-(−)-S-benzoyl-b-mercaptio-isobutyric acid t-butyl ester in 20 mL of methanol was bubbled in gaseous ammonia at 0° C. The reaction was allowed to then warm to room temperature, stirred overnight and concentrated under reduced pressure. The resulting mixture of a solid (benzamide) and liquid was filtered to provide 5.21 g of a pale oil which then solidified. This was identified as 2(S)-methyl-3-mercaptopropionic aid t-butyl ester.

To a solution of 5.21 g of 2(S)-methyl-3-mercaptopropionic acid t-butyl ester in 75 mL of toluene at 0° C. was added 4.50 g of 1,8-diazabicyclo[5.40]undec-7-ene and 1.94 mL of methyl iodide. After stirring at room temperature for 2.5 hours, the volatiles were removed, ethyl acetate added, washed with dilute hydrochloric acid, water, brine, dried and concentrated to afford 2.82 g of a pale oil, identified as 2(S)-methyl-3-(thiomethyl)propionic acid t-butyl ester.

To a solution of 2.82 g of 2(S)-methyl-3-(thiomethyl)propionic acid t-butyl ester in 50 mL of acetic acid was added 5.58 g of sodium perborate and the mixture heated to 55° C. for 17 hours. The reaction was poured into water, extracted with methylene chloride, washed with aqueous sodium bicarbonate, dried and concentrated to afford 2.68 g of 2(S)-methyl-3-(methylsulfonyl)propionic acid t-butyl ester as a white solid.

To 2.68 g of 2(S)-methyl-3-(methylsulfonyl)propionic acid t-butyl ester was added 20 mL of 4N hydrochloric acid/dioxane and the mixture stirred at room temperature for 19 hours. The solvent was removed under reduced pressure to afford 2.18 g of crude product, which was recrystallized from ethyl acetate/hexane to yield 1.44 g of 2(S)-methyl-3-(methylsulfonyl)propionic acid as white crystals.

EXAMPLE 28

This example illustrates preparation of compounds of Formula IV wherein t is 1.

4-N-benzyl itaconamide.

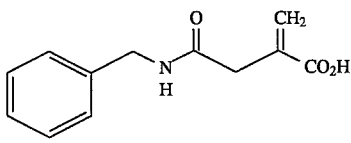

A 500 mL three necked round bottomed flask equipped with a dropping funnel, mechanical stirrer, nitrogen inlet and reflux condenser was charged with itaconic anhydride (33.6 g, 0.3 mol) and 150 mL of toluene. This solution was added a solution of benzylamine (32.1 g, 0.3 mol) in 50 mL of toluene dropwise over 30 m at room temperature. The solution was stirred at this temperature an additional 3 h and then the solid product isolated by filtration on a Bochner funnel. The crude product, 64.6 g 98%, was recrystallized from 300 mL of isopropyl alcohol to give after two crops 52.1 g, 79% of pure product, mp 149°–150° C.

2(R)-Methyl 4-N-benzyl succinamide.

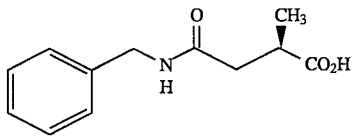

A large Fisher-Porter bottle was charged with the acid from the above reaction (10.95 g, 0.05 mol), rhodium (R,R)-DiPAMP (220mg, 0.291 mmol) and 125 mL of degassed methanol. The solution was then hydrogenated at 40 psig for 16 h at room temperature. After the hydrogen uptake ceased, the vessel was opened and the solution concentrated in vacuo to give a yellow solid, 11.05 g, 100%. The product was then taken up in absolute ethanol and allowed to stand whereupon crystals of the desired product formed, 7.98 g, 72%, mp 127°–129 ° C. $[a]_D$ @25° C.=+14.9° (c=1.332, EtOH), 1H nmr (CDCl₃) 300MHz 7.30 (m, 5H), 6.80 (brs, 1H), 4.41 (d, J=5.8Hz, 2H), 2.94 (m, 1H), 2.62 (dd, J=8.1, 14.9Hz, 1H), 2.33(dd, J=5.5, 14.9Hz, 1H), 1.23(d, J=7.2Hz, 3H).

4-N(4-methoxybenzyl)itaconamide.

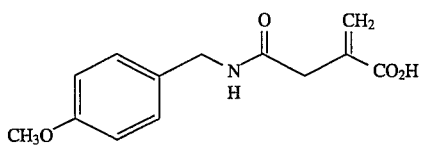

A 500 mL three necked round bottomed flask equipped with a dropping funnel, mechanical stirrer, nitrogen inlet and reflux condenser was charged with itaconic anhydride (44.8 g, 0.4 mol) and 150 mL of toluene. This solution was added a solution of 4-methoxybenzylamine (54.8 g, 0.4 mol) in 50 mL of toluene dropwise over 30 m at room temperature. The solution was stirred at this temperature an additional 2 h and then the solid product isolated by filtration on a Bochner funnel. The crude product was recrystallized from ethyl acetate/ethanol to give after two crops 64.8 g, 65% of pure product, mp 132°–134° C., $^1$H nmr (CDCl$_3$) 300MHz 7.09(d, J=9.1Hz, 2H), 6.90(brt, J=5.9Hz, 1H), 6.74(d, J=9.1Hz, 2H), 6.22(s, 1H), 5.69(s, 1H), 4.24(d, J=5.9Hz, 2H), 3.69(s, 3H), 3.15(s, 2H). $^{13}$C nmr (CDCl$_3$) 170.52, 169.29, 159.24, 135.61, 131.08, 129.37, 128.97, 114.36, 55.72, 43.37, 40.58.

2(R)-Methyl 4-N(4-methoxybenzyl)succinamide.

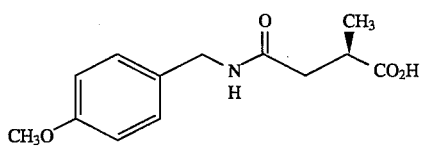

A large Fisher-Porter bottle was charged with the acid from the above reaction (5.00 g, 0.02 mol), rhodium (R, R)-DiPAMP (110 mg, 0.146 mmol) and 50 mL of degassed methanol. The starting acid was not completely soluble initially, but as the reaction progressed the solution became homogeneous. The solution was then hydrogenated at 40 psig for 16h at room temperature. After the hydrogen uptake ceased, the vessel was opened and the solution concentrated in vacuo to give a yellow solid. The crude product was then taken up in ethyl acetate and washed three times with sat. aq. NaHCO$_3$ solution. The combined aqueous extracts were acidified to pH=1 with 3 N HCl and then extracted three times with ethyl acetate. The combined ethyl acetate extracts were washed with brine, dried over anhyd. MgSO$_4$, filtered and concentrated to give the expected product as a white solid, 4.81 g, 95%. This material was recrystallized from a mixture of methyl ethyl ketone/hexane to give 3.80 g, 75% of pure product, [a]$_D$@25° C.=+11.6° (c=1. 572, MeOH). $^1$H nmr (CDCl$_3$) 300MHz 11.9 (brs, 1H), 7.18 (d, J=9.2Hz, 2H), 6.82 (d, J=9.2Hz, 2H), 6.68 (brt, J=5.6Hz, 1H), 4.33(d, J=5.6Hz, 2H), 3.77(s, 3H), 2.92(ddq, J=7.9, 5.4, 7.3Hz, 1H), 2.60(dd, J=5.4, 15.0Hz, 1H), 2.30(dd, J=7.9, 15.0Hz, 1H), 1.22(d, J=7.3Hz, 3H). cl Butanediamide, N'-[3-[[[(1,1-dimethylethyl)amino]carbonyl] (3-methylbutyl)amino]-2-hydroxy-1-(phenylmethyl)propyl]-N-4-methoxyphenylmethyl-2-methyl,

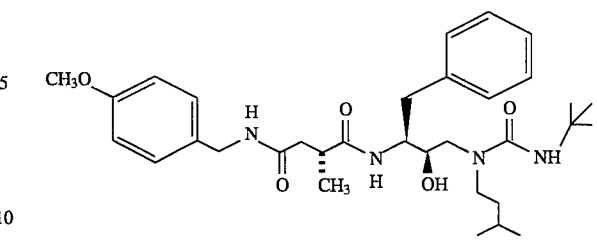

A 50 mL round bottomed flask was charged with 2(R)-methyl 4-N(4-methoxybenzyl) succinamide (588 mg, 2.35 mmol), N-hydroxybenzotriazole (511 mg, 3.34 mmol) and 6 mL of DMF. The solution was cooled to 0° C. and treated with 1-(3-dimethylaminopropyl)-3-ethylcarbodiimide hydrochloride (502 mg, 2.62 mmol) for 20 m. A solution of (2R,3S)-3-amino- 1-(3-methylbutyl)-1-[(1,1-dimethylethyl) amino]carbonyl)-4-phenyl-2-butanol (782 mg, 2.24 mmol) in 2 mL of DMF was added and the solution stirred at room temperature for a period of 24 h. The solution was concentrated in vacuo and poured into 50 mL of 50% sat. aq. NaHCO$_3$, the aqueous phase was extracted with CH$_2$Cl$_2$. The organic phase was washed with 5% citric acid, NaHCO$_3$, brine, dried over anhyd. MgSO$_4$, filtered and concentrated to give an oil that was purified by radial chromatography on SiO$_2$ eluting with hexane/ethyl acetate to give 790 mg, 59% of pure product as a white foam.

Butanediamide,
N'-[3-[[[(1,1-dimethylethyl)amino]carbonyl]
(3-methylbutyl)amino]-2-hydroxy-1-(phenylmethyl)
propyl]-N-phenylmethyl- 2-methyl, [1S-[1R*(2R*(, 2S*]]-

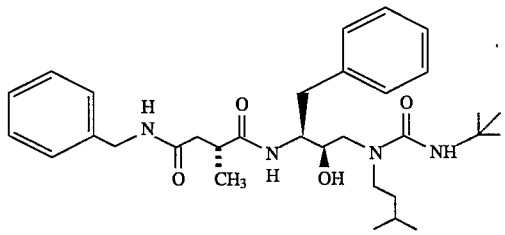

A 50 mL round bottomed flask was charged with 2(R)-methyl 4-N-(benzyl) succinamide (243 mg, 1.1 mmol), N-hydroxybenzotriazole (213 mg, 1.39 mol) and 3 mL of DMF. The solution was cooled to 0° C. and treated with 1-(3-dimethylaminopropyl)- 3-ethylcarbodiimide hydrochloride (228 mg, 1.17 mol) for 20 m. A solution of (2R,3S)-3-amino-1-( 3-methylbutyl)-1-[(1,1-dimethylethyl)amino]carbonyl)-4-phenyl- 2-butanol (327 mg, 0.95 mol) in 2 mL of DMF was added and the solution stirred at room temperature for a period of 24 h. The solution was concentrated in vacuo and poured into 50 mL of 50% sat. aq. NaHCO$_3$, the aqueous phase was extracted with CH$_2$Cl$_2$. The organic phase was washed with 5% citric acid, NaHCO$_3$, brine, dried over anhyd. MgSO$_4$, filtered and concentrated to give an oil that was purified by flash chromatography on SiO$_2$ eluting with hexane/ethyl acetate to give 370 mg, 70% of pure product as a white foam.

EXAMPLE 29

Following the procedure generally as set forth in Example 28, as well as in Examples 31–45, the compounds shown in Table 14 were prepared.

TABLE 14

[Structure: R34R33>X'—C(O)—C(R31)(R1)(R30)(R32)—C(O)—NH—CH(CH2Ph)—CH(OH)—CH2—N(isobutyl)—C(O)—NH—tBu]

| R¹ | R³⁰ | R³¹ | R³² | X' | R³³ | R³⁴ |
|---|---|---|---|---|---|---|
| H | H | H | H | N | H | H |
| H | H | H | H | O | H | — |
| H | H | H | H | O | CH₃ | — |
| CH₃ | H | H | H | N | H | H |
| CH₃ | H | H | H | O | H | — |
| H | H | CH₃ | H | N | H | H |
| H | H | CH₃ | H | O | H | — |
| CH₃ | CH₃ | H | H | N | H | H |
| CH₃ | CH₃ | H | H | O | H | — |
| CH₃ | CH₃ | H | H | O | CH₂C₆H₄OCH₃ | — |
| H | H | CH₃ | CH₃ | N | H | H |
| H | H | CH₃ | CH₃ | O | H | — |
| H | H | CH₃ | CH₃ | O | CH₂C₆H₄OCH₃ | — |
| CH₃ | H | CH₃ | H | N | H | H |
| CH₃ | H | CH₃ | H | N | H | CH₃ |
| CH₃ | H | CH₃ | H | N | CH₃ | CH₃ |
| CH₃ | H | CH₃ | H | O | H | — |
| CH₃ | H | CH₃ | H | N | H | —CH₂C₆H₅OCH₃ |
| OH | H | H | H | N | H | H |
| OH | H | H | H | O | H | — |
| H | H | OH | H | N | H | H |
| H | H | OH | H | O | H | — |
| CH₂CH₂C(O)NH₂ | H | H | H | N | H | H |
| CH₂C(O)NH₂ | H | H | H | N | H | H |
| CH₂C(O)NH₂ | H | H | H | O | H | — |
| CH₂C(O)NH₂ | H | H | H | O | CH₃ | — |
| CH₂Ph | H | H | H | N | H | H |
| CH₃ | H | CH₃ | CH₃ | N | H | H |
| CH₃ | H | CH₃ | CH₃ | O | H | — |
| CH₃ | H | CH₃ | CH₃ | N | H | CH₃ |
| CH₃ | H | CH₃ | CH₃ | N | CH₃ | CH₃ |

EXAMPLE 30

Following the procedure generally as set forth in Example 28, as well as Examples 31–45, the compounds shown in Table 15 were prepared.

TABLE 15

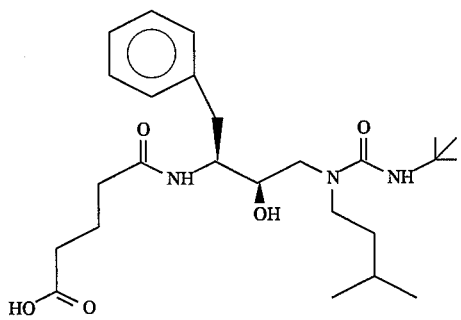

TABLE 15-continued

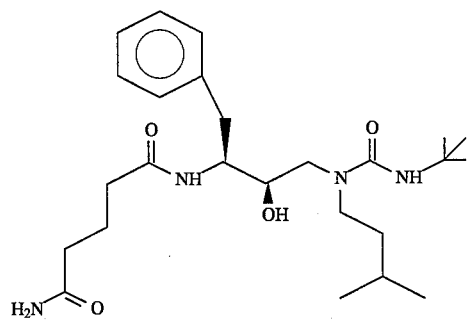

TABLE 15-continued

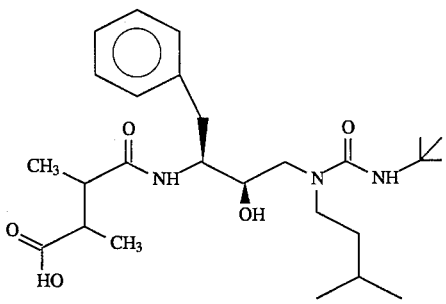

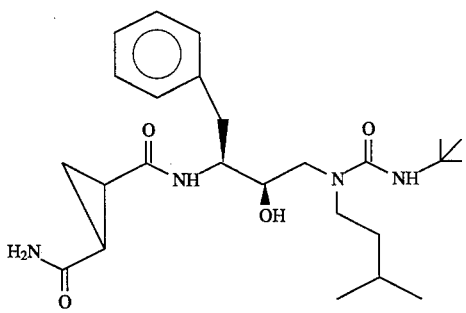

EXAMPLE 31

Preparation of 3 (S)-[N-(2-quinolinylcarbonyl)-L-asparaqinyl]amino-2(R)-hydroxy-4-phenylbutylamine, N-(3-methylbutyl),

Part A

Preparation of N-3(S)-(Benzyloxycarbonyl)-amino- 2(R)-hydroxy-4-phenylbutylamine, N-(3-methylbutyl). A solution of 20 g (67 mmol) of N-benzyloxycarbonyl-3(S)-amino- 1,2-(S)-epoxy-4-phenylbutane in 140 mL of isopropyl alcohol was treated with 83 g (952 mmol) of isoamylamine and refluxed for one hour. The solution was cooled, concentrated, hexane added and the resulting solid filtered to afford 22.4 g of the desired product.

Part B

Preparation of N-3(S)-(Benzyloxycarbonyl)-amino- 2(R)-hydroxy-4-phenylbutylamine, N-(3-methylbutyl)-N-(t-butyloxycarbonyl). To a solution of 22.4 g (58.3 mmol) of product from Part A above, 6.48 g (64.1 mmol) of triethylamine and 150 mg of N,N-dimethyl-4-aminopyridine in 200 mL of tetrahydrofuran at 0° C. was added 12.7 g (58.3 mmol) of di-t-butylpyrocarbonate in 10 mL of THF. After 3.5 hours at room temperature, the volatiles were removed, ethyl acetate added and washed with 5% citric acid, sat'd NaHCO$_3$, dried and concentrated to afford 30 g of crude product. Chromatography on silica gel using 20% ethyl acetate/hexane afforded 22.5 g (79%) of the desired product.

Part C

Preparation of N-3(S)-[N-benzyloxycarbonyl-L-asparaginyl] amino-2(R)-hydroxy-4-phenylbutylamine, N-( 3-methylbutyl)-N-(t-butyloxycarbonyl). A solution of 22.5 g of product from Part B above in 200 mL of ethanol was hydrogenated over 5.9 g of 10% palladium-on-carbon under 50 psig hydrogen for one hour. The catalyst was filtered and the solvent removed under reduced pressure to afford 15.7 g of free amine. This was dissolved in 130 mL of DMF and 4.54 g (44.9 mmol) of N-methylmorpholine an added to a mixture of 13.3 g (49.9 mmol) N-benzyloxy-carbonyl-L-asparagine, 11.5 g (74.9 mmol) of N-hydroxybenzotriazole and 10.5 g (54.9 mmol) of EDCl in 120 mL of DMF at 0° C., which had been preactivated for one hour prior to the addition. The mixture was stirred for 2 hours at 0° C. and then for 12 hours at room temperature. The reaction was poured into 1L of sat'd aqueous sodium bicarbonate, the solid collected, dissolved in ethyl acetate, washed with water, sat'd sodium bicarbonate, 5% citric acid and brine, dried and concentrated to afford 16.7 g of the desired product.

Part D

Preparation of N-3(S)-[N-(2-quinolinylcarbonyl)-L-asparaginyl]amino- 2(R)-hydroxy-4-phenylbutylamine, N-(3-methylbutyl)-N-(t-butyloxycarbonyl). A solution of 16.7 g (28.0 mmol) of product from Part C in 250 mL of methanol was hydrogenated over 6.0 g of 10% palladium-on-carbon and under 50 psig hydrogen for one hour. The catalyst was filtered and the solution concentrated to afford 10.0 g of free amine. This was dissolved in 100 mL of methylene chloride, 4.35 g (43 mmol) of N-methylmorpholine was added followed by 5.53 g (20.5 mmol) of quinoline-2-carboxylic acid, N-hydroxysuccinimide ester. This was stirred at room temperature overnight, the solvent removed, ethyl acetate added and washed with 5% citric acid, sat'd sodium bicarbonate, brine, dried and concentrated to afford 14 g of crude product. Recrystallization from ethyl acetate and hexane afforded 10.5 g (83%) of desired product.

Part E

Preparation of N-3(S)-[N-(2-quinolinylcarbonyl)-L-asparaginyl] amino-2(R)-hydroxy-4-phenylbutylamine, N-(3-methylbutyl). To 80 mL of 4N hydrochloric acid in dioxane was added 9.17 g (14.8 mmol) of product from Part D above. After one hour, the product becomes gummy. The solvents were removed, diethyl ether added and removed and the residue dissolved in 20 mL of methanol. This solution was added to 400 mL of sat'd aqueous sodium bicarbonate, the solids collected, washed with acetone and hexane and dried in vacuo over P$_2$O$_5$ to afford 4.75 g of the desired product.

EXAMPLE 32A

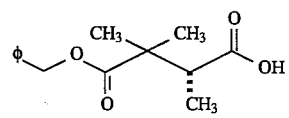

Preparation of Benzyl 2,2,3(R)-trimethylsuccinate

Part A

Preparation of Methyl (S)-lactate, 2-methoxy-2-propyl ether. To a mixture of methylI(s)-(−)-lactate (13.2 g, 100 mmol) and, 2-methoxypropene (21.6 g, 300 mmol) in CH$_2$Cl$_2$ (150 ml) was added POCl$_3$ (7 drops) at r.t. and the resulting mixture was stirred at this temperature for 16 hours. After the addition of Et$_3$N (10 drops), the solvents were removed in vacuo to give 20.0 g of (98%) desired product.

Part B

Preparation of 2(S)-hydroxypropanal, 2-methoxy- 2-propyl ether. To a solution of compound from Part A (20.0 g) in $CH_2Cl_2$ (100 ml) was added DIBAL (65 ml of 1.5M solution in toluene, 97.5 mmol) dropwise at −78° C. for 45 min., then stirring was continued at the temperature for another 45 min. To this cold solution was added MeOH (20 ml), saturated NaCl solution (10 ml) and allowed the reaction mixture to warmup to r.t. and diluted with ether (200 ml), $MgSO_4$ (150 g) was added and stirred for another 2 h. The mixture was filtered and the solid was washed twice with ether. The combined filtrates were rotavaped to afford 11.2 g (78%) of the desired aldehyde.

Part C

Preparation of 2(S)-hydroxy-cis-3-butene, 2-methoxy-2-propyl ether. To a suspension of ethyltriphenylphosphoniumbromide (28 g, 75.5 mmol) in THF (125 ml) was added $KN(TMS)_2$ (15.7 g, 95%, 75 mmol) in portions at 0° C. and stirred for 1 h at the temperature. This red reaction mixture was cooled to −78° C. and to this was added a solution of aldehyde from Part B (11 g, 75 mmol) in THF (25 ml). After the addition was completed, the resulting reaction mixture was allowed to warmup to r.t. and stirred for 16 h. To this mixture was added saturated $NH_4Cl$ (7.5 ml) and filtered through a pad of celite with a thin layer of silica gel on the top. The solid was washed twice with ether. The combined filtrates were concentrated in vacuo to afford 11.5 g of crude product. The purification of crude product by flash chromatography (silica gel, 10:1 Hexanes/EtoAc) affording 8.2 g (69%) pure alkene.

Part D

Preparation of 2(S)-hydroxy-cis-3-butene. A mixture of alkene from Part C (8.2 g) and 30% aqueous acetic acid (25 ml) was stirred at r.t. for 1 hour. To this mixture was added $NaHCO_3$ slowly to the pH ∼7, then extracted with ether (10 ml×5). The combined ether solutions were dried $(Na_2SO_4)$ and filtered. The filtrate was distilled to remove the ether to give 2.85 g (64%) pure alcohol, m/e=87(M+H).

Part E

Preparation of 2,2,3-trimethyl-hex-(trans)-4-enoic acid. To a mixture of alcohol from Part D (2.5 g, 29 mmol) and pyridine (2.5 ml) in $CH_2Cl_2$ (60 ml) was added isobutyryl chloride (3.1 g, 29 mmol) slowly at 0° C. The resulting mixture was stirred at r.t. for 2 hours then washed with $H_2O$ (30 ml×2) and sat. NaCl (25 ml). The combined organic phases were dried $(Na_2SO_4)$, concentrated to afford 4.2 g (93%) ester 2(S)-hydroxy-cis-3-butenyl isobutyrate. This ester was dissolved in THF (10 ml) and was added to a 1.0M LDA soln. (13.5 ml of 2.0M LDA solution in THF and 13.5 ml of THF) slowly at −78° C. The resulting mixture was allowed to warmup to r.t. and stirred for 2 h and diluted with 5% NaOH (40 ml). The organic phase was separated, the aqueous phase was washed with $Et_2O$ (10 ml). The aqueous solution was collected and acidified with 6N HCl to pH ∼3. The mixture was extracted with ether (30 ml× 3). The combined ether layers were washed with sat. NaCl (25 ml), dried $(Na_2SO_4)$ and concentrated to afford 2.5 g (60%) of desired acid, m/e=157(M+H).

Part F

Preparation of benzyl 2,2,3 (S)-trimethyl-trans- 4-hexenoate. A mixture of acid from Part E (2.5 g, 16 mmol), BnBr (2.7 g, 15.8 mmol), $K_2CO_3$ (2.2 g, 16 mmol), NaI (2.4 g) in acetone (20 ml) was heated at 75° C. (oil bath) for 16 h. The acetone was stripped off and the residue was dissolved in $H_2O$ (25 ml) and ether (35 ml). The ether layer was separated, dried $(Na_2SO_4)$ and concentrated to afford 3.7 g (95%) of benzyl ester, m/e=247 (M+H).

Part G

Preparation of benzyl 2,2,3(R)-trimethylsuccinate. To a well-stirred mixture of $KMnO_4$ (5.4 g, 34, 2 mmol), $H_2O$ (34 ml), $CH_2Cl_2$ (6 ml) and benzyltriethylammonium chloride (200 mg) was added a solution of ester from Part F (2.1 g, 8.54 mmol) and acetic acid (6 ml) in $CH_2Cl_2$ (28 ml) slowly at 0° C. The resulting mixture was stirred at the temperature for 2 h then r.t. for 16 h. The mixture was cooled in an ice-water bath, to this was added 6N HCl (3 ml) and solid $NaHSO_3$ in portions until the red color disappeared. The clear solution was extracted with $CH_2Cl_2$ (30 ml×3). The combined extracts were washed with sat. NaCl solution, dried $(Na_2SO_4)$ and concentrated to give an oil. This oil was dissolved in $Et_2O$ (50 ml) and to this was added sat. $NaHCO_3$ (50 ml). The aqueous layer was separated and acidified with 6N HCl to pH ∼3 then extracted with $Et_2O$ (30 ml×3). The combined extracts were washed with sat. NaCl solution (15 ml), dried $(Na_2SO_4)$ and concentrated to afford 725 mg (34%) of desired acid, benzyl 2,2,3 (R)-trimethylsuccinate, m/e=251 (M+H).

EXAMPLE 32B

Part A:

Preparation of Butanediamide, $N^1$[3-[[[(1,1-dimethylethyl)amino]carbonyl](3-methylbutyl)amino]-2-hydroxy-1-(phenylmethyl)propyl]-2,3,3-trimethyl-[1S-, [1R*(2S*),2S*]]-

To a well-stirred solution of benzyl 2,2,3(R)-trimethylsuccinate (225 mg, 0.9 mmol) in DMF (1.0 ml) was added HOBt (230 mg, 1.5 mmol). The clear reaction mixture was then cooled to 0° C., to this was added EDC (210 mg, 1.1 mmol) and stirred for 1 h at the temperature. To this cold mixture was added a powder of (350 mg, 1.0 mmol) and DMF (0.5 ml). The resulting reaction mixture was stirred for 2 h at 0° C. and 16 h at r.t. After the removal of DMF (≦ 40° C.), a solution of 60% sat. $NaHCO_3$ (10 ml) was added. This mixture was extracted with EtOAc (10 ml×2). The extracts were combined and washed with sat. $NaHCO_3$ (10 ml× 2), 5% citric acid (10 ml×2), $H_2O$ (10 ml), sat. NaCl (10 ml) and dried $(Na_2SO_4)$ then concentrated to afford 512 mg (98%) of desired product Butanoic Acid, 4-[[3-[[ [(1,1-dimethylethyl)amino]carbonyl]( 3-methylbutyl)amino]-2-hydroxy-1-(phenylmethyl)propyl]amino]-2,2,3-trimethyl-4-oxo, [1S-[1R*(3S*),2S*]]-benzyl ester as a white solid, m/e=582 (M+H).

Part B

A mixture of benzyl ester from Part A (480 mg, 0.825 mmol), 10% Pd/C (450 mg) in MeOH (25 ml) was hydrogenated ($H_2$, 50 psi) for ½ h at r.t. The mixture was filtered and the solid was washed with MeOH (10 ml). The collected filtrates were concentrated to afford a crude acid as a white solid. The crude acid was dissolved in Et$_2$O-EtOAc (10:1, 25 ml) and the solution was washed with sat. NaHCO$_3$ (25 ml) then 5% NaOH (10 ml). The combined aqueous layers were cooled to 0° C. and acidified with concentrated HCl (Co$_2$) to pH ~1 then extracted with Et$_2$O-EtOAC (10:1, 25 ml×3). The combined extracts were washed with sat. NaCl (15 ml), dried (Na$_2$SO$_4$) and concentrated to afford 307 mg (75.7%) of pure acid Butanoic acid, 4-[[3-[ [[(1,1-dimethylethyl)amino]carbonyl](3-methylbutyl)amino]- 2-hydroxy-1-(phenylmethyl)propyl]amino]-2,2,3-trimethyl-4-oxo-, [1S-[1R*(3S*),2S*]]-, as a white solid, m/e=491(M+H).

Part C

Butanoic acid, 4-[[3-[[[(1,1-dimethylethyl)amino] carbonyl](3-methylbutyl)amino]-2-hydroxy- 1-(phenylmethyl)propyl]amino]-2,2,3-trimethyl-4-oxo-, [1S-[1R*(3S*),2S*]]-, as a white solid, m/e=491(M+H).

To a well-stirred solution of the acid from Part B (245 mg, 0.5 mmol) in DMF (0.5 ml) was added HOBt (153 mg, 1.0 mmol) and EDC (143 mg, 0.75 mmol) at 0° C. After stirring at 0° C. for 2 h, NH$_4$OH (0.63 ml of 28% NH$_4$OH, 5 mmol) was added and stirred at 0° C. for 2 h, r.t. for 16 h. The removal of DMF (≦40° C.) gave a white solid. The purification of the crude product by flash chromatography (silica gel, 5% MeOH/CH$_2$Cl$_2$) gave 172 mg (70%) of pure amide as a white solid, m/e=491(M+H).

EXAMPLE 33

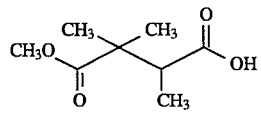

Preparation of methyl 2,2-dimethyl-3-methyl succinate, (R) and (S) isomers,

Part A

Preparation of methyl 2,2-dimethyl-3-oxo-butanoate. A 250 ml RB flask equipped with magnetic stir bar and N$_2$ inlet was charged with 100 ml dry THF and 4.57 g (180 mmol) of 95% NaH. The slurry was cooled to −20° C. and 10 g (87 mmol) methyl acetoacetate was added dropwise followed by 11.3 ml (181 mmol) CH$_3$I. The reaction was stirred at 0° C. for 2 hours and let cool to room temperature overnight. The reaction was filtered to remove NaI and diluted with 125 ml Et$_2$O. The organic phase was washed with 1×100 15% brine, dried and concentrated in vacuo to a dark golden oil that was filtered through a 30 g plug of silica gel with hexane. Concentration in vacuo yielded 10.05 g of desired methyl ester, as a pale yellow oil, suitable for use without further purification.

Part B

Preparation of methyl 2,2-dimethyl-3-O-(trifluoromethanesulfonate)-but- 3-enoate. A 250 ml RB flask equipped with magnetic stir bar and N2 inlet was charged with 80 mL by THF and 5.25 ml (37.5 mmol) diisopropylamine was added. The solution was cooled to −25° C. (dry ice/ethylene glycol) and 15 ml (37.5 mmol) of 2.5 M n-BuLi in hexanes was added. After 10 minutes a solution of 5 g (35 mmol) 1 in 8 ml dry THF was added. The deep yellow solution was stirred at −20° C. for 10 min. then 12.4 g N-phenyl bis(trifluoromethanesulfonimide) (35 mmol) was added. The reaction was stirred @−10° C. for 2 hours, concentrated in vacuo and partioned between ethyl acetate and sat. NaHCO$_3$. The combined organic phase was washed with NaHCO$_3$, brine and conc. to an amber oil that was filtered through 60 g silica gel plug with 300 mL 5% ethyl acetate/hexane Conc. in vacuo yielded 9.0 g light yellow oil that was diluted with 65 ml ethyl acetate and washed with 2×50 ml 5% aq K$_2$CO$_3$, 1×10 mL brine, dried over Na$_2$SO$_4$ and conc. in vacuo to yield 7.5 g (87%) vinyl triflate, (m/e=277(M+H) suitable for use without further purification.

Part C

Preparation of methyl 2,2-dimethyl-3-carboxyl-but-3-enoate. A 250 ml Fisher Porter bottle was charged with 7.5 g (27 mmol) of compound prepared in B, 50 ml dry DMF, 360 mg (1.37 mmol) triphenyl phosphine and 155 mg (0.69 mmol) Pd(II)(OAc)$_2$. The reaction mixture was purged twice with N$_2$ then charged with 30 psi CO. Meanwhile a solution of 20 ml dry DMF and 7.56 ml (54 mmol) NEt$_3$ was cooled to 0° C. to this was added 2.0 g (43 mmol) of 99% formic acid. The mixture was swirled and added to the vented Fisher Porter tube. The reaction vessel was recharged to 40 psi of CO and stirred 6 hours @room temperature. The reaction mixture was concentrated in vacuo and partionned between 100 mL of ethyl acetate and 75 mL 5% aq K$_2$CO$_3$. The aqueous phase was washed with 1×40 mL additional ethyl acetate and then acidified with conc. HCl/ice. The aqueous phase was extracted with 2×70 mL of ethyl acetate and the organics were dried and conc. to yield 3.5 g (75%) white crystals, mp 72°–75° C., identified as the desired product (m/e=173(M+H).

Part D

Preparation of methyl 2,2-dimethyl-3-methylsuccinate, isomer #1. A steel hydrogenation vessel was charged with 510 mg (3.0 mmol) acrylic acid, from Part C, and 6 mg Ru (acac)$_2$ (R-BINAP) in 10 ml degassed MeOH. The reaction was hydrogenated at 50 psi/room temperature for 12 hours. The reaction was then filtered through celite and conc. to 500 mg clear oil which was shown to be a 93:7 mixture of isomer #1 and #2, respectively as determined by GC analysis using a 50 M β-cyclodextrin column: 150° C. −15 min. then ramp 2° C./min.; isomer #1, 17.85 min., isomer #2, 18–20 min.

Part E

Preparation of methyl 2,2-dimethyl-3-methylsuccinate, Isomer #2. A steel hydrogenation vessel was charged with 500 mg (2.9 mmol) acrylic acid, Part C, and 6 mg Ru(OAc)(acac)(S-BINAP) in 10 ml degassed MeOH. The reaction was hydrogenated at 50 psi/room temperature for 10 hours. The reaction was filtered through celite and concentrated in vacuo to yield 490 mg of product as a 1:99 mixture of isomers #1 and #2, respectively, as determined by chiral GC as above.

In a similar manner, one can use benzyl 2,2-dimethyl-3-oxo-butanoate to prepare benzyl 2,2,3trimethylsuccinate, R and S isomers.

EXAMPLE 34

Preparation of
3-[[[(1,1-dimethylethyl)amino]carbonyl-(3-methylbutyl)amino]-
2(R)-hydroxy-1(S)-(phenylmethyl)propylamine, 1.

Part A

To a solution of 75.0 g (0.226 mol) of N-benzyloxycarbonyl-L-phenylalanine chloromethyl ketone in a mixture of 807 mL of methanol and 807 mL of tetrahydrofuran at −2° C., was added 13.17 g (0. 348 mol, 1.54 equiv.) of solid sodium borohydride over one hundred minutes. The solvents were removed under reduced pressure at 40° C. and the residue dissolved in ethyl acetate (approx. 1L). The solution was washed sequentially with 1M potassium hydrogen sulfate, saturated sodium bicarbonate and then saturated sodium chloride solution. After drying over anhydrous magnesium sulfate and filtering, the solution was removed under reduced pressure. To the resulting oil was added hexane (approx. 1L) and the mixture warmed to 60° C. with swirling. After cooling to room temperature, the solids were collected and washed with 2L of hexane. The resulting solid was recrystallized from hot ethyl acetate and hexane to afford 32.3 g (43% yield) of N-benzyloxycarbonyl-3(S)-amino- 1-chloro-4-phenyl-2(S)-butanol, mp 150°–151° C. and M+Li$^+$=340.

Part B

To a solution of 6.52 g (0.116 mol, 1.2 equiv.) of potassium hydroxide in 968 mL of absolute ethanol at room temperature, was added 32.3 g (0.097 mol) of N-CBZ-3(S)-amino- 1-chloro-4-phenyl-2(S)-butanol. After stirring for fifteen minutes the solvent was removed under reduced pressure and the solids dissolved in methylene chloride. After washing with water, drying over magnesium sulfate, filtering and stripping, one obtains 27.9 g of a white solid. Recrystallization from hot ethyl acetate and hexane afforded 22.3 g (77% yield) of N-benzyloxycarbonyl- 3(S)-amino-1, 2(S)-epoxy-4-phenylbutane, mp 102°–103° C. and MH+298.

Part C

A solution of N-benzyloxycarbonyl 3 (S)-amino- 1,2-(S)-epoxy-4-phenylbutane (30.1 g, 0.10 mol) and 165mL of isoamylamine in 150 mL of isopropyl alcohol was heated to reflux for 2.5 hours. The solution was cooled to room temperature, concentrated in vacuo and then recrystallized. The product was isolated by filtration and from ethyl acetate/hexane to afford 31.7 g (81%) of N[3(S)-benzyloxycarbonylamino- 2(R)-hydroxy-4-phenylbutyl]N-isoamylamine.

Part D

A solution of N [3 (S)-benzyloxycarbonylamino- 2 (R)-hydroxy-4-phenyl butyl], N-isoamylamine in 10 ml of tetrahydrofuran was treated with tert-butylisocyanate (267 mg, 2.70 mmol) at room temperature for 5 minutes. The solvent was removed in vacuo and replaced with ethyl acetate. The ethyl acetate solution was washed with 5% citric acid, water, and brine, dried over anhydrous MgSO$_4$, filtered and concentrated in vacuo to give 1.19 g, 97% of N-benzyloxycarbonyl- 3-[[[(1,1-dimethylethyl)amino]carbonyl]( 3-methylbutyl)amino]-2(R)-hydroxy-1(S)-(phenylmethyl)propylamine, MH+m/z=470.

Part E

A solution of (37.3 g, 77 mmol) of product from Part D in 100 mL of methanol was hydrogenated over 10% palladium-on-carbon for 4 hours to afford 26.1 g of the desired product.

EXAMPLE 35

Preparation of Butanediamide,
N-[3-[[[(1,1-dimethylethyl)amino]
carbonyl](3-methylbutyl)amino]-2-hydroxy-
1-(phenylmethyl)propyl]-, [1S-[1R*, 2S*]]-.

Part A

To a solution of 102mg (0.29 mmol) of Example 34 Part E and 70 mg (0.89 mmol) of pyridine in 2 mL of methylene chloride was added 29 mg (0.29 mmol) of succinic anhydride. After 2 hours, ethyl acetate was added and then extracted with saturated NaHCO. The aqueous layer was acidified, reextracted with ethyl acetate, washed with saturated brine, dried over magnesium sulfate, filtered and concentrated in vacuo to afford 78 mg (60%) of butanoic acid, 4-[[3-[[[(1,1-dimethylethyl)amino]carbonyl](3-methylbutyl)amino]- 2-hydroxy-1-(phenylmethyl)propyl]amino-4-oxo-, [1S-[1R*, 2S*]-.

Part B his was activated with EDC and N-hydroxybenzotriazole in N, N-dimethylformamide and then reacted with ammonia to generate the desired final compound.

EXAMPLE 36

Part A

To a solution of 4.60 g (24.7 mmol) of trans-diethyl 1,2-cyclopropanedicarboxylate in 100 mL of 50:50 v:v tetrahydrofuran/water was added 1.24 g (29.6 mmol) of lithium hydroxide. After 17 hours, the tetrahydrofuran was removed in vacuo, the water layer washed with ethyl acetate, acidified with 1N hydrochloric acid and reextracted with ethyl acetate. The organic layer was dried and stripped to afford 2.1 g of crude product. After recrystallization from diethyl ether/hexane and then methylene chloride/hexane one obtains 1.1 g (28%) of trans-monoethyl-1,2-cyclopropanedicarboxylate, m/e=159 (M+H).

Part B

To a solution of 297 mg (1.87 mmol) of trans-monoethyl 1,2-cyclopropanedicarboxylate and 429 mg (2.8 mmol) N-hydroxybenzotriazole (HOBT) in 3 mL of anhydrous N,N-dimethylformamide (DMF) at 0° C. was added 394 mg (2.0 mmol) of 1-(3-dimethylaminopropyl)-3-ethylcarbodiimide hydrochloride (EDC). After 30 min. a solution of 591 mg (1.7 mmol) of product from Part A in 2 mL DMF and 171 mg (1.69 mmol) of N-methylmorpholine (NMM) was added. After 2 hours at 0° C., the reaction was stirred at RT overnight, poured into water, extracted with ethyl acetate, washed with water, 5% aq. citric acid, sat'd NaHCO$_3$, brine, dried over anhydride MgSO$_4$ and stripped to afford 771 mg of crude product. This was chromatographed on silica gel using 5– 20% methanol/methylene chloride to afford 670 mg (80%) of cyclopropane carboxylic acid, 2-[[[3-[[[(1,1-dimethylethyl)amino]carbonyl]( 3-methylbutyl)amino]-2-hydroxy- 1-(phenylmethyl)propyl]amino]carbonyl]-, ethyl ester; m/e=490 (M+H).

Part C

To a solution of 658 mg (1.32 mmol) of product from Part B in 5 mL of 50:50 THF/water was added 66 mg (1.58 mmol) of lithium hydroxide. After 19 hours, the THF was removed in vacuo, the water washed with ethyl acetate, acidified and reextracted with ethyl acetate. The organic layer was dried and stripped to afford 328 mg (54%) of the corresponding acid, m/e=462 (M +H).

Part D

To a solution of 304 mg (0.66 mmol) of product from Part C, 151 mg (0.99 mmol) HOBT in 2.2 mL DMF at 0° C. was added 139 mg (0.73 mmol) EDC. After 30 min. at 0° C., 1.1 mL of conc. aqueous ammonia was added. After stirring at 0° C. for 2 hours and RT for 20 hours, the reaction was poured into brine and extracted with ethyl acetate. After washing with sat'd NaHCO$_3$, brine, drying and stripping, one obtains 141 mg of crude product. This was chromatographed on silica gel with 1–5% methanol/methylene chloride to afford 40 mg (13%) of the desired final product, m/e=561 (M+H).

EXAMPLE 37

Preparation of trans-but-2-enediamide.
N-[3-[[[(1,1-dimethylethyl)amino]carbonyl]( 3-methylbutyl)amino]-2-hydroxy-
1-(phenylmethyl)propyl]-, [1S-[1R* , 2S*],

Part A

To a solution of 137 mg (0.95 mmol) fumaric acid monoethyl ester in 1 mL of DMF at 0° C. was added 183 mg (0.95 mmol) EDCl. After 15 minutes, a solution of 333 mg (0.95 mmol) of the compound of Example 34 Part E in 1 mL DMF was added and the reaction stirred for 14 hours at RT. Ethyl acetate was added and extracted with sat'd brine, 0.2 n HCl, sat'd NaHCO$_3$, dried and stripped to afford 0.32 g of crude product. Chromatography on silica gel using 0–50% ethyl acetate/hexane afforded 0.26 g (58%) of but-2-enoic acid, 4-[[3-[[[(1,1-dimethylethyl)amino]carbonyl](3-methylbutyl)amino]- 2-hydroxy-1-(phenylmethyl)propyl] amino]- 4-oxo-, [1S-[1R*, 2S*]]-, ethyl ester, m/e=476 (M+H).

Part B

To a solution of 26.6 mg (0.56 mmol) of product from Part A in 3 mL of 50:50 THF/water was added 34 mg (0.82 mmol) of lithium hydroxide and the reaction stirred at RT for 1 hour. The THF was removed in vacuo, the aqueous layer acidified with 1N HCl and extracted with ethyl acetate. The organic layer was washed with brine, dried and stripped to afford 233 mg (93%) of trans-but-2-enoic acid, 4-[[3-[[[(1, 1-dimethylethyl)amino]carbonyl](3-methylbutyl)amino]-2-hydroxy-1-(phenylmethyl)propyl]amino]- 4-oxo-, [1S-[1R*, 2S*]-, m/e=448 (M+H).

Part C

To a solution of 225 mg (0.50 mmol) of the product from Part B in 1 mL of DMF was added 95 mg (0.50 mmol) EDC. After 15 minutes at RT, 0.50 mL of conc. aqueous ammonia was added and the reaction stirred for 15 hours. Ethyl acetate was added and washed with 0.2N HCl, brine, dried and stripped to afford 170 mg of crude product. After chromatography on silica gel using 0–40% methanol/methylene chloride, one obtains 50 mg (22%) of trans-but-3-enediamide, N-[3-[[[(1,1-dimethylethyl)amino]carbonyl]( 3-methylbutyl)amino]-2-hydroxy- 1-(phenylmethyl)propyl]-, [1S-[1R*, 2S*]-, m/e= 447 (M+H).

EXAMPLE 38

Preparation of butanediamide,
N-[3-[[[(1,1-dimethylethyl)amino]
carbonyl](3-methylbutyl)amino]-2-hydroxy-
1-(phenylmethyl)propyl-2-methyl-, [1S-[1R*(2S*),
2S*]-,

Part A

To a suspension of 24.7 g (0.22 mol) of itaconic anhydride in 100 mL of anhydrous toluene at reflux under a nitrogen atmosphere was added dropwise over 30 minutes 23.9 g (0.22 mol) of benzyl alcohol. The insoluble material dissolved to provide a homogeneous solution which was refluxed for 1.5 hours. The solution was cooled to RT, then in an ice bath and the resulting white precipitate collected by filtration to afford 24.8 g (51%) of 4-benzyl itaconate.

Part B

To a solution of 2.13 g (9.5 mmol) of the product from Part A in 12 mL of methylene chloride at 0° C. was added 4.02 g (29.1 mmol) of para-methoxybenzyl alcohol, 605 mg (4.95 mmol) of N,N-dimethyl 4-aminopyridine, 128 mg of N,N-dimethyl 4-aminopyridine hydrochloride salt and then 2.02 g (4.7 mmol) dicyclohexylcarbodiimide (DCC). After stirring at 0° C. for 1 hour and then RT for 2 hours, the precipitate was collected and discarded. The filtrate was washed with 0.5 N HCl, sat'd NaHCO$_3$, dried and stripped to afford 4.76 g of crude product. This was chromatographed on silica gel using 0–50% ethyl acetate/hexane to afford 1.24 g of pure 4'-methoxybenzyl-4-benzylitaconate.

Part C

A solution of 1.24 g (3.65 mmol) of product from Part B and 20 mg of [(R,R)-Dipanlo)cyclooctadienylrhodium] tetrafluoroborate in 30 mL of methanol was throughly degassed, flushed with nitrogen and then hydrogen and then stirred under 50 psig of hydrogen for 15 hours. The solution was filtered and stripped, dissolved in methylene chloride and washed with sat'd NaHCO$_3$, dried and stripped to afford 0.99 g of a brown oil. This was then dissolved in 40 mL of methylene chloride, 3 mL of trifluoroacetic acid added and the solution stirred at RT for 3.5 hours. Water was added and separated and the organic layer extracted with sat'd NaHCO$_3$. The aqueous layer was acidified and reextracted with ethyl acetate, separated and the organic layer washed with brine, dried and stripped to afford 320 mg (50%) of 2(R)-methyl-4-benzylsuccinic acid.

Part D

To a solution of 320 mg (1.44 mmol) of product from Part C and 314 mg (2.05 mmol) HOBT in DMF at 0° C. was added 303 mg (1.58 mmol) of EDC. After stirring for 30 minutes, a solution of 467 mg (1.34 mmol) of the product from Example 34, Part E in 4 mL of DMF was added. After stirring for 1 hour at 0° C. and 14 hours at RT, ethyl acetate was added and washed with sat'd NaHCO$_3$, 5% aqueous citric acid, dried and stripped to afford 0.97 g of crude product. This was chromatographed on silica gel using 0–10% ethyl acetate/hexane to afford 420 mg of pure butanoic acid, 4-[[3-[[[(1,1-dimethylethyl)amino]carbonyl](3-methylbutyl)amino]-2-hydroxy-1-(phenylmethyl)propyl]amino]-3-methyl-4-oxo-, [1S-[1R*(3S*), 2S*]-, benzyl ester.

Part E

A solution of 150 mg (0.27 mmol) of product from Part D in 15 mL of methanol was hydrogenated over 10% palladium on carbon under 50 psig hydrogen for 17 hours. The reaction was filtered and stripped to afford 125 mg (100%) of butanoic acid, 4-[[3-[[[(1,1-dimethylethyl)amino] carbonyl](3-methylbutyl)amino]-2-hydroxy- 1-(phenylmethyl)propyl]amino]-3-methyl-4-oxo-, [1S-[ 1R*(3S*), 2S*] -.

Part F

To a solution of 125 mg (0.27 mmol) of product from Part E and 65 mg (0.42 mol) of HOBT in 5 mL of DMF at 0° C. was added 59 mg (0.31 mmol) of EDC. After 30 min. at 0° C., 1 mL of conc. aqueous ammonia was added. After stirring at 0° C. for 2 hours and RT fro 15 hours, ethyl acetate was added and washed with sat'd NaHCO$_3$, 5% aqueous citric acid, dried and stripped to afford 90 mg of crude product. This was recrystallized from ethyl acetate/hexane to afford 40 mg (32%) of pure butanediamide, N-[3-[[[(1,1-dimethylethyl)amino] carbonyl](3-methylbutyl)amino]-2-hydroxy- 1-(phenylmethyl)propyl]-2-methyl, [1S-[1R*(2S*), 2S*]-.

EXAMPLE 39

Preparation of butanediamide, N-[3-[[[(1,1-dimethylethyl)amino] carbonyl](3-methylbutyl)amino]-2-hydroxy- 1-(phenylmethyl)propyl]-2-methyl, [1S-[1R*(2R*), 2S*]-, Part A A solution of 1.41 g (4.1 mmol) of 4-methoxybenzyl 4-benzylitaconate and 25 mg of [(S,S-Dipamp)cyclooctadienylrhodium] tetrafluoroborate in 20 mL of methanol was thoroughly degassed, flushed with nitrogen and then hydrogen and then stirred under 40 psig hydrogen for 72 hours. The solution was filtered and concentrated to provide 1.34 g of a brown oil. This was dissolved in 40 mL of methylene chloride and 3 mL of trifluoroacetic acid was added. After stirring for 4 hours, water was added, separated and the organic layer extracted with sat'd NaHCO$_3$. The aqueous layer was separated, reacidified, extracted with ethyl acetate which was separated, washed with brine, dried and stripped to afford 440 mg of 2(S)-methyl- 4-benzylsuccinic acid.

Part B

To a solution of 440 mg (1.98 mmol) of the product from Part A and 437 mg (2.86 mmol) of HoBT in 9 mL of DMF at 0° C. was added 427 mg (2.23 mmol) of EDCl. After 30 minutes at 0° C., a solution of 653 mg (1.87 mmol) of the product from Example 34, Part E in 3 mL DMF was added. After 1 hour at 0° C. and 15 hours at RT, ethyl acetate was added, extracted with sat'd NaHCO$_3$, 5% aqueous citric acid, dried and concentrated to afford 0.98 g of crude product. Chromatography on silica gel using 0–10% ethyl acetate afforded 610 mg (59%) of pure butanoic acid, 4-[[3-[[[(1,1-dimethylethyl)-amino] carbonyl](3-methylbutyl)amino]-2-hydroxy- 1-(phenylmethyl)propyl]amino]-3-methyl-4-oxo-, [1S-[ 1R*(3R*), 2S*], benzyl ester.

Part C

A solution of 310 mg (0.56 mmol) of the product from Part B in 20 mL of methanol was hydrogenated over 20 mg of 10% palladium on carbon under 50 psig hydrogen for 19 hours. The solution was filtered and concentrated to afford 220 mg (85%) of butanoic acid, 4-[[3-[[[(1,1-dimethylethyl)-amino] carbonyl](3-methylbutyl)amino]-2-hydroxy-1-(phenylmethyl)propyl]amino]-3-methyl-4-oxo-, [1S-[ 1R*(3R*), 2S*].

Part D

To a solution of 190 mg (0.41 mmol) of the product from Part C and 90 mg (0.58 mmol) HOBT in 5 mL of DMF at 0° C., was added 88 mg (0.46 mmol) of EDC. After 30 minutes at 0° C., 2 mL of conc. aqueous ammonia was added. After 1 hour at 0° C. and 15 hours at RT, ethyl acetate was added, washed with sat'd NaHCO$_3$, 5% aqueous citric acid, dried and concentrated to afford crude product. Recrystallization from ethyl acetate/hexane afforded 20 mg (11%) of butanediamide, N-[3-[[[(1,1-dimethylethyl)amino] carbonyl](3-methylbutyl)amino]-2-hydroxy- 1-(phenylmethyl)propyl]-2-methyl, [1S-[1R*(2R*), 2S*].

EXAMPLE 40

Preparation of butanediamide, N-[3-[[[(1,1-dimethylethyl)amino] carbonyl](3-methylbutyl)amino]-2-hydroxy- 1-(phenylmethyl)propyl]-3-methyl-, [1S-[1R*(3S*), 2S*]-.

Part A

In a similar manner to the procedure used above, p-methoxybenzyl alcohol was reacted with itaconic anhydride in refluxing toluene to provide 4-(p-methoxybenzyl)itaconate.

Part B

To a solution of 3.30 g (13.2 mmol) of the product from Part A in 17 mL of toluene, was added 2.08 g (13.7 mmol) of 1,8-diazabicyclo[5.40]undec-7-enc and then 2.35 g (13.7 mmol) of benzyl bromide. After 2 hours, the solution was filtered and the filtrate washed with sat'd NaHCO$_3$, 3N HCl, brine, dried and concentrated to afford 3.12 g of an oil. After chromatography on silica gel using 0–5% ethyl acetate/hexane one obtains 2.19 g (49%) of benzyl 4-(4-methoxybenzyl)itaconate.

Part C

A solution of 1.22 g (3.6 mmol) of product from Part B and 150 mg of [((R,R-Dipamp)) cyclooctadienylrhodium] tetrafluoroborate in 15 mL of methanol was thoroughly degassed, flushed with nitrogen and then hydrogen and hydrogenated under 50 psig for 16 hours. The solution was filtered and concentrated to afford 1.2 g of a brown oil. This was dissolved in 5 mL of methylene chloride and 5 mL of toluene and 3 mL of trifluoroacetic acid was added. After 4 hours, the solvents were removed in vacuo, the residue dissolved in methylene chloride, which was then extracted with sat'd NaHCO$_3$. After separation, the aqueous layer was acidified, reextracted with methylene chloride which was then dried and concentrated to afford 470 mg (60%) of 3(R)-methyl-4-benzylsuccinic acid.

Part D

To a solution of 470 mg (2.11 mmol) of product from Part C and 463 mg (3.03 mg) of HOBT in 5 mL of DMF at 0° C. was added 451 mg (2.35 mmol) of EDC. After 30 min. at 0° C., a solution of 728 mg (2.08 mmol) of the product from Example 34, Part E in 3 mL of DMF was added. After stirring at 0° C. for 1 hour and 15 hours at RT, ethyl acetate was added and extracted with sat'd NaHCO$_3$, 5% aqueous citric acid, brine, dried and concentrated to give 930 mg of crude product chromatography on silica gel using 0–10% ethyl acetate/hexane one obtains 570 mg (50%) of butanoic acid, 4-[[3-[[[(1,1-dimethylethyl)amino] carbonyl](3-methylbutyl)amino]-2-hydroxy- 1-(phenylmethyl)propyl]amino] -2-methyl-4-oxo-, [1S-[ 1R*(2S*), 2S*]-, benzyl ester.

Part E

The product was hydrogenated in methanol using 10% palladium on carbon under 40 psig of hydrogen to afford butanoic acid, 4-[[3-[[[(1,1-dimethylethyl)amino]carbonyl]( 3-methylbutyl)amino]-2-hydroxy-1-(phenylmethyl) propyl] amino]-2-methyl-4-oxo-, [1S-[1R*(2S*), 2S*]-.

Part F

To a solution of 427 mg (0.92 mmol) of product from Part E and 210 mg (1.37 mmol) in 3 mL of DMF at 0° C. was added 196 mg (1.02 mmol) of EDC. After 30 min. at 0° C., 2 mL of conc. aqueous ammonia was added. After 1 hour at 0° C. and 15 hours at RT, ethyl acetate was added and then extracted with sat'd NaHCO$_3$, brine, dried and concentrated to afford crude product. Recrystallization from ethyl acetate/ hexane afforded 50 mg (12%) of butanediamide, N-[3-[ [[(1,1-dimethylethyl)amino]carbonyl](3-methylbutyl)amino]- 2-hydroxy-1-(phenylmethyl)propyl]-3-methyl-, [1S-[1R*(3S*), 2S*]-.

EXAMPLE 41

Preparation of butanediamide,
N-[3-[[[(1,1-dimethylethyl)amino]
carbonyl](3-methylbutyl)amino[-2-hydroxy-
1-(phenylmethyl)propyl]-3-methyl-, [1S-[1R*(3R*),
2S*]-, This was prepared in an identical manner to the previous example except that the asymmetric hydrogenation step was done in the presence of [((S,S-dipamp)cyclooctadienyl- )rhodium]-tetrafluoroborate as catalyst.

EXAMPLE 42

Preparation of butanediamide.
N-[3-[[[(1,1-dimethylethyl)amino]
carbonyl](3-methylbutyl) amino]-2-hydroxy-
1-(phenylmethyl)propyl]-, [1S-[1R*(2S*, 3R*),
2S*]], and [1S-[1R*(2R*.3S*), 2S*]].

Part A

To a solution of 863 mg (5.91 mmol) of meso-2,3-dimethylsuccinic acid in 7 mL of DMF at RT was added 1.13 g (5.91 mmol) of EDC. After 15 minutes, a solution of 2.07 g (5.91 mmol) of the product from Example 34, Part E and 1.4 mL of pyridine in 7 mL of anhydrous methylene chloride was added. After 11 hours, ethyl acetate was added and washed with 0.2N HCl, brine, dried and concentrated to afford 2.73 g (97%) of a 1:1 mixture of diastereomeric acids.

Part B

To a solution of 1.45 g (3.04 mmol) of the 1:1 mixture from Part A and 613 mg (4.51 mmol) of HOBT in 10 mL of DMF at 0° C. was added 635 mg (3.31 mmol) of EDC. After 30 minutes at 0° C., 5 mL of conc. aqueous ammonia was added. After 1 hour at 0° C. and 14 hours at RT, ethyl acetate was added, washed with 0.2N HCl, sat'd NaHCO$_3$, brine, dried and concentrated to afford 0.64 g (44%) of a 1:1 mixture of amides.

These were separated on a Whatman 10 micron partisil column using 8%–14% isopropanol/-methylene chloride. The first isomer to elute was identified as butanediamide, N-[3-[[[(1,1-dimethylethyl)amino] carbonyl](3-methylbutyl)amino]-2-hydroxy- 1-(phenylmethyl)propyl]-, [1S-[1R*(2R*, 3S*), 2S*], m/e/=477 (M+H).

The second isomer to elute was identified as butanediamide, N-[3-[[[(1,1-dimethylethyl)amino]carbonyl] (3-methylbutyl)amino]-2-hydroxy-1-(phenylmethyl)propyl]-, [1S-[1R*(2S*, 3R*), 2S*], m/e=477 (M+H).

EXAMPLE 43

Preparation of pentanediamide,
N-[3-[[[(1,1-dimethylethyl)amino]
carbonyl](3-methylbutyl)amino]-2-hydroxy-
1-(phenylmethyl)propyl-3.3-dimethyl-, [1S-[1R*,
2S*], Part A To a solution of 232 mg (0.66 mmol) of the product from Exactable 34, Part E and 98 mg (1.2 mmol) of pyridine in 2 mL of methylene chloride was added 95 mg (0.66 mmol) of 3,3-dimethylglutaric anhydride at RT. After 15 hours, ethyl acetate was added, washed with 1N HCl, brine, dried and concentrated to afford 261 mg of crude product. Chromatography on silica gel using 5–20% methanol/methylene chloride afforded 108 mg of acid, m/e= 492 (M+H).

Part B

To a solution of 92 mg (0.19 mmol) of product from Part A and 38 mg (0.28 mmol) HOBT in 0.5 mL DMF at 0° C. was added 36 mg (0.19 mmol) of EDC. After 30 minutes at 0° C., 0.25 mL of conc. aqueous ammonia was added. After 1 hour at 0° C. and 16 hours at RT, ethyl acetate was added, washed with 0.2N HCl, sat'd NaHCO$_3$, brine, dried and concentrated to afford 72 mg of crude product. This was passed through a one-inch column of basic alumina with 10% methanol/methylene chloride to afford 53 mg of desired product, m/e=491 (M+H).

EXAMPLE 44

Preparation of butanediamide,
N-[3-[[[(1,1-dimethylethyl)amino]
carbonyl](3-methylbutyl)amino]-2-hydroxy-
1-(phenylmethyl)propyl]-2,3-dimethyl
-[1S-[1R*(2R*, 3S*), 2S*]](Isomer #1) and Preparation of butanediamide,
N-[3-[[[(1,1-dimethylethyl)amino]
carbonyl](3-methylbutyl)amino]-2-hydroxy-
1-(phenylmethyl)propyl]-2,3-dimethyl-[1S-[1R*(2R*,
3S*), 2S*]](Isomer #2), Part A To a solution of 1.47 g (4.20 mmol) of the product from Example 34, Part E and 1.4 mL of pyridine in 9 mL of methylene chloride at RT was added 538 mg (4.20 mmol) of 2,2-dimethylsuccinic anhydride. After 15 hours, ethyl acetate was added and washed with 0.2N HCl, brine, dried and concentrated to afford 1.87 g of crude product (approx. 3:1 mixture of isomers).

Part B

To a solution of 1.85 g (3.9 mmol) of crude product from Part A and 887 mg (5.8 mmol) of HOBT in 10 mL of DMF at 0° C. was added 809 mg (4.2 mmol) EDC. After 30 minutes at 0° C., 6 mL of conc. aqueous ammonia was added. After 1 hour at 0° C. and 15 hours at RT, ethyl acetate was added, washed with 0.2N HCl, sat'd NaHCO$_3$, brine, dried and concentrated to afford 923 mg of crude product. The two isomers were separated on a Whatman Partisil 5 column using 8–14% isopropanol/methylene chloride. The major isomer was identified as Isomer #1, m/e=477 (M+H).

The minor isomer was identified as Isomer #2, m/e=477 (M+H).

EXAMPLE 45

This example illustrates the procedure utilized to prepare compounds wherein the stereochemistry about the hydroxyl group is (S).

Part A

A solution of 3 (S)-(1,1-dimethylethoxycarbonyl)-amino-1,2-(R)-epoxy-4-phenylbutane (1.00 g, 3.80 mmol) and isobutylamine (5.55 g, 76 mmol, 20 equiv.) in 10 mL of isopropyl alcohol was warmed to 60° C. for 1 hour. The solution was cooled to room temperature and concentrated in vacuo and the residue recrystallized from hexane/methylene chloride to give 0.93 g, 73% of [2(S), 3(S)]-N-[[[3-[(1,1-dimethylethyl)carbamoyl] amino]]-2-hydroxy-4-phenylbutyl]N-[ (3-methylbutyl)]amine, mp 91.3°–93.0° C.

Part B

The product from Part A (46.3mg, 0.14 mmol) was dissolved in a mixture of 5 mL of tetrahydrofuran and 2 mL of methylene chloride and treated with tert-butylisocyanate (136.4mg, 1.376 mmol) via syringe. The solution was stirred at room temperature for 0.5 hour and then the solvent was removed in vacuo. The product, TLC on SiO$_2$, 1:1 hexane: ethyl acetate had Rf=0.74 and was used directly in the next step without further purification.

Part C

The crude product from Part B was taken up in 10 mL of 4N hydrochloric acid in dioxane and stirred at room temperature for 0.25 hours. The solvent and excess hydrochloric acid was removed in vacuo whereupon the product crystallized. The solid was isolated by filtration washed with acetone and dried in vacuo to 3-[[(1,1-dimethylethyl)amino] carbonyl](2-methylpropyl)amino-2(S)-hydroxy- 1(S)-(phenylmethyl)propylamine hydrochloride.

Part D

A solution of N-Cbz-L-asparagine (225.5mg, 0.847 mmol) and [-hydroxybenzotriazole (182.9mg, 1.21 mmol) was dissolved in 2 mL of dimethylformamide and cooled to 0° C. and then treated with EDC (170.2mg, 0.898 mmol) for 10 minutes. This mixture was then treated with 3-[[(1,1-dimethylethyl)amino] carbonyl](2-methylpropyl)amino-2(S)-hydroxy- 1(S)-(phenylmethyl)propylamine hydrochloride. (300.0mg, 0.807 mmol) followed by N-methylmorpholine (90.0mg, 0.888 mmol) via syringe. The solution was stirred at room temperature for 16 hours and then poured into 20 mL of rapidly stirring 60% saturated aqueous sodium bicarbonate solution whereupon a white precipitate formed. The solid was isolated by filtration, washed with saturated aqueous sodium bicarbonate solution, water, 5% aqueous citric acid solution, water and then dried in vacuo to give 319mg, 68% of butanediamide, N$^1$-[3-[[ [(1,1-dimethylethyl)amino] carboyl](2-methylpropyl)amino]-2(S)-hydroxy- 1(S)-(phenylmethyl)propyl]-2(S) [ (benzyloxycarbonyl)amino]mp 139°–141° C., MH+m/z= 584.

EXAMPLE 46

The compounds of the present invention are effective HIV protease inhibitors. Utilizing an enzyme assay as described below, the compounds set forth in the examples herein disclosed inhibited the HIV enzyme. The preferred compounds of the present invention and their calculated IC$_{50}$ (inhibiting concentration 50%, i.e., the concentration at which the inhibitor compound reduces enzyme activity by 50%) values are shown in Table 16. The enzyme method is described below. The substrate is 2-aminobenzoyl-Ile-Nle-Phe(p-NO$_2$)-Gln-ArgNH$_2$. The positive control is MVT-101 (Miller, M. et al, Science, 246, 1149 (1989)]The assay conditions are as follows:

Assay buffer: 20 mM sodium phosphate, pH 6.4
 20% glycerol
 1 mMEDTA
 1 mMDTT
 0.1% CHAPS The above described substrate is dissolved in DMSO, then diluted 10 fold in assay buffer. Final substrate concentration in the assay is 80 μM.

HIV protease is diluted in the assay buffer to a final enzyme concentration of 12.3 nanomolar, based on a molecular weight of 10,780.

The final concentration of DMSO is 14% and the final concentration of glycerol is 18%. The test compound is dissolved in DMSO and diluted in DMSO to 10x the test concentration; 10 μl of the enzyme preparation is added, the materials mixed and then the mixture is incubated at ambient temperature for 15 minutes. The enzyme reaction is initiated by the addition of 40 μl of substrate. The increase in fluorescence is monitored at 4 time points (0, 8, 16 and 24 minutes) at ambient temperature. Each assay is carried out in duplicate wells.

TABLE 16

| Compound | IC$_{50}$ (nanomolar) |
|---|---|
| 1a) Butanediamide, N$^1$-[3-[[[(1,1-dimethylethyl)amino]carbonyl] (2-methylpropyl)amino]-2-hydroxy-1-(phenylmethyl)propyl]-2-[(N-benzyloxycarbonyl)amino]-, [1S-[1R*(R*), 2S*]]- | 35 |
| 1b) Butanediamide, N$^1$-[3-[[[(1,1-dimethylethyl)amino]carbonyl] (2-methylpropyl)amino]-2-hydroxy-1-(phenylmethyl)propyl]-2-[(2-quinolinylcarbonyl)amino]-, [1S-[1R*(R*),2S*]]- | 7.1 |
| 2a) Butanediamide, N$^1$-[3-[[[(1,1-dimethylethyl)amino]carbonyl](3- | 13.4 |

TABLE 16-continued

| Compound | IC$_{50}$ (nanomolar) |
|---|---|
| methylbutyl)amino]-2-hydroxy-1-(phenylmethyl)propyl]-2-[(N-benzyloxycarbonyl)amino], [1S-[1R*(R*),2S*]]- | |
| 2b) Butanediamide, N$^1$-[3-[[[(1,1-dimethylethyl)amino]carbonyl](3-methylbutyl)amino]-2-hydroxy-1-(phenylmethyl)propyl]-2-[(2-quinolinylcarbonyl)amino]-, [1S-[1R*(R*),2S*]]- | 3.2 |
| 3a) Butanediamide, N$^1$-[3-[[[(1,1-dimethylethyl)amino]carbonyl](2-naphthylmethyl)amino]-2-hydroxy-1-(phenylmethyl)propyl]-2-[(N-benzyl-oxycarbonyl)amino]-, [1S-[1R*(R*),2S*]]- | 31.0 |
| 3b) Butanediamide, N$^1$-[3-[[[(1,1-dimethylethyl)amino]carbonyl](2-naphthylmethyl)amino]-2-hydroxy-1-(phenylmethyl)propyl]-2-[(2-quinolinylcarbonyl)amino]-, [1S-[1R*(R*),2S*]]- | 2.9 |
| 4a) Butanediamide, N$^1$-[3-(([(1,1-dimethylethyl)amino]carbonyl](2-phenylethyl)amino]-2-hydroxy-1-(phenylmethyl)propyl]-2-[(N-benzyloxycarbonyl)amino]-, [1S-[1R*(R*),2S*]]- | 70 |
| 4b) Butanedianxide, N$^1$-[3-[[[(1,1-dimethylethyl)amino]carbonyl](2-phenylethyl)amino]-2-hydroxy-1-(phenylmethyl)propyl]-2-[(2-quinolinylcarbonyl)amino]-, [1S-[1R*(R*),2S*]]- | 10 |
| 5a) Butanediamide, N$^1$-[3-[[[(1,1-dimethylethyl)amino]carbonyl](3,3-dimethylpropyl)amino]-2-hydroxy-1-(phenylmethyl)propyl]-2-[(N-benzyloxycarbonyl)amino], [1S-[1R*(R*),2S*]]- | 18 |
| 5b) Butanediamide, N$^1$-[3-[[[(1,1-dimethylethyl)amino]carbonyl](3,3-dimethylpropyl)amino]-2-hydroxy-1-(phenylmethyl)propyl]-2-((2-quinolinylcarbonyl)amino]-, [1S-[1R*(R*),2S*]]- | 3.7 |
| 6) Propanamide, N-[3-[[[(1,1-dimethylethyl)amino]carbonyl](3-methylbutyl)amino]-2-hydroxy-1-(phenylmethyl)propyl]-2-methyl-3-(methylsulfonyl)-, [1S-[1R*(R*),2S*]]- | 29 |
| 7) Propanamide, 3-(acetylamino)-N-[3-[[[(11,-dimethylethyl)amino]carbonyl](3-methylbutyl)amino]-2-hydroxy-1-(phenylmethyl)propyl]-2-methyl-, [1S-[1R*(S*),2S*]]- | 100 |
| 8) Propanamide, 3-(4-methoxybenzyloxy-carbonyl)amino-N-(3-[[[(11,-dimethylethyl)amino]carbonyl](3-methylbutyl)aminol-2-hydroxy-1-(phenylmethyl)propyl]-2-methyl-, [1S-[1R*(S*),2S*]]- | 6 |
| 9) Butanediamide, N$^1$-(2-hydroxy-3-[(4-fluorophenylmethyl)(1-pyrrolidinyl-carbonyl)amino]-1-(phenylmethyl) propyl]-2-[(2-quinolinylcarbonyl)amino]-, [1S-[1R*(R*),2S*]]- | 7 |
| 10) Butanediamide, N$^1$-[3-[[[(1,1-dimethylethyl)amino]carbonyl](3-methylbutyl)amino]-2-hydroxy-1-(phenylmethyl)propyl]-2,3,3-trimethyl-, [1S-[1R*(2S*),2S*]]- | 12 |
| 11) Butanoic acid, 4-[[3-[[[(1,1-dimethylethyl)amino]carbonyl](3-methylbutyl)amino]-2-hydroxy-1-(phenylmethyl)propyl]amino-2,2,3-trimethyl-4-oxo-, [1S-[1R*(3S*),2S*]]- | 8 |
| 12) Butaneamide,2-(acetylamino)-N-[3-[[[(1,1-dimethylethyl)amino]-carbonyl](3-methylbutyl)amino]-2-hydroxy-1-(phenylmethyl)propyl]-3,3-dimethyl-, [1S-[1R*(R*),2S*]]- | 18 |
| 13) Butaneamide, 2-[92,2-dimethylaminoacetyl)amino]-N-[3-[[[(1,1-dimethylethyl)amino]carbonyl](3-methylbutyl)amino]-2-hydroxy-1-(phenylmethyl)propyl]-3,3dimethyl-, [1S-[1R*(R*),2S*]]- | 10 |

EXAMPLE 47

The effectiveness of the compounds listed in Table 9 were determined in the above-described enzyme assay and in a CEM cell assay.

The HIV inhibition assay method of acutely infected cells is an automated tetrazolium based colorimetric assay essentially that reported by Pauwles et al, *J, Virol. Methods* 20, 309–321 (1988). Assays were performed in 96-well tissue culture plates. CEM cells, a CD4$^+$cell line, were grown in RPMI-1640 medium (Gibco) supplemented with a 10% fetal calf serum and were then treated with polybrene (2 μg/ml). An 80 μl volume of medium containing 1×10$^4$ cells was dispensed into each well of the tissue culture plate. To each well was added a 100 μl volume of test compound dissolved in tissue culture medium (or medium without test compound as a control) to achieve the desired final concentration and the cells were incubated at 37° C. for 1 hour. A frozen culture of HIV-1 was diluted in culture medium to a concentration of 5×10$^4$ TCID$_{50}$ per ml (TCID$_{50}$ =the dose of virus that infects 50% of cells in tissue culture), and a 20 μL volume of the virus sample (containing 1000 TCID$_{50}$ of virus) was added to wells containing test compound and to wells containing only medium (infected control cells). Several wells received culture medium without virus (uninfected control cells). Likewise, the intrinsic toxicity of the test compound was determined by adding medium without virus to several wells containing test compound. In summary, the tissue culture plates contained the following experiments:

|   | Cells | Drug | Virus |
|---|---|---|---|
| 1. | + | − | − |
| 2. | + | + | − |
| 3. | + | − | + |
| 4. | + | + | + |

In experiments 2 and 4 the final concentrations of test compounds were 1, 10, 100 and 500 µg/ml. Either azidothymidine (AZT) or dideoxyinosine (ddI) was included as a positive drug control. Test compounds were dissolved in DMSO and diluted into tissue culture medium so that the final DMSO concentration did not exceed 1.5% in any case. DMSO was added to all control wells at an appropriate concentration.

Following the addition of virus, cells were incubated at 37° C. in a humidified, 5% $CO_2$ atmosphere for 7 days. Test compounds could be added on days 0, 2 and 5 if desired. On day 7, post-infection, the cells in each well were resuspended and a 100 µl sample of each cell suspension was removed for assay. A 20 µL volume of a 5 mg/ml solution of 3-(4,5-dimethylthiazol-2-yl)-2,5-diphenyltetrazoliumbromide (MTT) was added to each 100 µL cell suspension, and the cells were incubated for 4 hours at 27° C. in a 5% $CO_2$ environment. During this incubation, MTT is metabolically reduced by living cells resulting in the production in the cell of a colored formazan product. To each sample was added 100 µl of 10% sodium dodecylsulfate in 0.01 N HCl to lyse the cells, and samples were incubated overnight. The absorbance at 590 nm was determined for each sample using a Molecular Devices microplate reader. Absorbance values for each set of wells is compared to assess viral control infection, uninfected control cell response as well as test compound by cytotoxicity and antiviral efficacy.

TABLE 17

| Compound | $IC_{50}$ | $EC_{50}$ | $TD_{50}$ |
|---|---|---|---|
| butanediamide $N^1$[3-[[[n-butylamino]carbonyl](2-methylpropyl)amino]-2-hydroxy-1-(phenylmethyl)propyl]-2-[(phenylmethylcarbamoyl)amino], [1S-[1R*(R*), 2S*]]--. | 940 nM | 17 µM | 170–180 µM |
| butanediamide $N^1$[3-[[[n-butylamino]carbonyl](2-methylpropyl)amino]-2-hydroxy-1-(phenylmethyl)propyl]-2-[(2-quinolinylcarbonyl)amino]-[1S-[1R*(R*), 2S*]]-. | 126 nM | 26 nM | 53 µM |
| butanediamide $N^1$[3-[[[(1,1-dimethylethyl)amino]-carbonyl](2-phenylethyl)amino]-2-hydroxy-1-(phenylmethyl)propyl]-2-[(2-quinolinylcarbonyl)amino] [1S-[1R*(R*), 2S*]]-. | 10 nM | 28 nM | 13 µM |
| butanediamide $N^1$[3-[[[(1,1-dimethylethyl)amino]-carbonyl](2-methylpropyl)amino-2-hydroxy-1-(phenylmethyl)propyl]-2-[(2-quinolinylcarbonyl)amino] [1S-[1R*(R*), 2S*]]-. | 7 nM | 10 nM | 6 µM |
| butaneamide, 2-[92,2-dimethylaminoacetyl)amino]-N-[3-[[[(1,1-dimethylethyl)amino]carbonyl](3-methylbutyl)amino]-2-hydroxy-1-(phenylmethyl)propyl]-3,3-dimethyl-, [1S-[IR*(R*),2S*]]-. | 10 nM | 58 nM | tba |

Utilizing the procedures set forth above in the examples along with the general description, it is contemplated that the compounds listed below and those shown in Tables 18 and 19 could be prepared and that such compounds would have activities as HIV protease inhibitors substantially similar to the activities of the compounds set forth in the examples.

Butanediamide, $N^1$-[3-[[[(1,1-dimethylethyl)amino] carbonyl]pentylamino]-2- hydroxy-1-(phenylmethyl) propyl]-2-[(2-quinolinylcarbonyl)amino]-, [1S-[1R*(R*),2S*]]

Butanediamide, $N^1$-[3-[[[(1,1-dimethylethyl)amino] carbonyl]hexyl amino]-2-hydroxy-1-(phenylmethyl) propyl]-2-[(2-quinolinylcarbonyl)amino]-, [1S-[1R*(R*),2S*]]

Propanamide, N-[3-[[[(1,1-dimethylethyl)amino] carbonyl]butylamino]-2-hydroxy-1-(phenylmethyl)propyl]- 2-methyl-3-(methylsulfonyl)-, [1S-[ 1R*(R*),2S*]]-

Propanamide, N-[3-[[[(1,1-dimethylethyl)amino] carbonyl](phenylmethyl)amino]-2-hydroxy- 1-(phenylmethyl)propyl]-2-methyl-3-(methylsulfonyl)-, [1S-[1R*(R*),2S*]]-

Propanamide, N-[3-[[[(1, 1-dimethylethyl)amino]carbonyl] (4-fluorophenylmethyl)amino]- 2-hydroxy-1-(phenylmethyl)propyl]- 2-methyl-3-(methylsulfonyl)-, [1S-[ 1R*(R*),2S*]]-

Propanamide, N-[3-[[[(1, 1-dimethylethyl)amino]carbonyl] (4-methoxyphenylmethyl)amino]- 2-hydroxy-1-(phenylmethyl)propyl]- 2-methyl-3-(methylsulfonyl)-, [1S-[ 1R*(R*),2S*]]-

Propanamide, N-[3-[[[(1,1-dimethylethyl)amino] carbonyl](cyclohexylmethyl)amino]-2-hydroxy- 1-(phenylmethyl)propyl]-2-methyl-3-(methylsulfonyl)-, [1S-[1R*(R*), 2S*]]-

Propanamide, N-[3-[[[(1,1-dimethylethyl)amino] carbonyl](3-methylbutyl)amino]- 2-hydroxy-1-(cyclohexylmethyl)propyl]-2-methyl- 3-(methylsulfonyl)-, [1S-[1R*(R*, 2S*]]-

Butanediamide, $N^1$-[2-hydroxy-3-[(3-methylbutyl) (1-pyrrolidinylcarbonyl)amino]- 1-(phenylmethyl)propyl]-2-[(2-quinolinylcarbonyl) amino]-, [1S-[1R*(R*),2S*]]-

Butanediamide, $N^1$-[2-hydroxy-3-[( 3-methylbutyl) (1-pyrrolidinylcarbonyl)amino]- 1-(4-fluorophenylmethyl)propyl]- 2-[(2-quinolinylcarbonyl)amino]-, [1S-[ 1R*(R*), 2S*-]]-

Butanediamide, $N^1$-[2-hydroxy-3-[ (3-methylbutyl)(1-pyrrolidinylcarbonyl)amino]- 1-(cyclohexylmethyl)propyl]-2-[ (2-quinolinylcarbonyl)amino]-, [1S-[1R*(R*),2S*]]-

Butanediamide, $N^1$-[2-hydroxy-3-[ (phenylmethyl)(4-morpholinylcarbonyl)amino]- 1-(phenylmethyl)propyl]-2-[(2-quinolinylcarbonyl)amino]-, [1S-[1R*(R*),2S*]]-

Butanediamide, $N^1$-[2-hydroxy-3-[ (3-methylbutyl)(1-piperidinylcarbonyl)amino]- 1-(phenylmethyl)propyl]-2-[(2-quinolinylcarbonyl)amino]-, [1S-[1R*(R*),2S*]]-

Butanediamide, $N^1$-[2-hydroxy-3-[ (phenylmethyl)(1-piperidinylcarbonyl)amino]- 1-(phenylmethyl)propyl]-2-[(2-quinolinylcarbonyl)amino]-, [1S-[1R*(R*),2S*]]-

Butanediamide, N-[3-[[[(1,1-dimethylethyl)amino] carbonyl]butylamino]-2-hydroxy-1-(phenylmethyl) propyl]-2, 3,3-trimethyl-, [1S-[ 1R*(2S*),2S*]]-

Butanediamide, N-[3-[[[(1,1-dimethylethyl)amino] carbonyl](phenylmethyl)amino]-2-hydroxy- 1-(phenylmethyl)propyl]-2,3,3-trimethyl-, [1S-[ 1R*(2S*),2S*]]-

Butanediamide, N-[3-[[[(1, 1-dimethylethyl)amino] carbonyl](4-fluorophenylmethyl)amino]- 2-hydroxy-1-(phenylmethyl)propyl]-2,3,3-trimethyl-, [1S-[ 1R*(2S*),2S*]]-

Butanediamide, N-[3-[[[(1,1-dimethylethyl)amino] carbonyl](cyclohexylmethyl)amino]-2-hydroxy- 1-(phenylmethyl)propyl]-2,3,3-trimethyl-, [1S-[ 1R*(2S*),2S*]]-

Butanediamide, N-[3-[[[(1,1-dimethylethyl)amino] carbonyl](3-methylbutyl)amino]-2-hydroxy- 1-(cyclohexylmethyl)propyl]-2,3,3-trimethyl-, [1S-[ 1R*(2S*),2S*]]-

Butanoic acid, 4-[[3-[[[(1,1-dimethylethyl)amino] carbonyl] butylamino]-2-hydroxy-1-(phenylmethyl) propyl]amino-2,2,3-trimethyl-4-oxo-, [1S-[ 1R*(3S*),2S*]]-

Butanoic acid, 4-[[3-[[[(1,1-dimethylethyl)amino] carbonyl] (phenylmethyl)amino]-2-hydroxy- 1-(phenylmethyl)propyl]amino-2,2,3-trimethyl-4-oxo-, [1S-[1R*(3S*),2S*]]-

Butanoic acid, 4-[[3-[[[(1,1-dimethylethyl)amino] carbonyl] (4-fluorophenylmethyl)amino]- 2-hydroxy-1-(phenylmethyl)propyl]amino-2,2,3-trimethyl-4-oxo-, [1S-[1R*(3S*),2S*]]-

Butanoic acid, 4-[[3-[[[(1,1-dimethylethyl)amino] carbonyl] (cyclohexylmethyl)amino]-2-hydroxy- 1-(phenylmethyl)propyl]amino-2,2,3-trimethyl-4-oxo-, [1S-[1R*(3S*),2S*]]-

Butaneamide, 2-(acetylamino)-N-[3-[[[(1,1-dimethylethyl)amino] carbonyl](3-methylbutyl)amino]-2-hydroxy-1-(cyclohexylmethyl)propyl]-3,3-dimethyl-, [1S-[1R*(R*),2S*]]-

Butaneamide, 2-(acetylamino)-N-[3-[[[(1,1-dimethylethyl)amino] carbonyl]butylamino]-2-hydroxy-1-(phenylmethyl)propyl]- 3,3-dimethyl-, [1S-[1R*(R*),2S*]]-

Butaneamide, 2-(acetylamino)-N-[3-[[[(1,1-dimethylethyl)amino] carbonyl](phenylmethyl)amino]-2-hydroxy-1-(phenylmethyl)propyl]-3,3-dimethyl-, [1S-[ 1R*(R*),2S*]]-

Butaneamide, 2-(acetylamino)-N-[3-[[[(1,1-dimethylethyl)amino] carbonyl](cyclohexylmethyl)amino]-2-hydroxy-1-(phenylmethyl)propyl]-3,3-dimethyl-, [1S-[ 1R*(R*),2S*]]

Butaneamide, 2-[(2,2-dimethylaminoacetyl)amino]-N-[3-[[ [(1,1-dimethylethyl) amino]carbonyl](3-methylbutyl)amino]-2-hydroxy- 1-(phenylmethyl)propyl]-3-methyl-, [1S-[ 1R*(R*),2S*]]

Butaneamide, 2-[(2,2-dimethylaminoacetyl)amino]-N-[3-[[ [(1,1-dimethylethyl)amino] carbonyl](3-methylbutyl)amino]-2-hydroxy- 1-(cyclohexylmethyl)propyl]-3,3-dimethyl-, [1S-[ 1R*(R*),2S*]]

Butaneamide, 2-[(2,2-dimethylaminoacetyl)amino]-N-[3-[[ [(1,1-dimethylethyl)amino] carbonyl]butylamino]-2-hydroxy-1-(phenylmethyl)propyl]- 3,3-dimethyl-, [1S-[1R*(R*),2S*]]

Butaneamide, 2-[(2,2-dimethylaminoacetyl)amino]-N-[3-[[ [(1,1-dimethylethyl)amino] carbonyl](phenylmethyl)amino]-2-hydroxy- 1-(phenylmethyl)propyl]-3,3-dimethyl-, [1S-[ 1R*(R*),2S*]]

Butaneamide, 2-[(2,2-dimethylaminoacetyl)amino]-N-[3-[[ [(1,1-dimethylethyl)amino] carbonyl](4-fluorophenylmethyl)amino]- 2-hydroxy-1-(phenylmethyl)propyl]-3,3-dimethyl-, [1S-[ 1R*(R*),2S*]]-

Butaneamide, 2-[(2,2-dimethylaminoacetyl)amino]-N-[3-[[ [(1,1-dimethylethyl)amino] carbonyl](cyclohexylmethyl)amino]-2-hydroxy- 1-(phenylmethyl)propyl]-3,3-dimethyl-, [1S-[1R*(R*),2S*]]-

TABLE 18

| $R^1$ | $R^2$ | $R^3$ |
| --- | --- | --- |
| t-Butyl | Benzyl | p-Fluorobenzyl |
| i-Butyl | Benzyl | i-Amyl |
| i-Propyl | Benzyl | i-Amyl |
| Propargyl | Benzyl | i-Amyl |

TABLE 18-continued

| $R^1$ | $R^2$ | $R^3$ |
| --- | --- | --- |
| t-Butyl | Benzyl | i-Amyl |
| t-Butyl | Benzyl | Benzyl |
| t-Butyl | Benzyl | n-Butyl |
| sec-Butyl | Benzyl | i-Amyl |
| $C(CH_3)_2(SCH_3)$ | Benzyl | i-Amyl |
| t-Butyl | p-Fluorobenzyl | p-Methoxybenzyl |
| i-Butyl | p-Fluorobenzyl | i-Amyl |
| i-Propyl | p-Fluorobenzyl | i-Amyl |
| Propargyl | p-Fluorobenzyl | i-Amyl |
| t-Butyl | p-Fluorobenzyl | i-Amyl |
| t-Butyl | p-Fluorobenzyl | Benzyl |
| t-Butyl | p-Fluorobenzyl | n-Butyl |
| sec-Butyl | Benzyl | i-Amyl |
| $C(CH_3)_2(SCH_3)$ | Benzyl | i-Amyl |
| t-Butyl | Cyclohexylmethyl | p-Fluorobenzyl |
| i-Butyl | Cyclohexylmethyl | i-Amyl |
| i-Propyl | Cyclohexylmethyl | i-Amyl |
| Propargyl | Cyclohexylmethyl | i-Amyl |
| t-Butyl | Cyclohexylmethyl | i-Amyl |
| t-Butyl | Cyclohexylmethyl | Benzyl |
| t-Butyl | Cyclohexylmethyl | n-Butyl |
| sec-Butyl | Cyclohexylmethyl | i-Amyl |
| $C(CH_3)_2(SCH_3)$ | Cyclohexylmethyl | i-Amyl |
| t-Butyl | n-Butyl | Cyclohexylmethyl |
| i-Butyl | n-Butyl | i-Amyl |
| i-Propyl | n-Butyl | i-Amyl |
| Propargyl | n-Butyl | i-Amyl |
| t-Butyl | n-Butyl | i-Amyl |
| t-Butyl | n-Butyl | Benzyl |
| t-Butyl | n-Butyl | n-Butyl |
| sec-Butyl | n-Butyl | i-Amyl |
| $C(CH_3)_2(SCH_3)$ | n-Butyl | i-Amyl |

TABLE 19

| $R^1$ | $R^2$ | $R^3$ |
| --- | --- | --- |
| methyl | methyl | methyl |
| benzyl | methyl | methyl |
| hydroxymethyl | methyl | methyl |
| 1-hydroxyethyl | methyl | methyl |
| hydrogen | methyl | ethyl |
| hydrogen | methyl | benzyl |
| hydrogen | $R^2 + R^3$ = imidazole | |

The compounds of the present invention are effective antiviral compounds and, in particular, are effective inhibitors of retroviruses, particularly, lentroviruses as shown above. Thus, the subject compounds are effective inhibitors of HIV. It is contemplated that the subject compounds will also inhibit other strains of HIV, such as HIV-2 and other viruses such as, for example, human T-cell leukemia virus, feline leukemia virus, simiam immunodeficiency virus, respiratory syncitial virus, hepadnavirus, cytomegalovirus and picornavirus. Thus, the subject compounds are effective in the treatment and/or proplylaxis of retroviral infections.

Compounds of the present can possess one or more asymmetric carbon atoms and are thus capable of existing in the form of optical isomers as well as in the form of racemic or nonracemic mixtures thereof. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of Formula I with an optically pure acid in an activated form or an optically pure isocyanate. The synthesized diastereoisomers can be separated by conventional means such as chromatography, distillation, crystallization or sublimation, and then hydrolyzed to deliver the enantiomericaly pure compound. The optically active compounds of Formula I can likewise be obtained by utilizing optically active starting materials. These isomers may be in the form of a free acid, a free base, an ester or a salt.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate. Also, the basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Total daily dose administered to a host in single or divided doses may be in amounts, for example, from 0.001 to 10 mg/kg body weight daily and more usually 0.01 to 1 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

The dosage regimen for treating a disease condition with the compounds and/or compositions of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed may vary widely and therefore may deviate from the preferred dosage regimen set forth above.

The compounds of the present invention may be administered orally, parenterally, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

While the compounds of the invention can be administered as the sole active pharmaceutical agent, they can also be used in combination with one or more immunomodulators, antiviral agents or other antiinfective agents. For example, the compounds of the invention can be administered in combination with AZT or with N-butyl-1-deoxynojirimycin for the prophylasis and/or treatment of AIDS. When administered as a combination, the therapeutic agents can be formulated as separate compositions which are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Method of inhibiting a retroviral protease comprising administering an effective amount of a compound represented by the formula

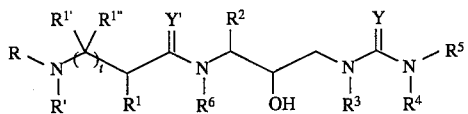

or a pharmaceutically acceptable salt, prodrug or ester thereof wherein t represents O or 1;

Y and Y' each independently represent O or S;

R represents hydrogen, alkoxycarbonyl, aralkoxycarbonyl, alkanoyl, aroyl, aryloxyalkanoyl, heterocyclylcarbonyl, heterocyclylalkanoyl, heteroaroyl, heteroaralkanoyl, alkyl, aralkyl, 3-carboxypropionyl, methyloxaloyl, bromoacetyl, trifluoroacetyl, methoxyacetyl, hydroxyacetyl, hydroxypropionyl, aminocarbonyl, N-alkylaminocarbonyl, N- mono- or N,N-disubstituted aminoalkanoyl radicals wherein said substituents are alkyl, aryl, aralkyl, cycloalkyl, heteroaralkyl, heterocycloalkyl, hydroxyethyl or methoxyethyl radicals, or in the case of a disubstituted aminoalkanoyl radical, said substituents along with the nitrogen atom to which they are attached form heterocyclyl or heteroaryl radicals, with the proviso that said heteroaryl radical is other than a quaternary nitrogen containing heteroaryl radical;

R' represents hydrogen, alkyl or aralkyl radicals; or R and R' together with the nitrogen to which they are attached form heterocycloalkyl or heteroaryl radicals, with the proviso that said heteroaryl radical is other than a quaternary nitrogen containing heteroaryl radical;

$R^1$ represents hydrogen, $-CF_3$, $-CH(CF_3)_2$, $-CH_2SO_2NH_2$, $-CO_2CH_3$, $-CONHCH_3$, $-CON(CH_3)_2$, $-CH_2C(O)NHCH_3$, $-CH_2C(O)N(CH_3)_2$, $-CONH_2$, $-C(CH_3)_2(SCH_3)$, $-C(CH_3)_2(S(O)CH_3)$, $-C(CH_3)_2(S(O)_2CH_3)$, alkyl, haloalkyl, alkenyl or alkynyl radicals, or the side chain of the amino acid asparagine, S-methyl cysteine or the corresponding sulfoxide or sulfone derivatives thereof, leucine, isoleucine, allo-isoleucine, tert-leucine, phenylalanine, ornithine, alanine, histidine, norleucine, glutamine, valine, threonine, serine, aspartic acid, beta-cyano alanine or allothreonine;

$R^{1'}$ represents hydrogen or alkyl radicals;

$R^{1''}$ represents hydrogen, $-CO_2CH_3$, $-CONH_2$ or alkyl radicals; or $R^{1''}$ together with $R^1$ and the carbon atoms to which they are attached represent a cycloalkyl radical;

$R^2$ represents alkyl, cycloalkylalkyl or aralkyl radicals, each of which is optionally substituted with $-OR^9$, $-SR^9$ or halogen radicals, wherein $R^9$ represents hydrogen or alkyl radicals;

$R^3$ represents alkyl, alkenyl, hydroxyalkyl, alkoxyalkyl, cycloalkyl, cycloalkylalkyl, heterocycloalkylalkyl, aryl, aralkyl or heteroaralkyl radicals;

$R^4$ represents alkyl, alkenyl, alkynyl, hydroxyalkyl, alkoxyalkyl, cycloalkyl, cycloalkylalkyl, heterocycloalkylalkyl, aryl or aralkyl radicals;

$R^5$ represents hydrogen or alkyl radicals; or $R^4$ and $R^5$ together with the nitrogen atom to which they are bonded represent a heterocycloalkyl radical; and $R^6$ represents hydrogen or alkyl radicals; and wherein alkyl, alone or in combination, means a straight-chain or branched-chain alkyl radical containing from 1 to 8 carbon atoms; alkenyl, alone or in combination, means a straight-chain or branched-chain hydrocarbon radial having one or more double bonds and containing from 2 to 8 carbon atoms; alkynyl, alone or in combination, means a straight-chain hydrocarbon radical having one or more triple bonds and containing from 2 to 10 carbon atoms; cycloalkyl, alone or in combination, means a cyclic alkyl radical which contains from 3 to 8 carbon atoms; aryl, alone or in combination, means a phenyl or naphthyl radical which is optionally substituted with one or more alkyl, alkoxy, halogen, hydroxy, amino or nitro radicals; heterocyclyl or heterocycloalkyl, alone or in combination, means a saturated or partially unsaturated monocyclic, bicyclic or tricyclic heterocycle which contains one or more nitrogen, oxygen or sulfur heteroatoms, which is optionally substituted on one or more carbon atoms by halogen, alkyl, alkoxy or oxo, or on a secondary nitrogen atom by alkyl, aralkoxycarbonyl, alkanoyl, phenyl or phenylalkyl, or on a tertiary nitrogen atom by oxido; and heteroaryl, alone or in combination, means an aromatic heterocyclyl.

2. Method of claim 1 wherein said compound is represented by the formula

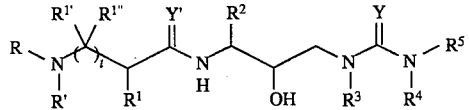

or a pharmaceutically acceptable salt, prodrug or ester thereof wherein t represents O or 1;

Y and Y' each independently represent O or S;

R represents hydrogen, alkoxycarbonyl, aralkoxycarbonyl, alkanoyl, aroyl, aryloxyalkanoyl, heterocyclylcarbonyl, heterocyclylalkanoyl, heteroaroyl, alkyl, aralkyl, 3-carboxypropionyl, methyloxaloyl, bromoacetyl, trifluoroacetyl, methoxyacetyl, hydroxyacetyl, hydroxypropionyl, aminocarbonyl, N-alkylaminocarbonyl, N- mono- or N,N-disubstituted aminoalkanoyl radicals wherein said substituents are alkyl, aryl, aralkyl, cycloalkyl, heteroaralkyl, heterocycloalkyl, hydroxyethyl or methoxyethyl radicals, or in the case of a disubstituted aminoalkanoyl radical, said substituents along with the nitrogen atom to which they are attached form a heterocyclyl radical;

R' represents hydrogen, alkyl or aralkyl radicals; or R and R' together with the nitrogen to which they are attached form a heteroaryl radical, with the proviso that said heteroaryl radical is other than a quaternary nitrogen containing heteroaryl radical;

$R^1$ represents hydrogen, $-CF_3$, $-CH(CF_3)_2$, $-CH_2SO_2NH_2$, $-CO_2CH_3$, $-CONHCH_3$, $-CON(CH_3)_2$, $-CH_2C(O)NHCH_3$, $-CH_2C(O)N(CH_3)_2$, $-CONH_2$, $-C(CH_3)_2(SCH_3)$, $-C(CH_3)_2(S(O)CH_3)$, $-C(CH_3)_2(S(O)_2CH_3)$, alkyl, haloalkyl, alkenyl or alkynyl radicals, or the side chain of the amino acid asparagine, S-methyl cysteine or the corresponding sulfoxide or sulfone derivatives thereof, leucine, isoleucine, allo-isoleucine, tert-leucine, phenylalanine, ornithine, alanine, histidine, norleucine, glutamine, valine, threonine, serine, aspartic acid, beta-cyano alanine or allothreonine;

$R^{1'}$ represents hydrogen or alkyl radicals;

$R^{1''}$ represents hydrogen, —$CO_2CH_3$, —$CONH_2$ or alkyl radicals;

or $R^{1'}$ together with $R^1$ and the carbon atoms to which they are attached represent a cycloalkyl radical;

$R^2$ represents alkyl, cycloalkylalkyl or aralkyl radicals, each of which is optionally substituted with —$OR^9$, —$SR^9$ or halogen radicals, wherein $R^9$ represents hydrogen or alkyl radicals;

$R^3$ represents alkyl, alkenyl, hydroxyalkyl, cycloalkyl, cycloalkylalkyl, heterocycloalkylalkyl, aryl, aralkyl or heteroaralkyl radicals;

$R^4$ represents alkyl or cycloalkyl radicals; and $R^5$ represents hydrogen or alkyl radicals; or $R^4$ and $R^5$ together with the nitrogen atom to which they are bonded represent a heterocycloalkyl radical.

3. Method of claim 2 wherein R represents hydrogen, alkoxycarbonyl, aralkoxycarbonyl, alkanoyl, aryloxyalkanoyl, aroyl, heteroaroyl, bromoacetyl, hydroxyacetyl, hydroxypropionyl, aminocarbonyl, N-alkylaminocarbonyl, N-mono- or N,N-disubstituted aminoalkanoyl radicals wherein said substituents are alkyl, aryl, aralkyl, cycloalkyl, heteroaralkyl, heterocycloalkyl, hydroxyethyl or methoxyethyl radicals, or in the case of a disubstituted aminoalkanoyl radical, said substituents along with the nitrogen atom to which they are attached form a heterocyclyl radical;

R' represents hydrogen radical;

$R^1$ represents hydrogen, alkyl, alkenyl or alkynyl radicals, or the side chain of the amino acid asparagine, S-methyl cysteine or the corresponding sulfoxide or sulfone derivatives thereof, leucine, isoleucine, allo-isoleucine, tert-leucine, alanine, norleucine, valine, threonine, serine or allo-threonine;

$R^{1'}$ represents hydrogen or alkyl radicals;

$R^{1''}$ represents hydrogen, —$CO_2CH_3$, —$CONH_2$ or alkyl of 1–4 carbon atoms radicals;

$R^2$ represents alkyl, cycloalkylalkyl or aralkyl radicals, each of which is optionally substituted with —$OR^9$, —$SR^9$ or halogen radicals, wherein $R^9$ represents hydrogen or alkyl radicals;

$R^3$ represents alkyl of 2–5 carbon atoms, alkenyl, hydroxyalkyl, cycloalkyl, cycloalkylalkyl, heterocycloalkylalkyl, aryl, aralkyl or heteroaralkyl radicals;

$R^4$ represents alkyl of 2–5 carbon atoms or cycloalkyl radicals; and $R^5$ represents hydrogen or alkyl of 2–5 carbon atoms radicals; or $R^4$ and $R^5$ together with the nitrogen atom to which they are bonded represent a 5–8 membered monocyclic or bicyclic heterocycloalkyl radical optionally substituted with an alkyl radical of 1–3 carbon atoms; and wherein unless otherwise defined above, alkyl, alone or in combination, means methyl, ethyl, n-propyl, isopropyl, n-butyl, isobutyl, sec-butyl, tert-butyl, pentyl, iso-amyl, hexyl or octyl radicals; alkenyl, alone or in combination, means ethenyl, propenyl or 1,4-butadienyl radicals; alkynyl, alone or in combination, means ethynyl, propynyl or butynyl radicals; alkoxy, alone or in combination, means methoxy, ethoxy, n-propoxy, isopropoxy, n-butoxy, iso-butoxy, sec-butoxy or tert-butoxy radicals; cycloalkyl, alone or in combination, means cyclopropyl, cyclobutyl, cyclopentyl or cyclohexyl radicals; aryl, alone or in combination, means phenyl or naphthyl radicals optionally substituted with one or more methyl, methoxy, fluoro, chloro, hydroxy or amino radicals; alkanoyl, alone or in combination, means acetyl, propionyl, butyryl, valeryl or 4-methylvaleryl radicals; heterocyclyl or heterocycloalkyl means pyrrolidinyl, alkylpyrrolidinyl, piperidinyl, alkylpiperidinyl, piperazinyl, N-alkylpiperazinyl, morpholinyl, thiamorpholinyl, tetrahydroisoquinolinyl or tetrahydroquinolinyl radicals; and heteroaryl means pyrrolyl, imidazolyl, N-benzyloxycarbonylimidazol-4-yl, pyrazolyl, pyridyl, pyrazinyl, pyrimidinyl, furyl, thienyl, triazolyl, oxazolyl, thiazolyl, indolyl, quinolinyl, isoquinolinyl, quinoxalinyl, β-carbolinyl, 2-benzofuranyl or benzimidazolyl radicals.

4. Method of claim 2 wherein R represents tertbutoxycarbonyl, benzyloxycarbonyl, (4-methoxyphenyl) methoxycarbonyl, acetyl, tertbutylcarbonyl, isobutylcarbonyl, phenyloxyacetyl, naphthyloxyacetyl, bromoacetyl, hydroxyacetyl, hydroxypropionyl, phenylcarbonyl, aminophenylcarbonyl, naphthylcarbonyl, aminonaphthylcarbonyl, pyridylcarbonyl, quinolinylcarbonyl, isoquinolinylcarbonyl, 2-benzofuranylcarbonyl, quinoxalinylcarbonyl, N,N-dimethylaminoacetyl, N-methyl-N-(hydroxyethyl)aminoacetyl, N-(methoxyethyl)aminoacetyl, N-benzylaminoacetyl, N-benzyl-N-methylaminoacetyl, N-(pyridylethyl)-N-methylaminoacetyl, N-phenylaminoacetyl, N-isobutylaminoacetyl, pyrrolidinylacetyl or morpholinylacetyl radicals;

R' represents hydrogen radical;

$R^1$ represents hydrogen, —$CF_3$, —$CH(CF_3)_2$, —$CH_2SO_2NH_2$, —$CH_2C(O)NHCH_3$, —$CH_2C(O)N(CH_3)_2$, —$C(CH_3)_2(SCH_3)$, —$C(CH_3)_2(S(O)CH_3)$, —$C(CH_3)_2(S(O)_2CH_3)$, methyl, ethyl, propyl, isopropyl, isobutyl, secbutyl, tertbutyl, neopentyl or propynyl radicals, or the side chain of the amino acid asparagine, S-methyl cysteine or the corresponding sulfoxide or sulfone derivatives thereof, leucine, isoleucine, alloisoleucine, tert-leucine, alanine, norleucine, valine, threonine, serine or allo-threonine;

$R^{1'}$ represents hydrogen or methyl radicals;

$R^{1''}$ represents hydrogen, —$CO_2CH_3$, —$CONH_2$ or methyl radicals;

$R^2$ represents —$CH_2CH_2SCH_3$, butyl, isobutyl, cyclohexylmethyl, benzyl, 4-fluorophenylmethyl or naphthylmethyl radicals;

$R^3$ represents isopropyl, butyl, isobutyl, tertbutyl, isoamyl, pentyl, neopentyl, propenyl, hydroxybutyl, cyclohexyl, cyclohexylmethyl, morpholinoethyl, phenyl, benzyl, 4-methoxyphenylmethyl, 4- fluorophenylmethyl, phenylethyl, or pyridylmethyl radicals;

$R^4$ represents ethyl, propyl, isopropyl, butyl, isobutyl, tertbutyl, isoamyl or 1,1-dimethylpropyl radicals; and $R^5$ represents hydrogen, ethyl or isopropyl radicals; or $R^4$ and $R^5$ together with the nitrogen atom to which they are bonded represent pyrrolidinyl, piperidinyl, methylpiperidinyl, ethylpiperidinyl, piperazinyl, N-methylpiperazinyl or morpholinyl radicals.

5. Method of claim 2 wherein t is 0;

R represents bromoacetyl, hydroxyacetyl, quinolinylcarbonyl, 2-benzofuranylcarbonyl, N,N-dimethylaminoacetyl, N-methyl-N-(hydroxyethyl)aminoacetyl, N-(methoxyethyl)aminoacetyl, N-benzylaminoacetyl, N-benzyl-N-methylaminoacetyl, N-(pyridylethyl)-N-methylaminoacetyl, N-phenylaminoacetyl, N-isobutylaminoacetyl, pyrrolidinylacetyl or morpholinylacetyl radicals;

R' represents hydrogen radical;

$R^1$ represents hydrogen, —$CH_2SO_2NH_2$, —$CH_2C(O)NHCH_3$, —$CH_2C(O)N(CH_3)_2$, —$C(CH_3)_2(SCH_3)$, —$C(CH_3)_2(S(O)CH_3)$, —$C(CH_3)_2(S(O)_2CH_3)$, isopropyl, isobutyl, secbutyl, tertbutyl, neopentyl or propynyl radicals, or the side chain of the amino acid asparagine, S-methyl cysteine or the corresponding sulfoxide or sulfone derivatives thereof, leucine, isoleucine, allo-isoleucine, tert-leucine, alanine, norleucine, valine, threonine, serine or allo-threonine;

$R^2$ represents —$CH_2CH_2SCH_3$, butyl, isobutyl, cyclohexylmethyl, benzyl, 4-fluorophenylmethyl or naphthylmethyl radicals;

$R^3$ represents isobutyl, isoamyl or cyclohexylmethyl radicals;

$R^4$ represents ethyl, propyl, isopropyl, butyl, isobutyl, tertbutyl, isoamyl or 1,1-dimethylpropyl radicals; and $R^5$ represents hydrogen, ethyl or isopropyl radicals; or $R^4$ and $R^5$ together with the nitrogen atom to which they are bonded represent pyrrolidinyl, piperidinyl, methylpiperidinyl, ethylpiperidinyl, piperazinyl, N-methylpiperazinyl or morpholinyl radicals.

6. Compound represented by the formula

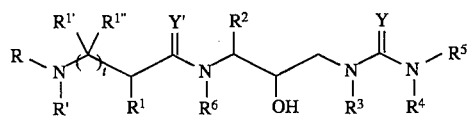

or a pharmaceutically acceptable salt, prodrug or ester thereof wherein t represents 0 or 1;

Y and Y' each independently represent O or S;

R represents hydrogen, alkoxycarbonyl, aralkoxycarbonyl, alkanoyl, aroyl, aryloxyalkanoyl, heterocyclylcarbonyl, heterocyclylalkanoyl, heteroaroyl, heteroaralkanoyl, alkyl, aralkyl, 3-carboxypropionyl, methyloxaloyl, bromoacetyl, trifluoroacetyl, methoxyacetyl, hydroxyacetyl, hydroxypropionyl, aminocarbonyl, N-alkylaminocarbonyl, N- mono- or N,N-disubstituted aminoalkanoyl radicals wherein said substituents are alkyl, aryl, aralkyl, cycloalkyl, heteroaralkyl, heterocycloalkyl, hydroxyethyl or methoxyethyl radicals, or in the case of a disubstituted aminoalkanoyl radical, said substituents along with the nitrogen atom to which they are attached form heterocyclyl or heteroaryl radicals, with the proviso that said heteroaryl radical is other than a quaternary nitrogen containing heteroaryl radical;

R' represents hydrogen, alkyl or aralkyl radicals; or R and R' together with the nitrogen to which they are attached form heterocycloalkyl or heteroaryl radicals, with the proviso that said heteroaryl radical is other than a quaternary nitrogen containing heteroaryl radical;

$R^1$ represents hydrogen, —$CF_3$, —$CH(CF_3)_2$, —$CH_2SO_2NH_2$, —$CO_2CH_3$, —$CONHCH_3$, —$CON(CH_3)_2$, —$CH_2C(O)NHCH_3$, —$CH_2C(O)N(CH_3)_2$, —$CONH_2$, —$C(CH_3)_2(SCH_3)$, —$C(CH_3)_2(S(O)CH_3)$, —$C(CH_3)_2(S(O)_2CH_3)$, alkyl, haloalkyl, alkenyl or alkynyl radicals, or the side chain of the amino acid asparagine, S-methyl cysteine or the corresponding sulfoxide or sulfone derivatives thereof, leucine, isoleucine, allo-isoleucine, tert-leucine, phenylalanine, ornithine, alanine, norleucine, glutamine, valine, threonine, serine, aspartic acid, beta-cyano alanine or allothreonine;

$R^{1'}$ represents hydrogen or alkyl radicals;

$R^{1''}$ represents hydrogen, —$CO_2CH_3$, —$CONH_2$ or alkyl radicals; or $R^{1'}$ together with $R^1$ and the carbon atoms to which they are attached represent a cycloalkyl radical;

$R^2$ represents alkyl, cycloalkylalkyl or aralkyl radicals, each of which is optionally substituted with —$OR^9$, —$SR^9$ or halogen radicals, wherein $R^9$ represents hydrogen or alkyl radicals;

$R^3$ represents alkyl, alkenyl, hydroxyalkyl, alkoxyalkyl, cycloalkylalkyl, heterocycloalkylalkyl, aralkyl or heteroaralkyl radicals, with the proviso that said radicals are attached to the nitrogen atom through an unbranched methylene radical;

$R^4$ represents alkyl, alkenyl, alkynyl, hydroxyalkyl, alkoxyalkyl, cycloalkyl, cycloalkylalkyl, heterocycloalkylalkyl, aryl or aralkyl radicals;

$R^5$ represents hydrogen or alkyl radicals; or $R^4$ and $R^5$ together with the nitrogen atom to which they are bonded represent a heterocycloalkyl radical; and $R^6$ represents hydrogen or alkyl radicals; and wherein alkyl, alone or in combination, means a straight-chain or branched-chain alkyl radical containing from 1 to 8 carbon atoms; alkenyl, alone or in combination, means a straight-chain or branched-chain hydrocarbon radial having one or more double bonds and containing from 2 to 8 carbon atoms; alkynyl, alone or in combination, means a straight-chain hydrocarbon radical having one or more triple bonds and containing from 2 to 10 carbon atoms; cycloalkyl, alone or in combination, means a cyclic alkyl radical which contains from 3 to 8 carbon atoms; aryl, alone or in combination, means a phenyl or naphthyl radical which is optionally substituted with one or more alkyl, alkoxy, halogen, hydroxy, amino or nitro radicals; heterocyclyl or heterocycloalkyl, alone or in combination, means a saturated or partially unsaturated monocyclic, bicyclic or tricyclic heterocycle which contains one or more nitrogen, oxygen or sulfur heteroatoms, which is optionally substituted on one or more carbon atoms by halogen, alkyl, alkoxy or oxo, or on a secondary nitrogen atom by alkyl, aralkoxycarbonyl, alkanoyl, phenyl or phenylalkyl, or on a tertiary nitrogen atom by oxido; and heteroaryl, alone or in combination, means an aromatic heterocyclyl.

7. Compound of claim 6, or a pharmaceutically acceptable salt, prodrug or ester thereof, wherein t represents 0 or 1;

Y and Y' each independently represent O or S;

R represents hydrogen, alkoxycarbonyl, aralkoxycarbonyl, alkanoyl, aroyl, aryloxyalkanoyl, heterocyclylcarbonyl, heterocyclylalkanoyl, heteroaroyl, alkyl, aralkyl, 3-carboxypropionyl, methyloxaloyl, bromoacetyl, trifluoroacetyl, methoxyacetyl, hydroxyacetyl, hydroxypropionyl, aminocarbonyl, N-alkylaminocarbonyl, N- mono- or N,N-disubstituted aminoalkanoyl radicals wherein said substituents are alkyl, aryl, aralkyl, cycloalkyl, heteroaralkyl, heterocycloalkyl, hydroxyethyl or methoxyethyl radicals, or in the case of a disubstituted aminoalkanoyl radical, said substituents along with the nitrogen atom to which they are attached form a heterocyclyl radical;

R' represents hydrogen, alkyl or aralkyl radicals; or R and R' together with the nitrogen to which they are attached form a heteroaryl radical, with the proviso that said heteroaryl radical is other than a quaternary nitrogen containing heteroaryl radical;

$R^1$ represents hydrogen, —$CF_3$, —$CH(CF_3)_2$, —$CH_2SO_2NH_2$, —$CO_2CH_3$, —$CONHCH_3$, —$CON(CH_3)_2$, —$CH_2C(O)NHCH_3$, —$CH_2C(O)N(CH_3)_2$, —$CONH_2$, —$C(CH_3)_2(SCH_3)$, —$C(CH_3)_2(S(O)CH_3)$, —$C(CH_3)_2(S(O)_2CH_3)$, alkyl, haloalkyl, alkenyl or alkynyl radicals, or the side chain of the amino acid asparagine, S-methyl cysteine or the corresponding sulfoxide or sulfone derivatives thereof, leucine, isoleucine, allo-isoleucine, tert-leucine, phenylalanine, ornithine, alanine, norleucine, glutamine, valine, threonine, serine, aspartic acid, beta-cyano alanine or allothreonine;

$R^{1'}$ represents hydrogen or alkyl radicals;

$R^{1''}$ represents hydrogen, —$CO_2CH_3$, —$CONH_2$ or alkyl radicals; or $R^{1'}$ together with $R^1$ and the carbon atoms to which they are attached represent a cycloalkyl radical;

$R^2$ represents alkyl, cycloalkylalkyl or aralkyl radicals, each of which is optionally substituted with —$OR^9$, —$SR^9$ or halogen radicals, wherein $R^9$ represents hydrogen or alkyl radicals;

$R^3$ represents alkyl, alkenyl, hydroxyalkyl, cycloalkylalkyl, heterocycloalkylalkyl, aralkyl or heteroaralkyl radicals, with the proviso that said radicals are attached to the nitrogen atom through an unbranched methylene radical;

$R^4$ represents alkyl or cycloalkyl radicals;

$R^5$ represents hydrogen or alkyl radicals; or $R^4$ and $R^5$ together with the nitrogen atom to which they are bonded represent a heterocycloalkyl radical; and $R^6$ represents a hydrogen radical.

8. Compound of claim 7, or a pharmaceutically acceptable salt, prodrug or ester thereof, wherein R represents hydrogen, alkoxycarbonyl, aralkoxycarbonyl, alkanoyl, aryloxyalkanoyl, aroyl, heteroaroyl, bromoacetyl, hydroxyacetyl, hydroxypropionyl, aminocarbonyl, N-alkylaminocarbonyl, N-mono- or N,N-disubstituted aminoalkanoyl radicals wherein said substituents are alkyl, aryl, aralkyl, cycloalkyl, heteroaralkyl, heterocycloalkyl, hydroxyethyl or methoxyethyl radicals, or in the case of a disubstituted aminoalkanoyl radical, said substituents along with the nitrogen atom to which they are attached form a heterocyclyl radical;

R' represents hydrogen radical;

$R^1$ represents hydrogen, alkyl, alkenyl or alkynyl radicals, or the side chain of the amino acid asparagine, S-methyl cysteine or the corresponding sulfoxide or sulfone derivatives thereof, leucine, isoleucine, allo-isoleucine, tert-leucine, alanine, norleucine, valine, threonine, serine or allo-threonine;

$R^{1'}$ represents hydrogen or alkyl radicals;

$R^{1''}$ represents hydrogen, —$CO_2CH_3$, —$CONH_2$ or alkyl of 1–4 carbon atoms radicals;

$R^2$ represents alkyl, cycloalkylalkyl or aralkyl radicals, each of which is optionally substituted with —$OR^9$, —$SR^9$ or halogen radicals, wherein $R^9$ represents hydrogen or alkyl radicals;

$R^3$ represents alkyl of 2–5 carbon atoms, alkenyl, hydroxyalkyl, cycloalkylalkyl, heterocycloalkylalkyl, aralkyl or heteroaralkyl radicals, with the proviso that said radicals are attached to the nitrogen atom through an unbranched methylene radical;

$R^4$ represents alkyl of 2–5 carbon atoms or cycloalkyl radicals; and $R^5$ represents hydrogen or alkyl of 2–5 carbon atoms radicals; or $R^4$ and $R^5$ together with the nitrogen atom to which they are bonded represent a 5–8 membered monocyclic or bicyclic heterocycloalkyl radical optionally substituted with an alkyl radical of 1–3 carbon atoms; and wherein unless otherwise defined above, alkyl, alone or in combination, means methyl, ethyl, n-propyl, isopropyl, n-butyl, isobutyl, sec-butyl, tert-butyl, pentyl, iso-amyl, hexyl or octyl radicals; alkenyl, alone or in combination, means ethenyl, propenyl or 1,4-butadienyl radicals; alkynyl, alone or in combination, means ethynyl, propynyl or butynyl radicals; alkoxy, alone or in combination, means methoxy, ethoxy, n-propoxy, isopropoxy, n-butoxy, iso-butoxy, secbutoxy or tert-butoxy radicals; cycloalkyl, alone or in combination, means cyclopropyl, cyclobutyl, cyclopentyl or cyclohexyl radicals; aryl, alone or in combination, means phenyl or naphthyl radicals optionally substituted with one or more methyl, methoxy, fluoro, chloro, hydroxy or amino radicals; alkanoyl, alone or in combination, means acetyl, propionyl, butyryl, valeryl or 4-methylvaleryl radicals; heterocyclyl or heterocycloalkyl means pyrrolidinyl, alkylpyrrolidinyl, piperidinyl, alkylpiperidinyl, piperazinyl, N-alkylpiperazinyl, morpholinyl, thiamorpholinyl, tetrahydroisoquinolinyl or tetrahydroquinolinyl radicals; and heteroaryl means pyrrolyl, imidazolyl, N-benzyloxycarbonylimidazol-4-yl, pyrazolyl, pyridyl, pyrazinyl, pyrimidinyl, furyl, thienyl, triazolyl, oxazolyl, thiazolyl, indolyl, quinolinyl, isoquinolinyl, quinoxalinyl, β-carbolinyl, 2-benzofuranyl or benzimidazolyl radicals.

9. Compound of claim 7, or a pharmaceutically acceptable salt, prodrug or ester thereof, wherein R represents tertbutoxycarbonyl, benzyloxycarbonyl, (4-methoxyphenyl methoxycarbonyl, acetyl, tertbutylcarbonyl, isobutylcarbonyl, phenyloxyacetyl, naphthyloxyacetyl, bromoacetyl, hydroxyacetyl, hydroxypropionyl, phenylcarbonyl, aminophenylcarbonyl, naphthylcarbonyl, aminonaphthylcarbonyl, pyridylcarbonyl, quinolinylcarbonyl, isoquinolinylcarbonyl, 2-benzofuranylcarbonyl, quinoxalinylcarbonyl, N,N-dimethylaminoacetyl, N-methyl-N-(hydroxyethyl)aminoacetyl, N-(methoxyethyl)aminoacetyl, N-benzylaminoacetyl, N-benzyl-N-methylaminoacetyl, N-(pyridylethyl)-N-methylaminoacetyl, N-phenylaminoacetyl, N-isobutylaminoacetyl, pyrrolidinylacetyl or morpholinylacetyl radicals;

R' represents hydrogen radical;

$R^1$ represents hydrogen, —$CF_3$, —$CH(CF_3)_2$, —$CH_2SO_2NH_2$, —$CH_2C(O)NHCH_3$, —$CH_2C(O)N(CH_3)_2$, —$C(CH_3)_2(SCH_3)$, —$C(CH_3)_2(S(O)CH_3)$, —$C(CH_3)_2(S(O)_2CH_3)$, methyl, ethyl, propyl, isopropyl, isobutyl, secbutyl, tertbutyl, neopentyl or propynyl radicals, or the side chain of the amino acid asparagine, S-methyl cysteine or the corresponding sulfoxide or sulfone derivarives thereof, leucine, isoleucine, allo-isoleucine, tert-leucine, alanine, norleucine, valine, threonine, serine or allo-threonine;

$R^{1'}$ represents hydrogen or methyl radicals;

$R^{1''}$ represents hydrogen, —$CO_2CH_3$, —$CONH_2$ or methyl radicals;

$R^2$ represents —$CH_2CH_2SCH_3$, butyl, isobutyl, cyclohexylmethyl, benzyl, 4-fluorophenylmethyl or naphthylmethyl radicals;

$R^3$ represents butyl, isobutyl, isoamyl, pentyl, neopentyl, propenyl, hydroxybutyl, cyclohexylmethyl, morpholinoethyl, benzyl, 4-methoxyphenylmethyl, 4-fluorophenylmethyl, phenylethyl, or pyridylmethyl radicals;

$R^4$ represents ethyl, propyl, isopropyl, butyl, isobutyl, tertbutyl, isoamyl or 1,1-dimethylpropyl radicals; and $R^5$ represents hydrogen, ethyl or isopropyl radicals; or $R^4$ and $R^5$ together with the nitrogen atom to which they are bonded represent pyrrolidinyl, piperidinyl, methylpiperidinyl, ethylpiperidinyl, piperazinyl, N-methylpiperazinyl or morpholinyl radicals.

10. Compound of claim 7, or a pharmaceutically acceptable salt, prodrug or ester thereof, wherein t is 0;

R represents bromoacetyl, hydroxyacetyl, quinolinylcarbonyl, 2-benzofuranylcarbonyl, N,N-dimethylaminoacetyl, N-methyl-N-(hydroxyethyl)aminoacetyl, N-(methoxyethyl)aminoacetyl, N-benzylaminoacetyl, N-benzyl-N-methylaminoacetyl, N-(pyridylethyl)-N-methylaminoacetyl, N-phenylaminoacetyl, N-isobutylaminoacetyl, pyrrolidinylacetyl or morpholinylacetyl radicals;

R' represents hydrogen radical;

$R^1$ represents hydrogen, —$CH_2SO_2NH_2$, —$CH_2C(O)NHCH_3$, —$CH_2C(O)N(CH_3)_2$, —$C(CH_3)_2(SCH_3)$, —$C(CH_3)_2(S(O)CH_3)$, —$C(CH_3)_2(S(O)_2CH_3)$, isopropyl, isobutyl, secbutyl, tertbutyl, neopentyl or propynyl radicals, or the side chain of the amino acid asparagine, S-methyl cysteine or the corresponding sulfoxide or sulfone derivatives thereof, leucine, isoleucine, allo-isoleucine, tert-leucine, alanine, norleucine, valine, threonine, serine or allo-threonine;

$R^2$ represents —$CH_2CH_2SCH_3$, butyl, isobutyl, cyclohexylmethyl, benzyl, 4-fluorophenylmethyl or naphthylmethyl radicals;

$R^3$ represents isobutyl, isoamyl or cyclohexylmethyl radicals;

$R^4$ represents ethyl, propyl, isopropyl, butyl, isobutyl, tertbutyl, isoamyl or 1,1-dimethylpropyl radicals; and $R^5$ represents hydrogen, ethyl or isopropyl radicals; or $R^4$ and $R^5$ together with the nitrogen atom to which they are bonded represent pyrrolidinyl, piperidinyl, methylpiperidinyl, ethylpiperidinyl, piperazinyl, N-methylpiperazinyl or morpholinyl radicals.

11. Compound of claim 6 which is

[1S-[1R*(R*),2S*]]-$N^1$-[3-[[[(1,1-dimethylethyl)amino]carbonyl](2-methylpropyl)amino]-2-hydroxy-1-(phenylmethyl) propyl]-2-[(2-quinolinylcarbonyl)amino]butanediamide;

[1S-[1R*(R*),2S*]]-$N^1$-[3-[[[(1,1-dimethylethyl)amino]carbonyl]propylamino]-2-hydroxy-1-(phenylmethyl)propyl]-2-[ (2-quinolinylcarbonyl)amino]-butanediamide;

[1S-[1R*(R*),2S*]]-$N^1$-[3-[[[(1,1-dimethylethyl)amino]carbonyl]butylamino]-2-hydroxy-1-(phenylmethyl)propyl]-2-[(2-quinolinylcarbonyl)amino]-butanediamide;

[1S-[1R*(R*),2S*]]-$N^1$-[3-[[[(1,1-dimethylethyl)amino]carbonyl](phenylmethyl)amino]-2-hydroxy-1-(phenylmethyl) propyl]-2-[(2-quinolinylcarbonyl)amino]-butanediamide;

[1S-[1R*(R*),2S*]]-$N^1$-[3-[[[(1,1-dimethylethyl)amino]carbonyl](4-fluorophenylmethyl)amino]-2-hydroxy-1-(phenyl methyl)propyl]-2-[(2-quinolinylcarbonyl)amino]-butanediamide;

[1S-[1R*(R*),2S*]]-$N^1$-[3-[[[(1,1-dimethylethyl)amino]carbonyl](4-methoxyphenylmethyl)amino]-2-hydroxy-1-(phenyl methyl)propyl]-2-[(2-quinolinylcarbonyl)amino]-butanediamide;

[1S-[1R*(R*),2S*]]-$N^1$-[3-[[[(1,1-dimethylethyl)amino]carbonyl](3-methylbutyl)amino]-2-hydroxy-1-(phenylmethyl)propyl]- 2-[(2-quinolinylcarbonyl)amino]-butanediamide;

[1S-[1R*(R*),2S* ]]-$N^1$-[3-[[[(1,1-dimethylethyl)amino]carbonyl](3,3-dimethylpropyl)amino]-2-hydroxy-1-(phenyl methyl)propyl ]-2-[(2-quinolinylcarbonyl)amino]-butanediamide;

[1S-[1R*(R*),2S*]]-$N^1$-[3-[[[(1,1-dimethylethyl)amino]carbonyl ](4-hydroxybutyl)amino]-2-hydroxy-1-(phenylmethyl)propyl]- 2-[(2-quinolinylcarbonyl)amino ]-butanediamide;

[1S-[1R*(R*),2S*]]-$N^1$-[3-[[[(1,1-dimethylethyl)amino]carbonyl](4-pyridylmethyl)amino]-2-hydroxy-1-(phenylmethylpropyl]- 2-[(2-quinolinylcarbonyl)amino ]-butanediamide;

[1S-[1R*(R*),2S*]]-$N^1$-[3-[[[(1,1-dimethylethyl)amino]carbonyl](2-phenylethyl)amino ]-2-hydroxy-1-(phenylmethyl)propyl]- 2-[(2-quinolinylcarbonyl)amino]-butanediamide;

[1S-[1R*(R*),2S* ]]-$N^1$-[3-[[[(1,1-dimethylethyl)amino]carbonyl](2-naphthylmethyl)amino]-2-hydroxy-1-(phenylmethyl) propyl]-2-[(2-quinolinylcarbonyl)amino]-butanediamide;

[1S-[1R*(R*),2S*]]-$N^1$-[3-[[[(1,1-dimethylethyl)amino]carbonyl ](cyclohexylmethyl)amino]-2-hydroxy-1-(phenylmethyl) propyl]-2-[(2-quinolinylcarbonyl)amino]-butanediamide;

[1S-[1R*(R*),2S*]]-$N^1$-[3-[[[(1,1-dimethylethyl)amino]carbonyl](3-methylbutyl)amino]-2-hydroxy-1-(4-fluorophenyl methyl)propyl]-2-[(2-quinolinylcarbonyl)amino]-butanediamide;

[1S-[1R*(R*),2S*]]-$N^1$-[3-[[[(1,1-dimethylethyl)amino]carbonyl](3-methylbutyl)amino]-2-hydroxy-1-(cyclohexylmethyl)propyl]- 2-[(2-quinolinylcarbonyl)amino]-butanediamide;

[1S-[1R*(R*),2S*]]-$N^1$-[3-[[[(1,1-dimethylethyl)amino]carbonyl](3-methylbutyl)amino]-2-hydroxy-1-(butyl)propyl]-2-[ (2-quinolinylcarbonyl)amino]-butanediamide;

[1S-[1R*(R*),2S*]]-$N^1$-[3-[[[(1,1-dimethylethyl)amino]carbonyl](2-methylpropyl)amino]-2-hydroxy-1-(phenylmethyl)propyl]- 2-[(phenylmethoxycarbonyl)amino]butanediamide;

[1S-[1R*(R*),2S*]]-$N^1$-[3-[[[(1,1-dimethylethyl)amino]carbonyl](3-methylbutyl)amino]-2-hydroxy-1-(phenylmethyl) propyl]-2-[(phenylmethoxycarbonyl)amino]butanediamide;

[1S-[1R*(R*),2S* ]]-$N^1$-[3-[[[(1,1-dimethylethyl)amino]carbonyl](2-naphthylmethyl)amino]-2-hydroxy-1-(phenylmethyl) propyl]-2-[(phenylmethoxycarbonyl)amino]butanediamide;

[1S-[1R*(R*),2S*]]-$N^1$-[3-[[[(1,1-dimethylethyl)amino]carbonyl](2-phenylethyl)amino]-2-hydroxy-1-(phenyl methyl) propyl]-2-[(phenylmethoxycarbonyl)amino]butanediamide;

[1S-[1R*(R*),2S*]]-N¹-[ 3-[[[(1,1-dimethylethyl)amino]carbonyl](3,3-dimethylpropyl)amino]-2-hydroxy-1-(phenylmethyl)propyl]- 2-[(phenylmethoxycarbonyl)amino]butanediamide;

[1S-[1R*(S*),2S*]]-3-(acetylamino)-N-[ 3-[[[(1,1-dimethylethyl)amino] carbonyl](3-methylbutyl)amino]-2-hydroxy- 1-(phenylmethyl)propyl]-2-methyl-propanamide;

[1S-[1R*(S*),2S*]]-3-(acetylamino)-N-[ 3-[[[(1,1-dimethylethyl)amino] carbonyl](3-methylbutyl)amino]-2-hydroxy- 1-(4-fluorophenylmethyl)propyl]-2-methyl-propanamide;

[1S-[1R*(S*),2S*]]-3-(acetylamino)-N-[ 3-[[[(1,1-dimethylethyl)amino] carbonyl](3-methylbutyl)amino]-2-hydroxy- 1-(cyclohexylmethyl)propyl]-2-methyl-propanamide;

[1S-[1R*(S*),2S*]]-3-(phenoxyacetylamino)-N-[ 3-[[[(1,1-dimethylethyl)amino] carbonyl](3-methylbutyl)amino]-2-hydroxy- 1-(phenylmethyl)propyl]-2-methyl-propanamide;

[1S-[1R*(S*),2S*]]-3-( 2-naphthyloxyacetylamino)-N-[-3-[[[(1,1-dimethylethyl)amino] carbonyl](3-methylbutyl)amino]-2-hydroxy- 1-(phenylmethyl)propyl]-2-methyl-propanamide;

[1S-[1R*(S *),2 S * ]]-3-( 4-methoxybenzyloxycarbonyl)amino-N-[3-[ [[(1,1-dimethylethyl)amino]carbonyl]( 3-methylbutyl)amino]-2-hydroxy- 1-(phenylmethyl)propyl]-2-methyl-propanamide;

[4R-(4R*,7S*,8R*)]- 8-hydroxy-N, 4,13,13-tetramethyl-10-(3-methylbutyl)- 5,11-dioxo-7-(phenylmethyl)-2,6,10,12-tetraazatetradecanamide;

[4R-(4R*, 7S*,8R*)]-8-hydroxy-N, 4,13,13-tetramethyl-10-(3methylbutyl)- 5,11-dioxo-7-(4-fluorophenylmethyl)- 2,6,10,12-tetraazatetradecanamide;

[1S-[1R*(R*),2S*]]-N¹-[ 2-hydroxy-3-[(phenylmethyl)(1-pyrrolidinylcarbonyl)amino]- 1-(phenylmethyl)propyl]-2-[(2-quinolinylcarbonyl)amino]-butanediamide;

[1S-[1R*(R*),2S*]]-N¹-[2-hydroxy- 3-[(4-fluorophenylmethyl) (1-pyrrolidinyl)amino]- 1-(phenylmethyl)propyl]-2-[(2-quinolinylcarbonyl)amino]-butanediamide;

[1S-[1R*(R*),2S*]]-N¹-[2-hydroxy- 3-[(3-methylbutyl)(4-morpholinylcarbonyl)amino]- 1-(phenylmethyl)propyl]-2-[(2-quinolinylcarbonyl)amino]-butanediamide;

[1S-[1R*(R*),2S*]]-N¹-[2-hydroxy- 3-[(4-fluorophenylmethyl)(4-morpholinylcarbonyl)amino]- 1-(phenylmethyl)propyl]-2-[(2-quinolinylcarbonyl)amino]-butanediamide;

[1S-[1R*(R*),2S*]]-N¹-[2-hydroxy-3-[( 4-fluorophenylmethyl)(1-piperidinylcarbonylamino]- 1-(phenylmethyl)propyl]-2-[(2-quinolinylcarbonyl)amino]-butanediamide;

[1S-[1R*(R*),2S*]]-2-(acetylamino)-N-[3-[ [[(1,1-dimethylethyl)amino]carbonyl]( 3-methylbutyl)amino]-2-hydroxy- 1-(phenylmethyl)propyl]-3,3-dimethyl-butaneamide;

[1S-[1R*(R*),2S*]]-2-(acetylamino)-N-[ 3-[[[(1,1-dimethylethyl)amino]carbonyl]( 3-methylbutyl)amino]-2-hydroxy- 1-(4-fluorophenylmethyl)propyl]-3,3-dimethyl-butaneamide;

[1S-[1R*(R*),2S*]]-2-(acetylamino)-N-[ 3-[[[(1,1-dimethylethyl)amino]carbonyl]( 4-fluorophenylmethyl)amino ]-2-hydroxy- 1-(phenylmethyl)propyl]-3,3-dimethyl-butaneamide;

[1S-[1R*(R*),2S*]]-2-[( 2,2-dimethylaminoacetyl)amino]-N-[3-[ [[(1,1-dimethylethyl)amino]carbonyl] (3-methylbutyl)amino]-2-hydroxy- 1-(phenylmethyl)propyl ]-3,3-dimethyl-butaneamide; or

[1S-[1R*(R*),2S* ]]-N¹-[ 3-[[[(1,1-dimethylethyl)amino]carbonyl]( 3-methylbutyl)amino]-2-hydroxy-1-(phenylmethyl) propyl]-3-[(2-quinolinylcarbonyl)amino]-butaneamide.

12. A pharmaceutical composition comprising a compound of claim 6 and a pharmaceutically acceptable carrier.

13. Method of treating a retroviral infection comprising administering an effective amount of a composition of claim 12.

14. Method of claim 13 wherein the retroviral infection is an HIV infection.

15. Method for treating AIDS comprising administering an effective amount of a composition of claim 12.

16. Method of inhibiting a retroviral protease comprising administering a protease inhibiting amount of a composition of claim 12.

17. Method of claim 16 wherein the retroviral protease is HIV protease.

18. Method of claim 1 wherein the retroviral protease is HIV protease.

\* \* \* \* \*